US008481005B2

(12) United States Patent
Jewett et al.

(10) Patent No.: US 8,481,005 B2
(45) Date of Patent: Jul. 9, 2013

(54) METHODS TO PREVENT CYTOTOXICITY USING N-ACETYL-CYSTEINE

(75) Inventors: Anahid Jewett, Valencia, CA (US); Avina Paranjpe, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/976,820

(22) Filed: Dec. 22, 2010

(65) Prior Publication Data
US 2011/0165098 A1     Jul. 7, 2011

Related U.S. Application Data

(63) Continuation of application No. 12/159,911, filed as application No. PCT/US2007/060025 on Jan. 2, 2007, now abandoned.

(60) Provisional application No. 60/755,947, filed on Jan. 3, 2006, provisional application No. 60/805,829, filed on Jun. 26, 2006.

(51) Int. Cl.
| *A61K 8/02* | (2006.01) |
| *A01N 39/00* | (2006.01) |
| *A61C 15/00* | (2006.01) |
| *A61C 5/00* | (2006.01) |

(52) U.S. Cl.
USPC .............. 424/50; 424/401; 424/616; 424/49; 433/216; 433/217.1

(58) Field of Classification Search
USPC ................. 424/49, 401, 616; 433/216, 217.1
See application file for complete search history.

(56) References Cited

U.S. PATENT DOCUMENTS

| 5,260,021 | A | * | 11/1993 | Zeleznick | ........................ 422/28 |
| 5,276,068 | A | | 1/1994 | Waknine | |
| 5,875,799 | A | * | 3/1999 | Petrus | .......................... 132/323 |
| 2003/0003059 | A1 | * | 1/2003 | Dana | ................................ 424/49 |
| 2005/0271602 | A1 | * | 12/2005 | Milanovich et al. | ............ 424/49 |
| 2008/0306158 | A1 | | 12/2008 | Jewett et al. | |

FOREIGN PATENT DOCUMENTS

| WO | WO2005/017094 | 2/2005 |
| WO | WO2007/112134 | 10/2007 |

OTHER PUBLICATIONS

PCT International Search Report and Written Opinion dated Apr. 18, 2008 issued in WO2007/112134 [PCT/US2007/060025].
PCT International Preliminary Report on Patentability dated Jul. 8, 2008 issued in WO2007/112134 [PCT/US2007/060025].
Paranjpe et al. (2005) "Resin Monomer 2-Hydroxyethyl Methacrylate (HEMA) is a Potent Inducer of Apoptotic Cell Death in Human and Mouse Cells" *J. Dent. Res.* 84(2): 172-177.
Roberts et al. (1995) "N-Acetylcysteine Enhances Antibody-Dependent Cellular Cytotoxicity in Neutrophils and Mononuclear Cells from Healthy Adults and Human Immunodeficiency Virus-Infected Patients" Journal of Infectious Diseases 172(6): 1492-1502.
Soheili et al. (2003) "In vitro effects of ascorbate and Trolox on the biocompatibility of dental restorative materials" *Biomaterials* 24(1): 3-9.
Stanislawski et al. (2000) "Dental restorative biomaterials induce glutathione depletion in cultured human gingival fibroblast: Protective effect of N-acetylcysteine" *J. Biomed. Mater. Res.* 51: 469-474.
Stanislawski et al. (2003) "TEGDMA-induced toxicity in human fibroblasts is associated with early and drastic glutathione depletion with subsequent production of oxygen reactive species." *Journal of Biomedical Materials Research* 66A(3): 476-482.
Walther et al. (2004) " Antioxidative vitamins decrease cytotoxicity of HEMA and TEGDMA in cultured cell lines" *Archives of Oral Biology* 49(2): 125-131.
Williamson et al. (1968) "Use of a New Buffer in the Culture of Animal Cells" *J. Gen. Viral.*, 2: 309-312.
Yoshii (1997) "Cytotoxic effects of acrylates and methacrylates: relationships of monomer structures and cytotoxicity" *Journal of Biomedical Materials Research* 37(4): 517-524.
US Office Action dated Sep. 16, 2009 issued in U.S. Appl. No. 12/159,911.
US Final Office Action dated Jun. 28, 2010 issued in U.S. Appl. No. 12/159,911.

* cited by examiner

*Primary Examiner* — Lezah Roberts
*Assistant Examiner* — Tracy Liu
(74) *Attorney, Agent, or Firm* — Emily M. Haliday; Weaver Austin Villeneuve & Sampson LLP

(57) ABSTRACT

Compositions and methods to inhibit adverse physiological effects caused by resin-based and resin-containing materials are disclosed. More specifically, the use of N-acetyl-cysteine (NAC) to inhibit hydroxyethyl methacrylate (HEMA)-mediated cell death and cytotoxicity.

6 Claims, 57 Drawing Sheets

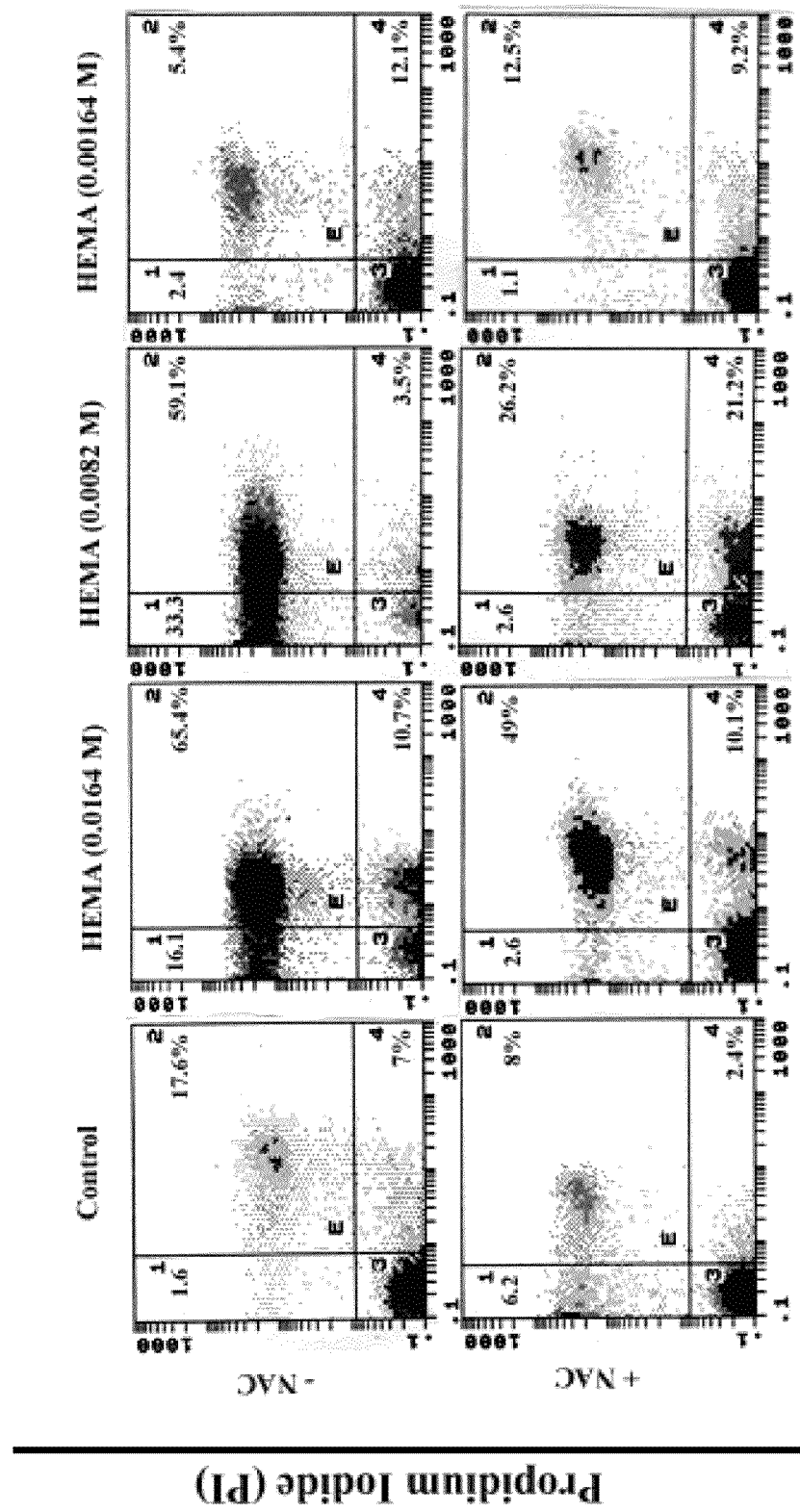

FIG. 22A
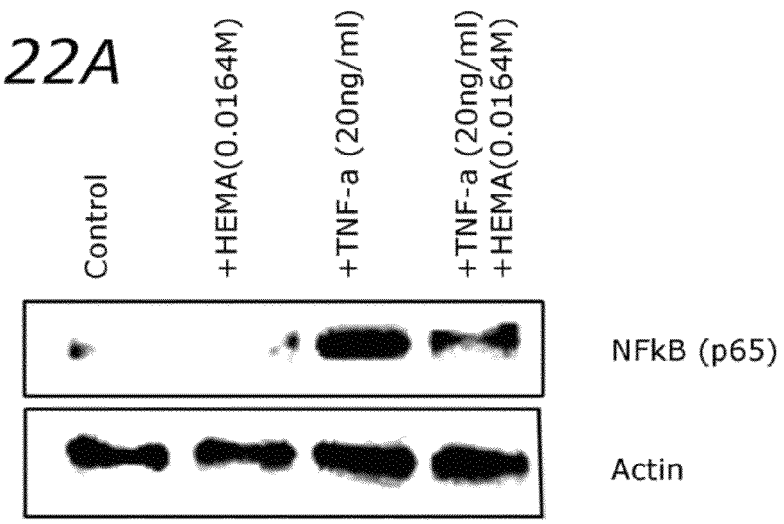
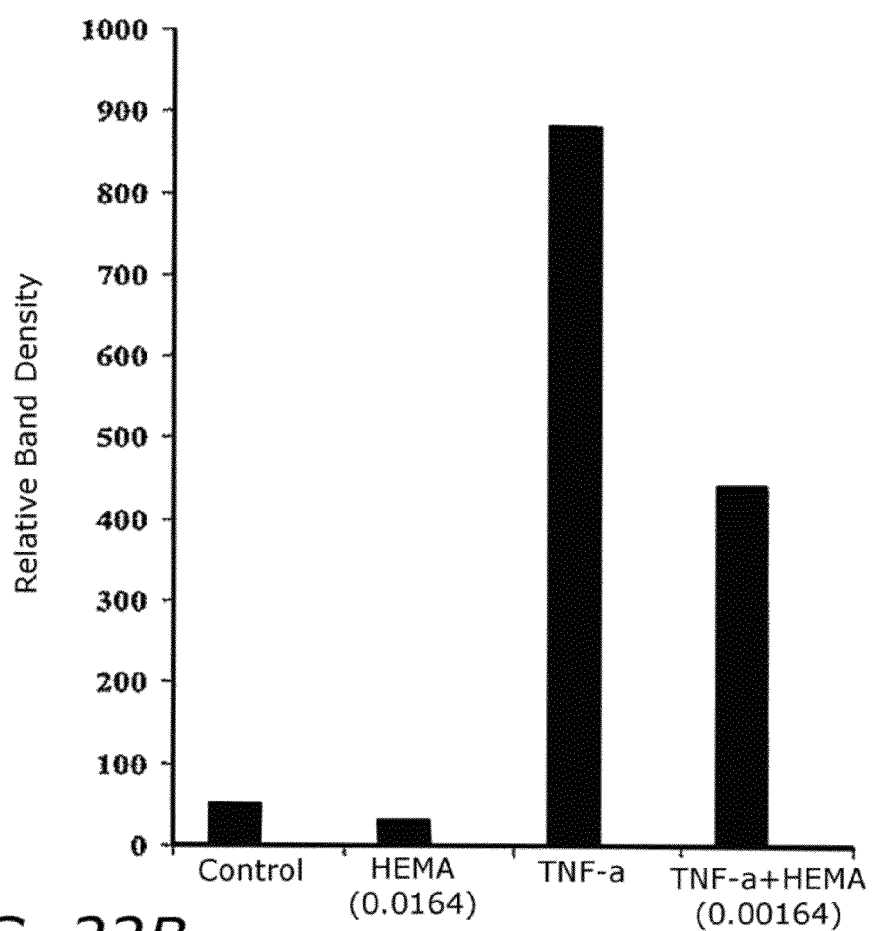
FIG. 22B

FIG. 23A
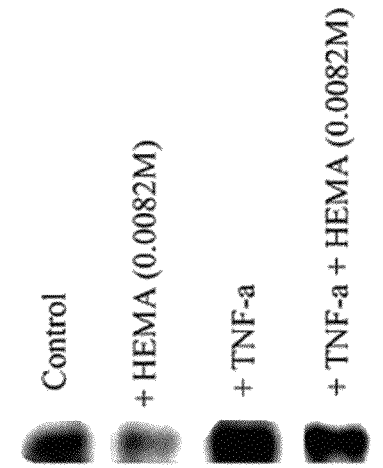
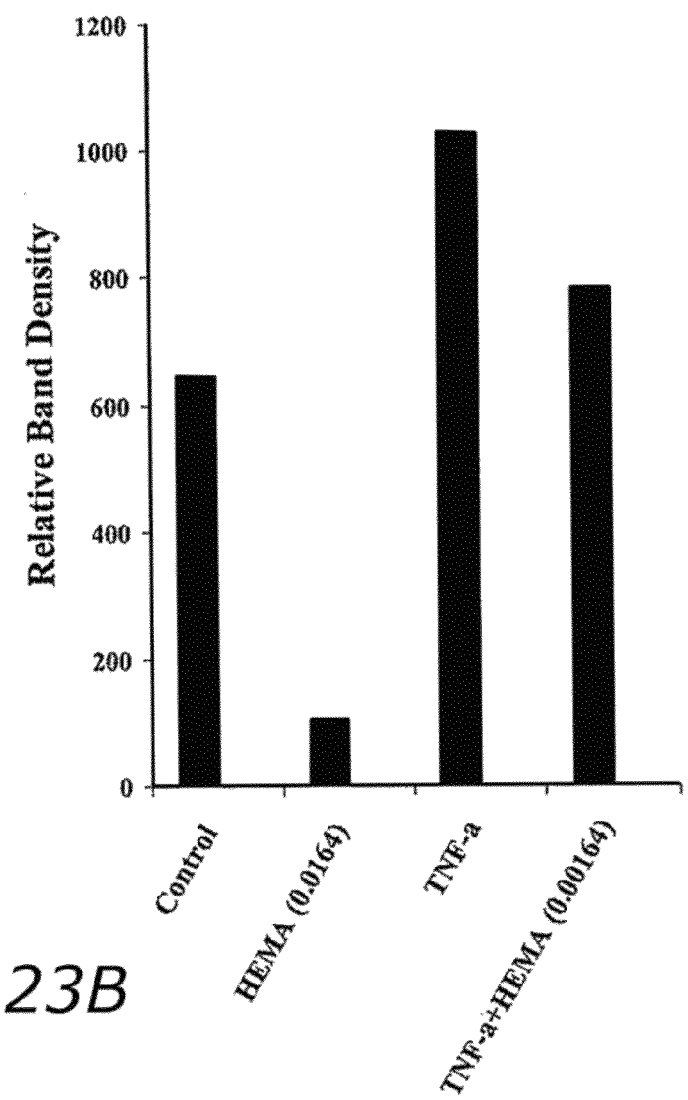
FIG. 23B

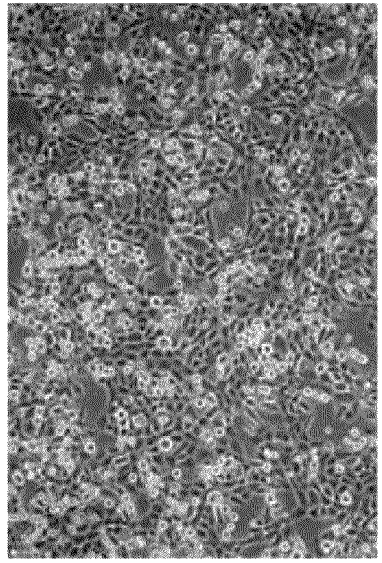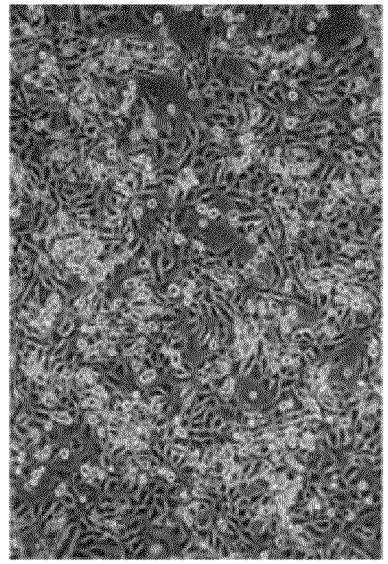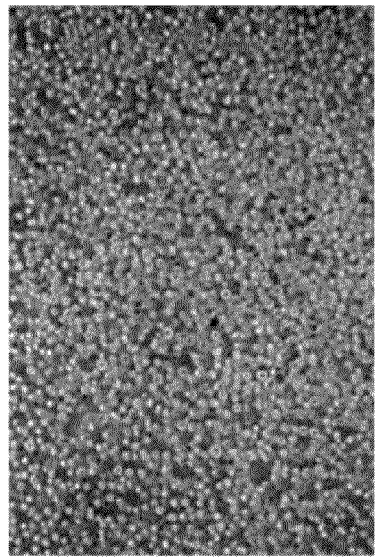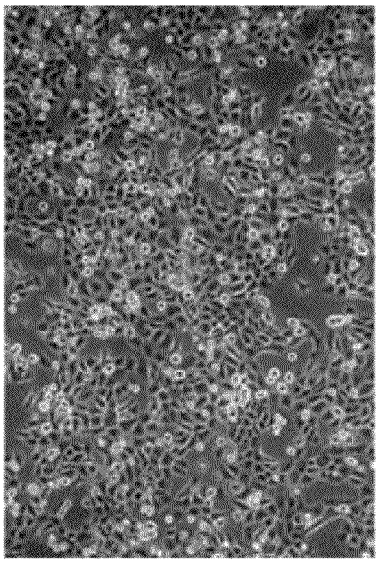
FIG. 27

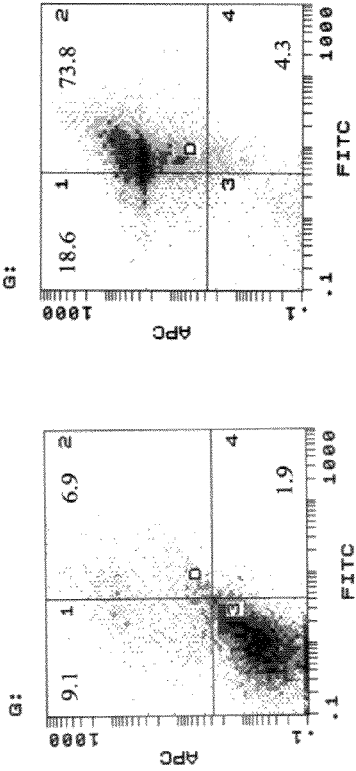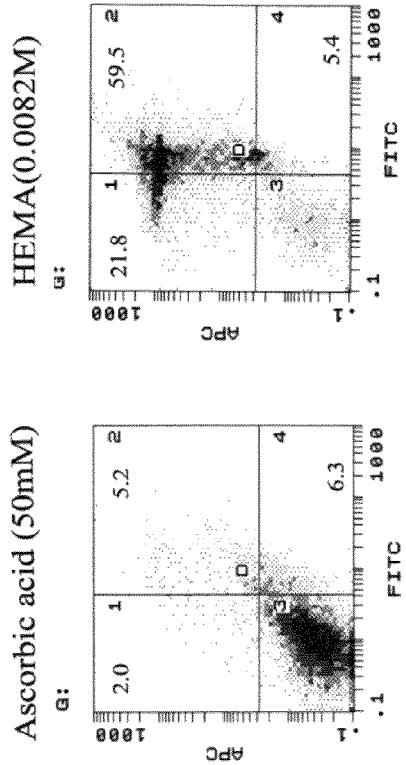
FIG. 34

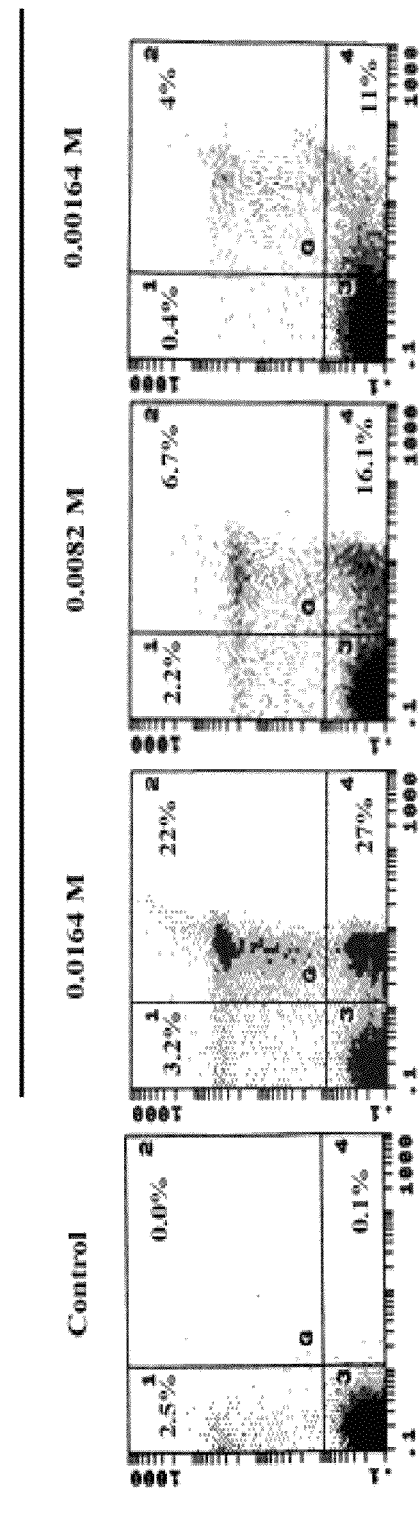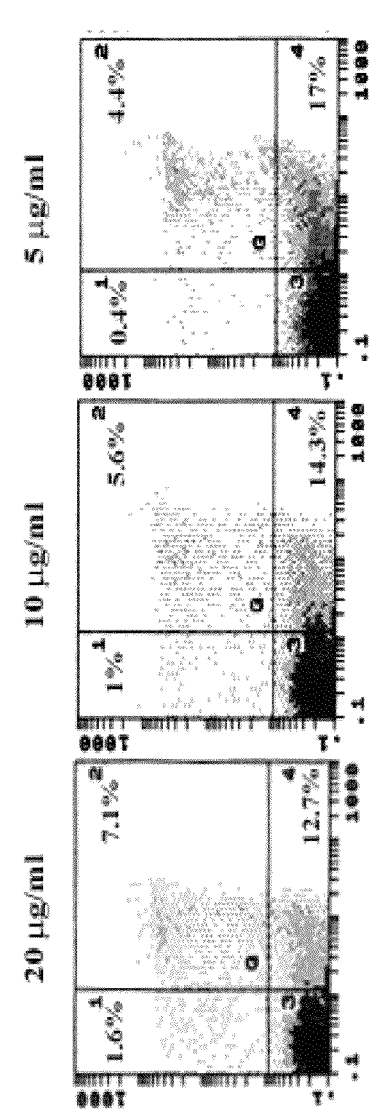
FIG. 39A

METHODS TO PREVENT CYTOTOXICITY USING N-ACETYL-CYSTEINE

CROSS REFERENCE TO RELATED APPLICATIONS

The present application is a continuation of U.S. Ser. No. 12/159,911, filed Jul. 2, 2008, now abandoned which claims the benefit under 35 USC 371 to PCT/US2007/060025 filed on Jan. 2, 2007, 35 U.S.C. §119(e) to U.S. Provisional Patent Application Nos. 60/755,947, filed Jan. 3, 2006 and 60/805,829, filed Jun. 26, 2006, the disclosures of which are incorporated herein in their entirety.

STATEMENT REGARDING FEDERALLY SPONSORED RESEARCH OR DEVELOPMENT

This invention was made with United States Government support of Grant No. DE10331 awarded by the National Institutes of Health. The United States Government has certain rights in this invention.

FIELD OF THE INVENTION

The present invention relates to resin-based and resin-containing materials and bleaching agents commonly used in dental and other practices. More specifically, the present invention relates to compositions and methods to inhibit adverse physiological effects caused by these materials. More specifically, the present invention relates to the use of N-acetyl-cysteine (NAC) to inhibit cell death and cytotoxicity mediated by hydroxyethyl methacrylate (HEMA) composites and a variety of other resin monomers that are routinely used in dentistry as well as in the applications where resin monomers are used to either restore or promote functions.

BACKGROUND OF THE INVENTION

Resin-based and resin-containing materials are now routinely used in dental and other practices. For example, resin-based and resin-containing materials are found in direct filling materials (both composite resin and glass ionomer-resin hybrids), in fissure sealing agents, and in bonding resins or resin cements for metal, porcelain and resin inlays, veneers, crowns and bridges. These resin-based or resin-containing materials are part of 'bonded' amalgam restorations, 'bonded' posts and 'bonded' orthodontic brackets. The use of these materials will likely continue to increase in the future, particularly as alternatives to dental amalgam are sought.

One of the attractive features of the resin materials now in use is that they can adhere to both dentin and enamel. Most dentin bonding technologies use a primer containing the hydrophilic resin hydroxyethyl methacrylate (HEMA; molecular weight 130) in combination with acid treatment to create a 'hybrid layer' or 'interdiffusion zone.' The next material placed is a bonding resin, commonly 2,2-bis-(4-(2-hydroxy-3-methacryloxypropoxy)phenyl)propane (Bis-GMA)-based with bis-GMA/triethylene glycol dimethacrylate (TEGDMA; molecular weight 286) in amounts varying from 30-50%. Then a restorative resin, most of which also contain TEGDMA in the range of 15-25% is placed as the final step. TEGDMA proportions are higher in resin fissure sealants and cements. Enamel bonding omits the primer step. Resin-modified glass ionomers include HEMA.

While HEMA is found in many medical devices and materials such as soft contact lenses, electrosurgical grounding plates and drug delivery systems, its use in such materials may not cause much of a public health concern because, in such uses, the HEMA is polymerized before use in the body. In contrast, in dentistry, HEMA-containing materials require polymerization intraorally, and as a result, may contain about 30% unpolymerized monomers. These unpolymerized monomers can leach out to the surrounding tooth area, and into the oral environment where they can cause adverse effects.

The adverse effects of HEMA can occur directly due to its cytotoxic effects and indirectly by mobilizing immune effector cells thereby causing sensitization and allergy. For example, use of such materials can cause allergies in dental personnel who work with the compounds (responses are usually Type IV (delayed-type hypersensitivity [DTH] cell-mediated, however anaphylactic responses (Type I hypersensitivity, antibody-mediated) to HEMA also can occur). Contact dermatitis, particularly of the fingers, can severely compromise or even end a career in dentistry. These same effects can occur in patients, especially as HEMA is released in vivo from many resin-based tooth restorative materials used in dentistry in microgram to milligram amounts in the first days after placement of clinically-used amounts of the source materials. The presence of HEMA can cause cell death, pulp cell damage and acute pulpal inflammation as well as dilation and congestion of blood vessels resulting in inflammation, formation of pulp abscesses and prevention of pulp healing and dentin regeneration. Moreover, dental resins can interfere with the pulp healing process.

The method by which resin monomers induce apoptosis has not been completely elucidated. However, apoptosis induced by HEMA has been related to a decrease in intracellular glutathione (GSH) levels and the production of reactive oxygen species (ROS) by the cells. Under conditions of abundant ROS production, the body's antioxidant defenses may be overwhelmed leading to oxidative stress and cell and DNA damage which in turn leads to programmed cell death. An effective way of preventing ROS induced apoptosis and promoting cell survival could therefore be the use of exogenous anti-oxidants.

The foregoing suggests that an antioxidant, such as N-acetyl-cysteine, could inhibit the adverse effects caused by HEMA-containing dental resins. N-acetyl cysteine (NAC) is a unique compound which acts as a reductant both by its own reducing power and by stimulating the synthesis of the major cellular reductant GSH. In the N-acetylated form, the redox state of cysteine is markedly stabilized. After free NAC enters a cell, it is rapidly hydrolyzed to release cysteine. Therefore, NAC provides a potential avenue to inhibit the adverse effects of HEMA.

SUMMARY OF THE INVENTION

When teeth from humans are restored with conventional restorative materials, the restorative materials can cause significant toxicity to the cells lining the tooth, often causing pathologies ranging from simple tooth sensitivity to food and fluid intake, the need for a root canal, and to more serious disease states, including allergies to the restorative material. The present invention provides an inhibitor of the toxicity of these restorative materials. Specifically, the present invention demonstrates the effectiveness of N-acetyl-cysteine (NAC), a caspase inhibitor and thiol antioxidant, in ameliorating the adverse effects of resin monomers an example of which is HEMA.

Specifically, one embodiment according to the present invention includes a restorative material comprising an effective amount of NAC. In another embodiment the restorative material is a dental restorative material. In another embodiment, the dental restorative material is selected from the group consisting of composite resins, glass ionomer-resin hybrids, fissure sealing agents, bonding resins, resin cements for metal, resin cements for porcelain, resin inlays, veneers, crowns, bridges and combinations thereof.

In one embodiment according to the present invention, the effective amount of NAC is from about 10 mM to about 30 mM of the restorative material. In another embodiment, the effective amount of NAC is about 20 mM of the restorative material.

In another embodiment according to the present invention, the restorative material is used at least in part to prevent cell death in a cell type selected from the group consisting of macrophages, peripheral blood mononuclear cells, skin keratinocytes, dental pulp stromal cells, odontoblasts, gingival cells, stem cells, mesenchymal stem cells, perivascular stem cells, muscle cells, smooth muscle cells, osteoblasts, and combinations thereof.

In another embodiment the restorative material prevents an effect selected from the group consisting of cell death, allergy, tooth loss, and combinations thereof.

The present invention also includes methods. One method embodiment according to the present invention comprises inhibiting cytotoxicity by administering an effective amount of NAC. In another embodiment, the cytotoxicity is caused by a restorative material. In another embodiment the restorative material comprises HEMA. In another embodiment the restorative material is a dental restorative material. In another embodiment the dental restorative material is selected from the group consisting of composite resins, glass ionomer-resin hybrids, fissure sealing agents, bonding resins, resin cements for metal, resin cements for porcelain, resin inlays, veneers, crowns, bridges, and combinations thereof.

In one embodiment of the methods of the present invention, the effective amount of NAC is administered due to being included as a component of the restorative material. In another embodiment the NAC is included as the component in the restorative material in an amount of about 10 mM to about 30 mM. In another embodiment the NAC is included as the component in the restorative material in an amount of about 20 mM.

In one method embodiment according to the present invention, the effective amount of NAC is administered as a separate material from the restorative material. In another embodiment the NAC is administered in a time manner selected from the group consisting of before the administration of the restorative material; About 30 minutes to about 8 hours before the administration of the restorative material; about 8 hours to about 3 days before the administration of the restorative material; within about 2 hours after the administration of the restorative material; and combinations thereof.

In one embodiment of the present invention, cytotoxicity causes an effect selected from the group consisting of cell death, allergy, tooth loss, and combinations thereof. In another embodiment the cytotoxicity is caused by HEMA.

BRIEF DESCRIPTION OF THE FIGURES

FIGS. 1A and 1B show dose-dependent hydroxyethyl methacrylate (HEMA)-induced cell death in RAW 264.7 and THP-1 cells and the inhibition of this cytotoxicity by N-acetyl cysteine (NAC).

FIGS. 22A and 22B show that the nuclear expression of NFkβ is inhibited in oral keratinocytes after HEMA treatment.

FIGS. 23A and 23B show that the nuclear expression of NFkβ is inhibited in dental pulp stromal cells after HEMA treatment.

FIGS. 26 and 27 show that HEMA induces significant cell death in NFkβ HOKs.

FIG. 34 shows that ascorbic acid fails to reverse HEMA-mediated cell death.

FIGS. 39A and 39B compare the toxic effects of HEMA to cisplatin by two different methods.

FIGS. 47-49 show the protective effect of NAC in the presence of bleaching agents in dental pulp stromal cells.

DETAILED DESCRIPTION OF THE INVENTION

Exposure to hydroxyethyl methacrylate (HEMA) significantly induces apoptotic cell death in a dose-dependent manner (Paranjpe et al. 84(2), J. Dent. Res. 2005). The present studies demonstrate, among other things, that this cell death can be inhibited by N-acetyl cysteine (NAC), providing a mechanism to ameliorate some of the negative effects of HEMA in patient treatment.

Unless otherwise provided, the following generalized methods were used in the experiments described below. Cell lines were stimulated with concentrations of HEMA ranging from 0.082M to 0.000182M. Stimulations occurred for time periods ranging from about 4 to about 24 hours. NAC stock solutions (1 M) were made in N[2-hydroxyethyl]piperazine-N'-[2-ethanesulfonic acid] (HEPES) and 10M NaOH immediately before use and were diluted to a final concentration of 20 mM in culture medium. NAC was added either simultaneously with HEMA or added about 1 to about 2 hours before the addition of HEMA to the cells. HEMA, NAC, HEPES, propidium iodide, RNase, and ethanol were purchased from Sigma (St. Louis, Mo.).

A. NAC Inhibits HEMA-Mediated Cell Death and Cytotoxicity

The ability of NAC to inhibit HEMA-mediated cell death and cytotoxicity was evaluated in a number of different relevant cell types.

1. Macrophages

The ability of NAC to inhibit HEMA-mediated cell death and cytotoxicity in murine and human macrophage cell lines was evaluated. RAW 264.7 cells (murine macrophages) were obtained from American Type Culture Collection (ATCC) and were cultured in a 5% $CO_2$ atmosphere in DMEM (purchased from Cellgro (Herndon, Va.)) containing 10% FCS, 1% penicillin-streptomycin, 1% sodium pyruvate, 1% non essential amino acids and 1% glutamine. THP-1 cells (human macrophages) were obtained from ATCC and were cultured under the same conditions, with RMPI 1640 containing 10% FCS, 1% penicillin-streptomycin, 1% sodium pyruvate and 1% non essential amino acids.

Figure 1A:
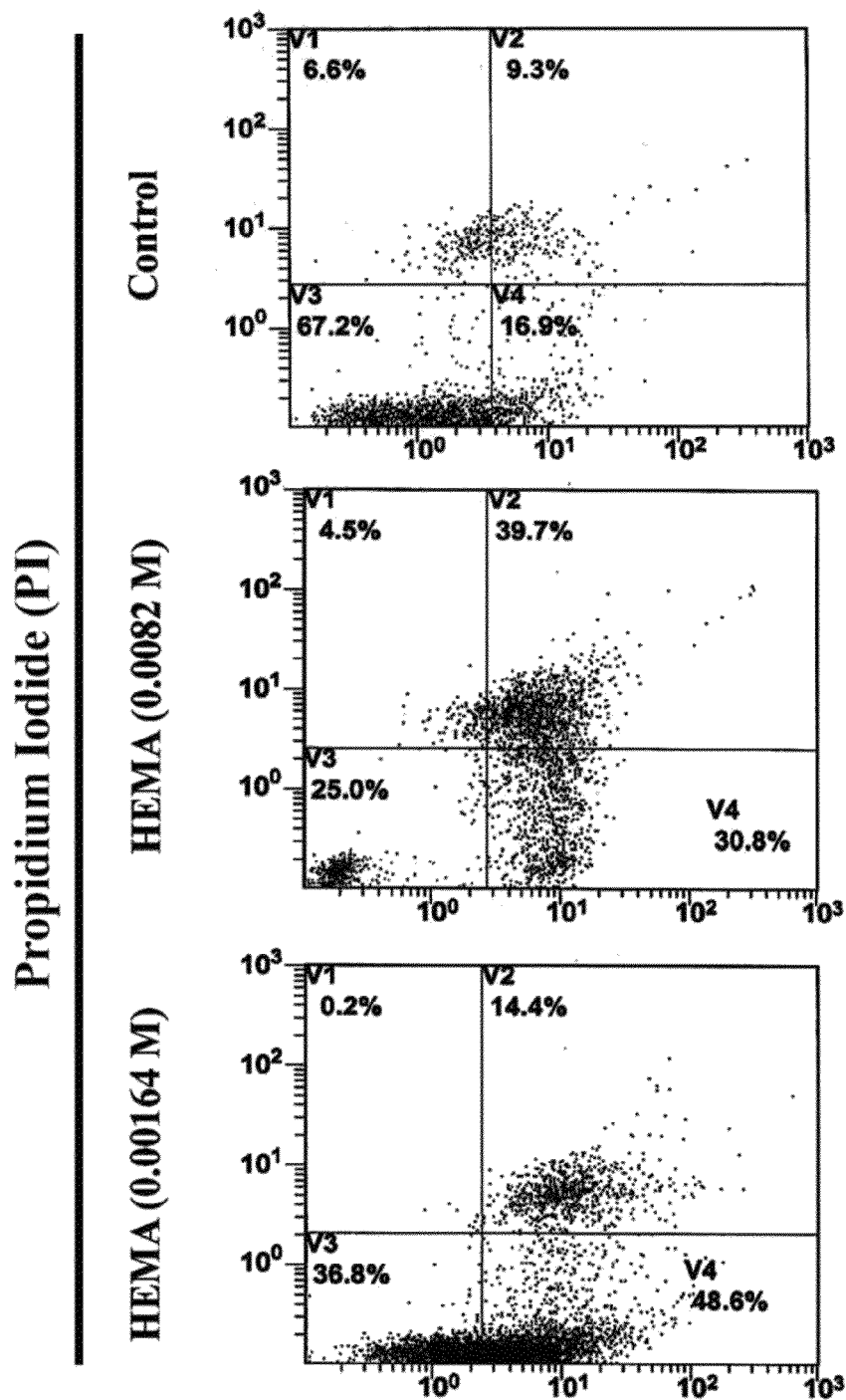

Before evaluating the ability of NAC to inhibit HEMA-mediated cytotoxicity, the concentration of HEMA required to induce significant apoptosis was first determined. Dose-dependent apoptosis was measured by FITC-Annexin V/Propidium iodide kits (Miami, Fla.). Cells were plated in six-well/twelve well plates. The cells were treated with 0.0082M or 0.0164M HEMA for about 18 hours. Cells were washed twice with PBS and centrifuged at about 2000 rpm for about 5 minutes and resuspended in binding buffer (provided in the kit) along with FITC-Annexin V/Propidium iodide (PI) according to manufacturer's instructions. After incubating on ice (light protected) for about 15 minutes, samples were analyzed by flow cytometry. Flow cytometric analysis was performed using a flow cytometer equipped with a single 488-nm argon laser. Dead cell fragments were gated out by forward and side scatter analysis. Where dual color PI/Annexin V-FITC analysis was performed, PI fluorescence was displayed in channel FL-2, while the FITC fluorescence was displayed in channel Fl-1. Forward and side scatter were used to gate out cellular fragments. As can be seen in FIGS. 1A and 1B, the results of the study demonstrated that while murine RAW 264.7 cells can be more sensitive than human THP-1 cell lines to HEMA, HEMA-mediated cell death and cytotoxicity was detected at millimole to micromole concentrations in both RAW 264.7 and THP-1 cell lines.

Figure 2A:
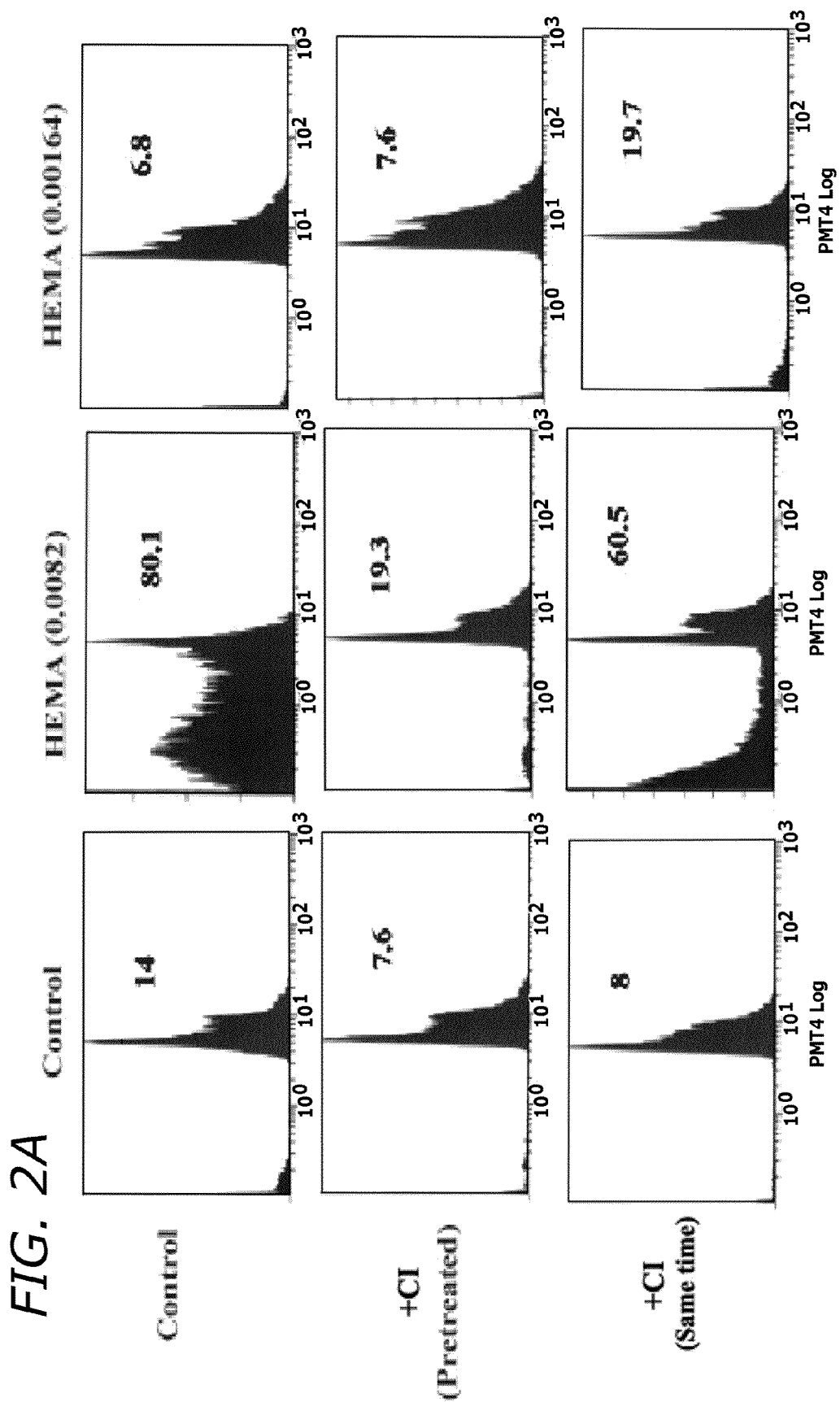
FIGS. 2A and 2B show the inhibition of HEMA-mediated cell death by pretreatment and simultaneous treatment with NAC.
Figure 2B:
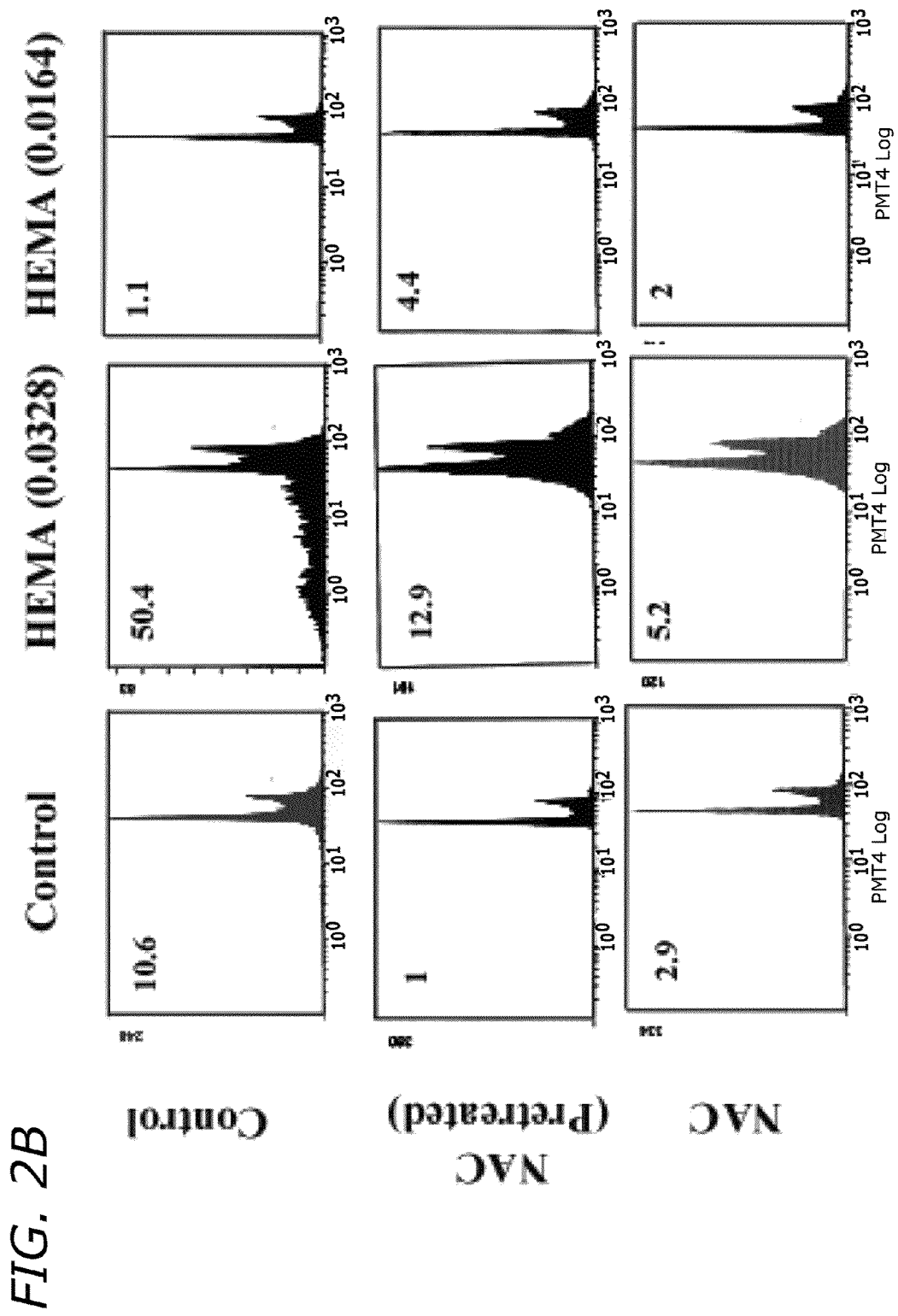

Following the establishment of HEMA-mediated apoptosis, RAW 264.7 cells and THP-1 cells were treated with 0.0328M, 0.0082M or 0.0164M HEMA in the presence and absence of NAC (20 mM). In this study, cells were pretreated with NAC for about 8 hours prior to the addition of HEMA (FIGS. 2A and 2B second panel down) or were simultaneously treated with NAC and HEMA (FIGS. 2A and 2B third panel down). After an overnight incubation, the levels of cell death were determined using PI staining of ethanol fixed cells. Specifically, cells were washed twice with PBS before they were treated with 70% ethanol (250 µl). Ethanol was added dropwise and then the cells were incubated on ice for 30 minutes. The cells were then washed twice with PBS and resuspended in 1 ml PBS to which PI at a final concentration of 1 mg/ml was added. The samples were then analyzed using the flow cytometer.

In FIGS. 2A and 2B, the numbers in each histogram represent the percentage of Sub Go/G1 fragmented cell populations. Ten thousand events were analyzed for each sample. As can be seen in FIGS. 2A and 2B, NAC inhibited HEMA-mediated cell death in murine (RAW 264.7) and human (THP-1) macrophage cell lines.

Figure 3:
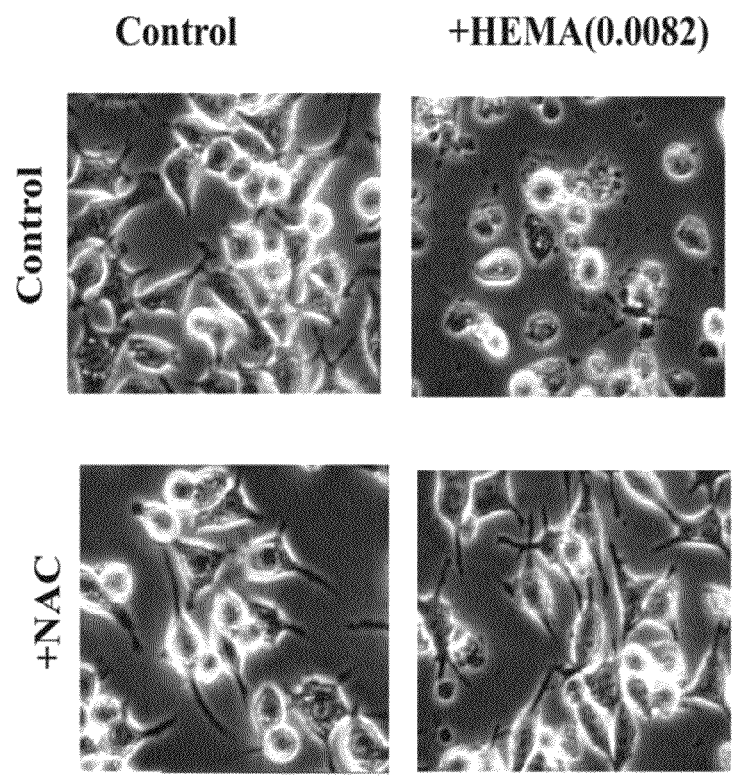
FIG. 3 shows NAC's ability to inhibit HEMA-mediated morphological changes in RAW 264.7 cells.

To determine whether inhibition of apoptotic cell death resulted in the survival and increased viability of HEMA-treated cells was also examined. Addition of HEMA to RAW 264.7 cells results in morphological changes indicative of apoptosis, namely decreased size, blebbing and formation of apoptotic bodies (FIG. 3). Simultaneous addition of NAC (20 mM) to HEMA-treated RAW 264.7 cells inhibited the occurrence of these morphological changes when cells were incubated overnight and photographs taken using an inverted microscope (Mag. 20×) (FIG. 3). These results further indicate that NAC inhibits adverse effects mediated by HEMA exposure.

2. Peripheral Blood Mononuclear Cells

Because NAC inhibited HEMA-mediated cell death and cytotoxicity in murine RAW 264.7 and human THP-1 macrophage cell lines and ameliorated morphological changes observed in RAW 264.7 cells, its ability to inhibit such apoptosis in other relevant cell types was also examined. For example, the ability of NAC to prevent HEMA-mediated cell death and cytotoxicity in peripheral blood mononuclear cells (PMBCs) was evaluated. PBMCs were isolated and obtained after Ficoll-hypaque centrifugation as described in Jewett et al., 159, J. Immunol. (1997) which is hereby incorporated by reference. Specifically, human peripheral blood was obtained from normal donors in the laboratory as per guidelines of the UCLA Human Subject Protection Committee. The blood was fractionated on Ficoll-Hypaque, and the buffy layer was harvested, washed and resuspended in media.

Peripheral blood mononuclear cells were then cultured in RPMI 1640 supplemented with 10% FCS, 1% penicillin-streptomycin, 1% sodium pyruvate and 1% non-essential amino acids.

Figure 4A:
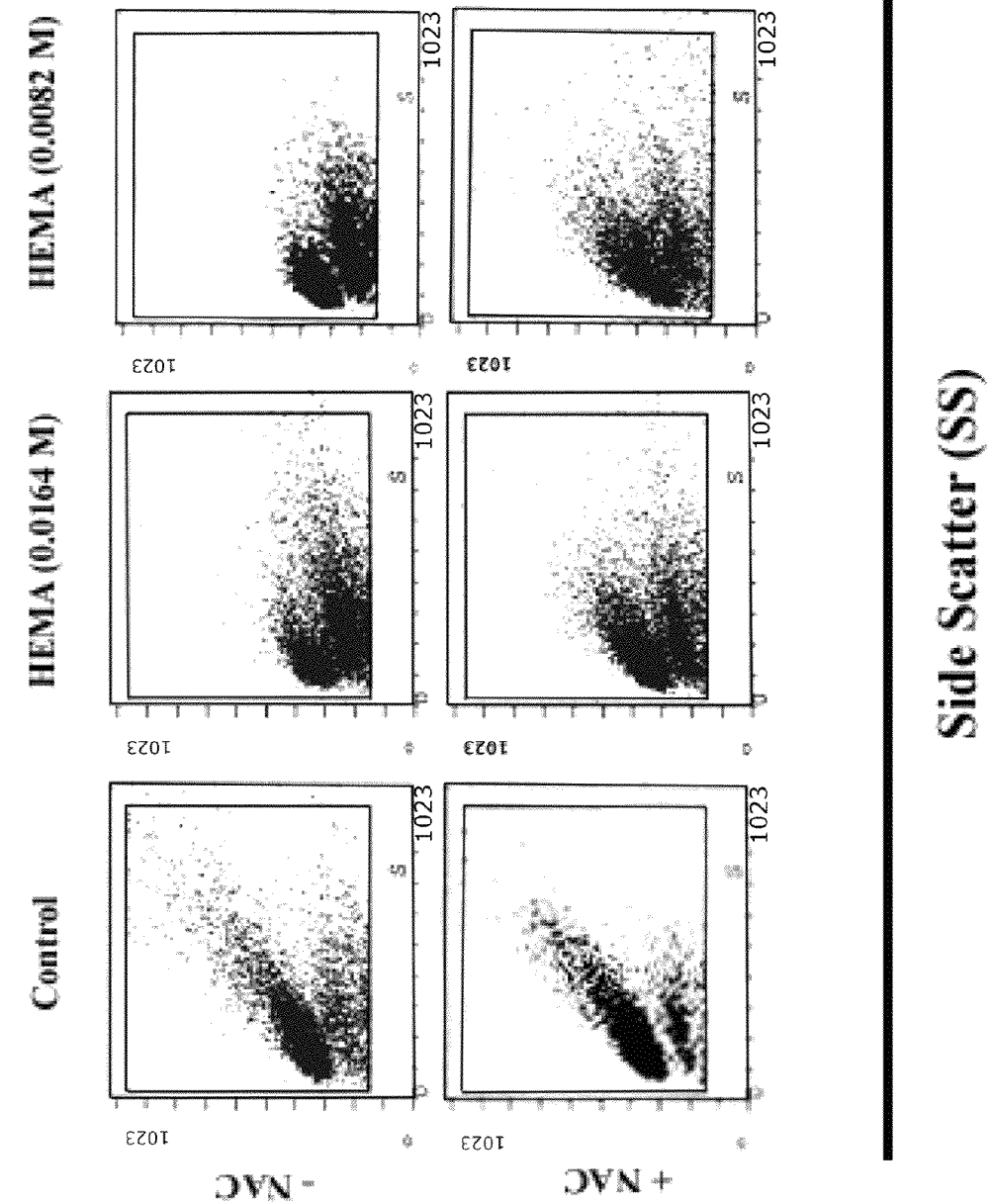
FIGS. 4A and 4B shows inhibition of HEMA-mediated cell death by NAC in peripheral blood mononuclear cells (PBMCs).
Figure 4B:
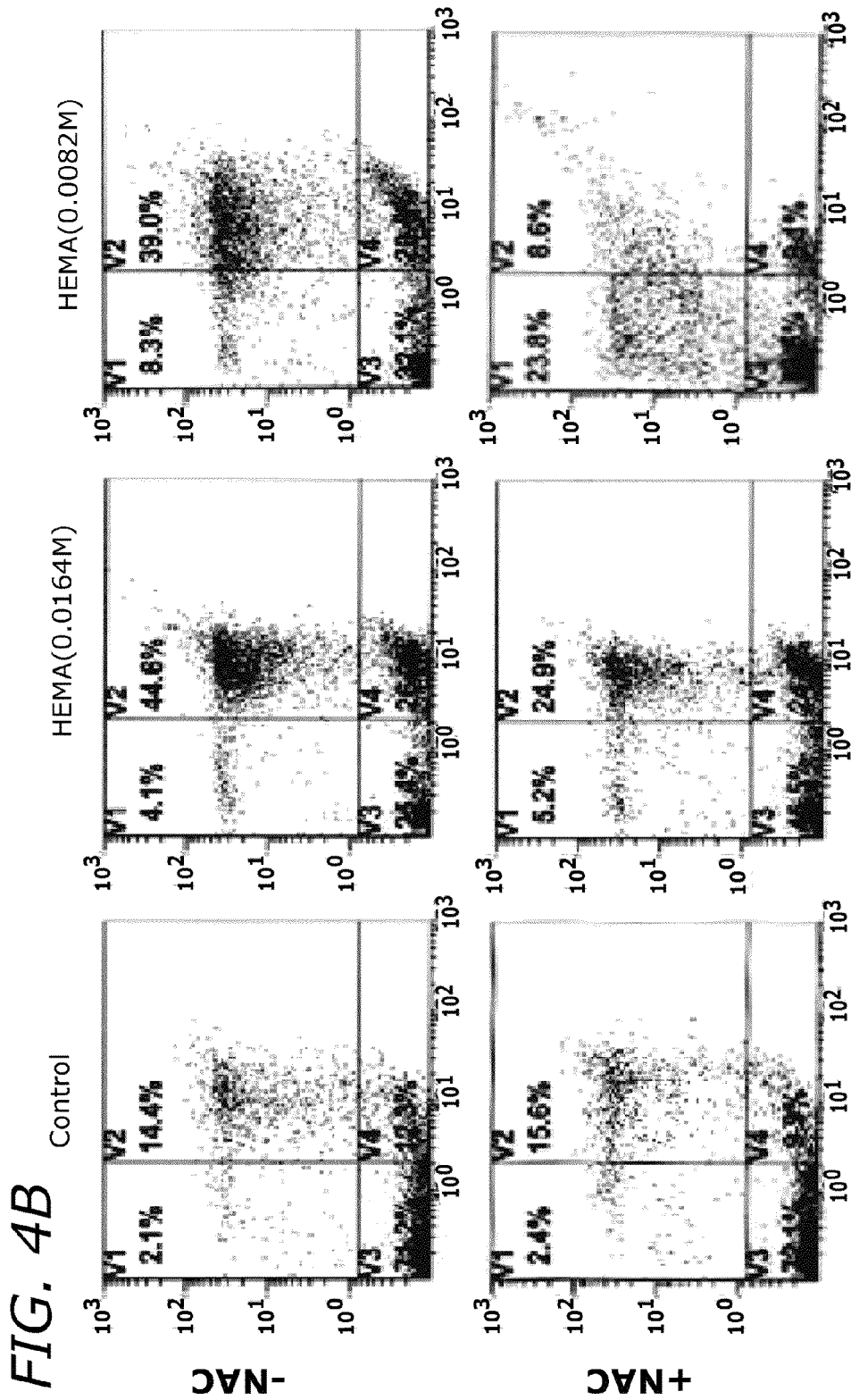

Cells were simultaneously treated in the presence and absence of NAC overnight. As can be seen in FIG. 4B, staining with PI/Annexin V showed that the numbers of HEMA-treated cells in the stage of late apoptosis decreased from about 45% to about 25% at 0.0164M concentration of HEMA and 39% to 8%-6% at a 0.0082M concentration of HEMA when cells were also treated with NAC. Furthermore, when analysis of Forward Angle Light Scatter (FS), which represents the size of the cells and Side Scatter (SS) representing the granularity of the cells was considered, a significant population of HEMA treated cells from a healthy individual had a distinct population with low FS and high SS (see FIG. 4A). Such a distinct subpopulation of the cells could not be seen in the untreated cells. It is quite well known that apoptotic cells initially lose their size and gain in granularity when they undergo cell death. These changes are one hallmark of apoptosis. However, a significant portion of the cells treated with HEMA and NAC showed a high forward angle light scatter and a low side scatter as could be seen which was comparable to the untreated cells.

In a subsequent study, the same treatments were carried out for IL-2 treated lymphocytes. IL-2 is a well known activator of lymphocyte function, so the effect of IL-2 activation on cell death profiles in PBMCs was examined and similar results were obtained.

3. Skin Keratinocytes

The ability of NAC to inhibit HEMA-mediated cell death and cytotoxicity in skin keratinocytes was also evaluated. HaCaT cells were obtained from ATCC and were cultured in a 5% $CO_2$ atmosphere in DMEM containing 10% FCS, 1% penicillin-streptomycin, 1% sodium pyruvate, 1% non-essential amino acids and 1% glutamine. HaCaT cells were then simultaneously treated with different concentrations of HEMA from 0.082M to 0.00164M and NAC (20 mM). After an overnight incubation, the levels of cell death were determined using dual staining with PI/Annexin V. The numbers in each quadrant represent the percentages of cells positive in that quadrant. Ten thousand events were analyzed for each sample. (FIG. 5)

Figure 5:
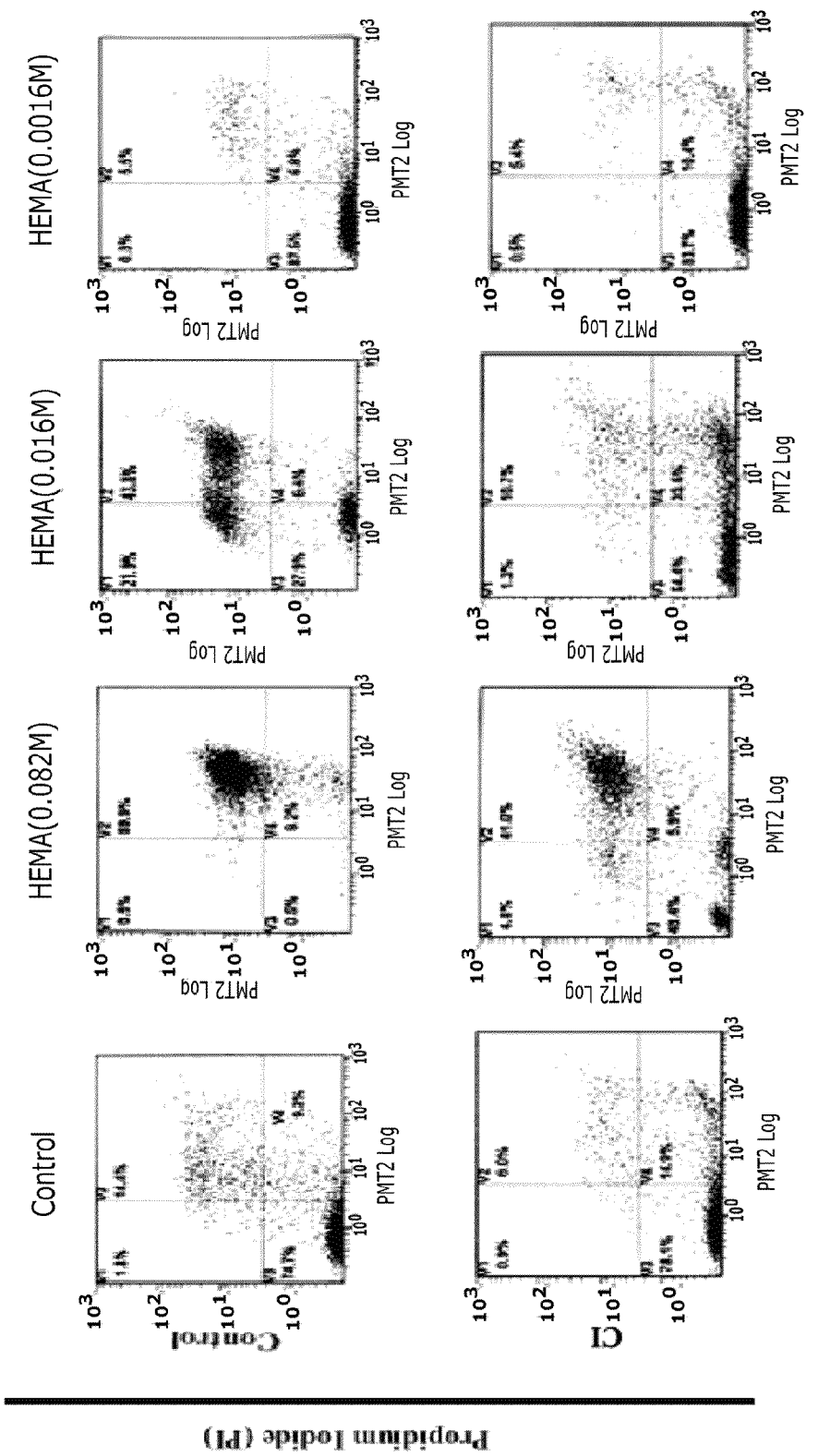
FIG. 5 shows inhibition of HEMA-mediated cell death by NAC in skin keratinocytes.

As can be seen in FIG. 5, dose dependent induction of apoptotic cell death was evident when HaCaT cells were treated with HEMA. At higher concentrations of HEMA, the majority of the cells were at later stages of apoptosis, whereas at lower concentrations both necrotic and apoptotic cell death could be observed. Treatment with NAC considerably decreased the percentages of cells positive for PI/Annexin V staining after HEMA treatment showing that NAC inhibits HEMA-mediated cell death and cytotoxicity.

4. Dental Pulp Stromal Cells

Figure 6:
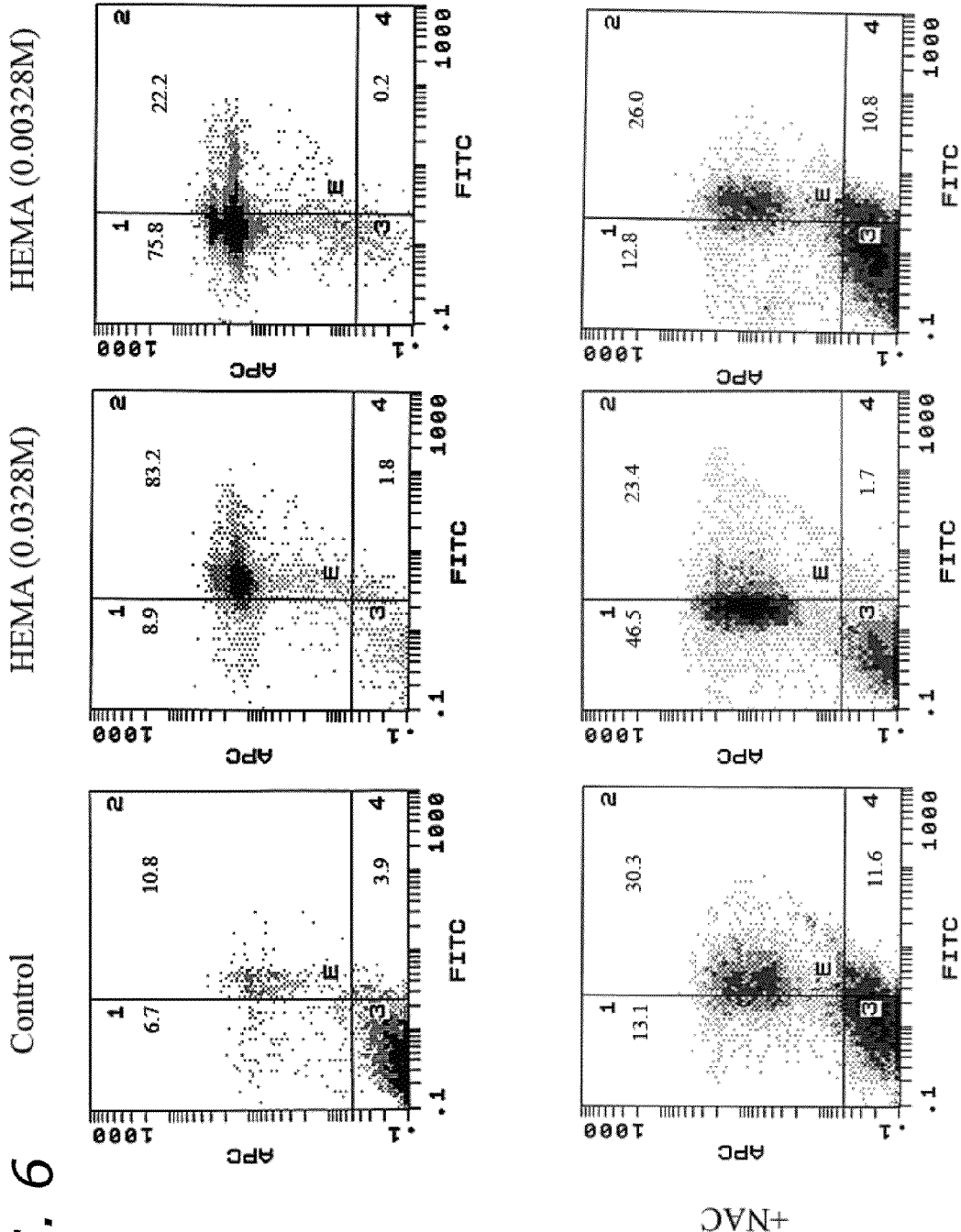
FIGS. 6-12 show inhibition of HEMA-mediated cell death by NAC in both rat (FIGS. 6-10) and human (FIGS. 11 and 12) dental pulp stromal cells.

The ability of NAC to inhibit HEMA-mediated cell death and cytotoxicity was next evaluated in dental pulp stromal cells. In a first study using dental pulp stromal cells, dental pulp tissue was extracted from the lower central incisors of 8-12 week old male Sprague-Dawley rats. The lower central incisors were carefully extracted without fracture to avoid periodontal tissue influx into the pulp tissue. The periodontal tissue and other soft tissue remnants were removed from the root part of the teeth, and the incisor tip and root parts were then cut to allow the pulp tissue to be washed out. The extracted tissue was then treated with 0.1% collagenase in 0.25% trypsin EDTA at 37° C. for about 15 minutes. The pellet of released cells was then centrifuged at about 2000 rpm for about 4 minutes and resuspended in DMEM supplemented with 10% FBS, 1% sodium pyruvate, 1% non-essential amino acids and 1% antibiotic-antimycotic. The cells were cultured in a 6 well plate and the media was changed every 3 days. The cells were then treated simultaneously with 0.0328M and 0.00328M HEMA and NAC (20 mM) for about 12-14 hours. As can be seen from FIG. 6, inclusion of NAC during HEMA exposure resulted in a higher number of viable cells (quadrants 3) as compared to the cells treated with HEMA alone. These results further indicate that HEMA induces cell death and that NAC is an effective inhibitor of HEMA-mediated cell death and cytotoxicity.

In a second study using dental pulp stromal cells, 8 week old male Sprague Dawley rats were divided into the following groups: (1) control; (2) cavity preparation only; (3) cavity preparation with pulpal exposure; (4) cavity preparation and restored with composite resin only; (5) cavity preparation and restoration with HEMA and NAC; (6) cavity preparation and exposure; (7) cavity preparation and exposure and restored with composite resin and NAC.

The teeth used for this experiment were the upper and lower incisors. Restorations were placed on the teeth for about 5 hours after which the teeth were extracted and cells plated in culture dishes. The cell culture media was changed every 3 days and the number of cells per condition were counted after three weeks.

The results demonstrated the following number of cells per group (Table 1).

TABLE 1

| Group | Number of Cells |
| --- | --- |
| Control | $8.0 \times 10^4$ |
| Cavity preparation only | $6.4 \times 10^4$ |
| Cavity preparation with pulpal exposure | $2.0 \times 10^4$ |

TABLE 1-continued

| Group | Number of Cells |
| --- | --- |
| Cavity preparation and restored with composite resin only | $0.8 \times 10^4$ |
| Cavity preparation and restoration with HEMA and NAC | $6.0 \times 10^4$ |
| Cavity preparation and exposure | $1.6 \times 10^4$ |
| Cavity preparation and exposure and restored with composite resin and NAC | $1.6 \times 10^4$ |

Thus, these data demonstrate that NAC can help to prevent cell death associated with HEMA and composite resins.

In a next experiment, the incisors of nine eight-week-old male rats were prepared with class V preparations near the level of the gingival using a #1 round bur in a high speed dental handpiece. The preparation was approximately ½ mm deep (half the depth of the bur) and did not violate the pulp space. The animals were then divided into three groups in order to compare the number of functional cells in pulp extracted from the lining of the rat teeth: (1) no restorative materials; (2) composite resin restorative material (Herculite XR, Kerr) with dentin bonding agent (ProBOND, DENTSPLY) applied; and (3) restorative materials in combination with NAC applied.

Again, in this experiment upper and lower incisors were used. Restorative materials were placed on the teeth for about 5 hours. The pulp was extracted and treated with trypsin/EDTA (0.25%) and collagenase (0.02%), washed and resuspended in DMEM containing β-glycerophosphate (10 mM) and ascorbic acid (50 µg/ml) and allowed to grow to confluency. After 14 days of cell growth (media changed every 2-3 days) photographs were taken using an inverted microscope; cells were detached and counted in each experimental group; and wells containing different experimental groups were stained for alkaline phosphatase (ALP).

Figure 7A:
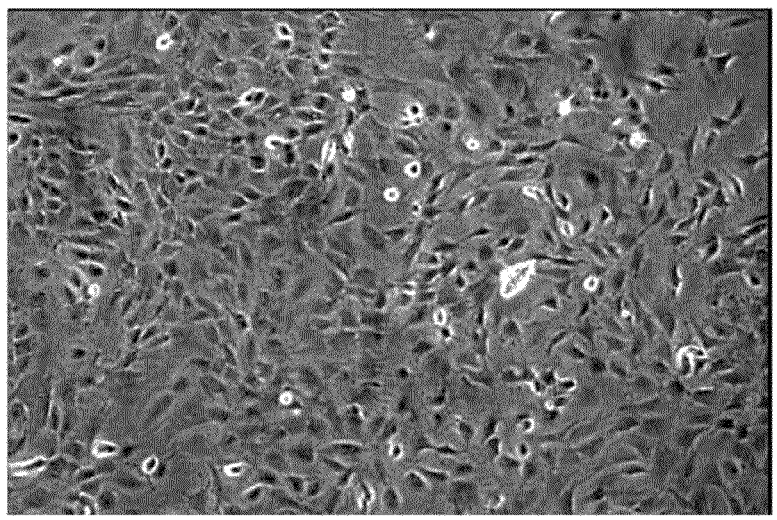
Figure 7B:
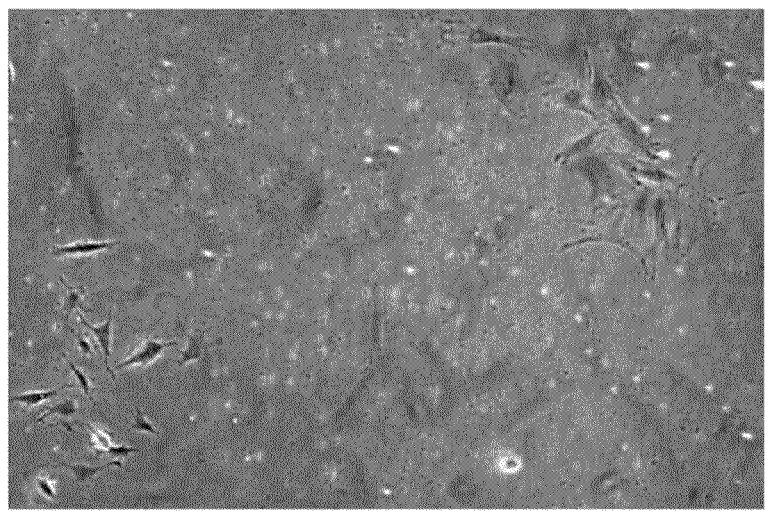
Figure 7C:
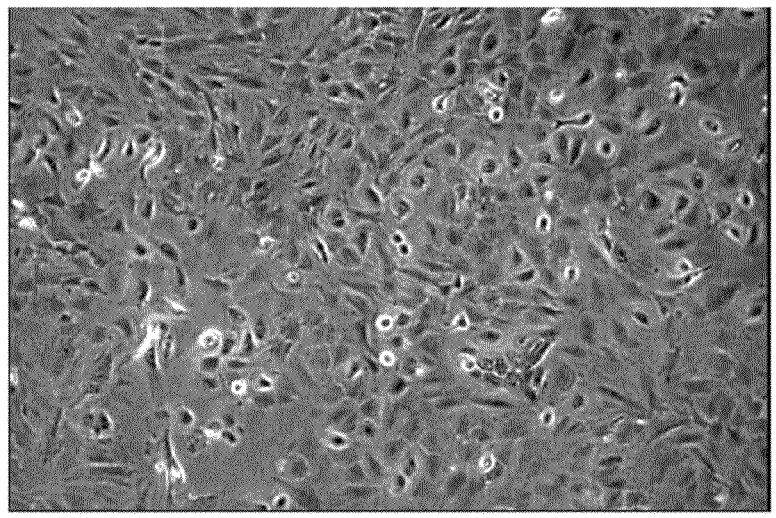
Figure 8:
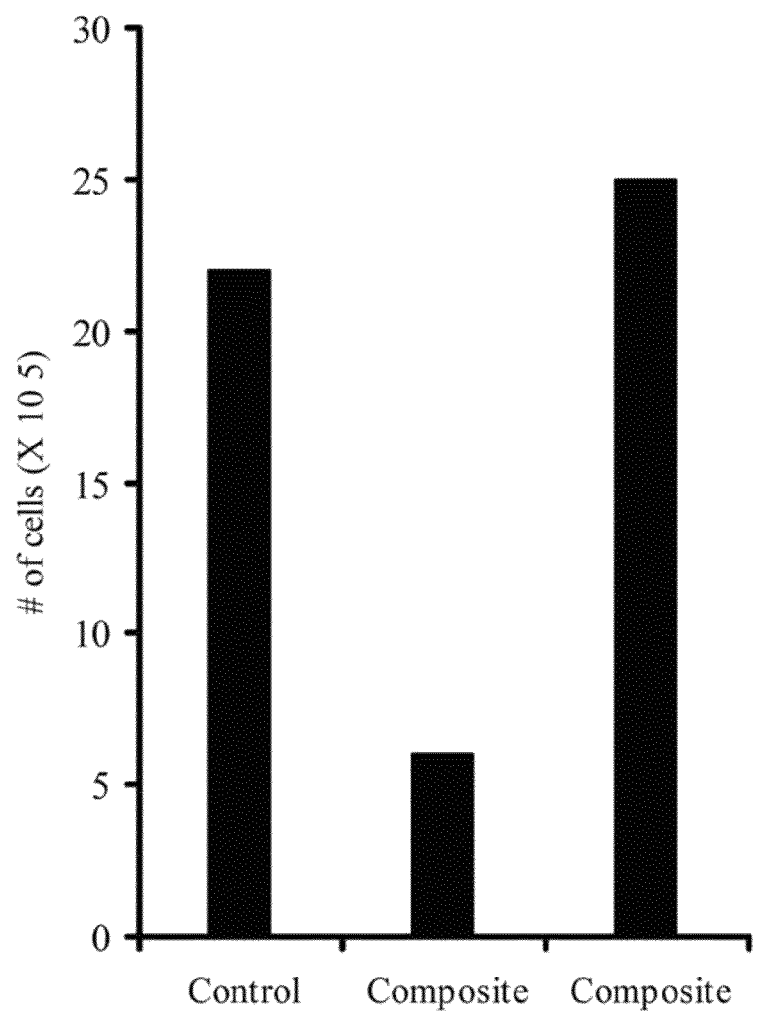
Figure 9:
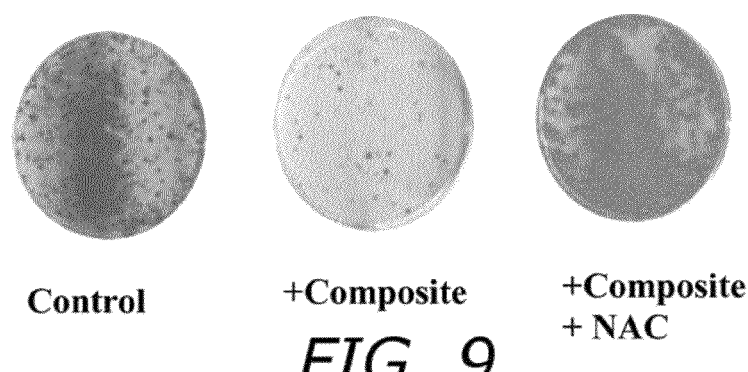

FIGS. 7-9 show the results of these studies. The top left panel of FIG. 7 shows cells from the first group where no restorative materials were used. The top right panel shows cell loss following the use of the composite resin restorative material, Herculite XR with dentin bonding agent. The bottom panel shows that NAC can help to prevent the cell loss associated with the use of composite resin restorative materials. FIG. 8 shows the results depicted in FIG. 7 in graphical form. Again, FIG. 8 shows that NAC can help to prevent the cell loss associated with the use of composite resin restorative materials. FIG. 9 shows wells containing different experimental groups stained for ALP. As can be seen in this group, the negative effects of the use of the composite resin restorative materials can be ameliorated with the use of NAC.

Figure 10:
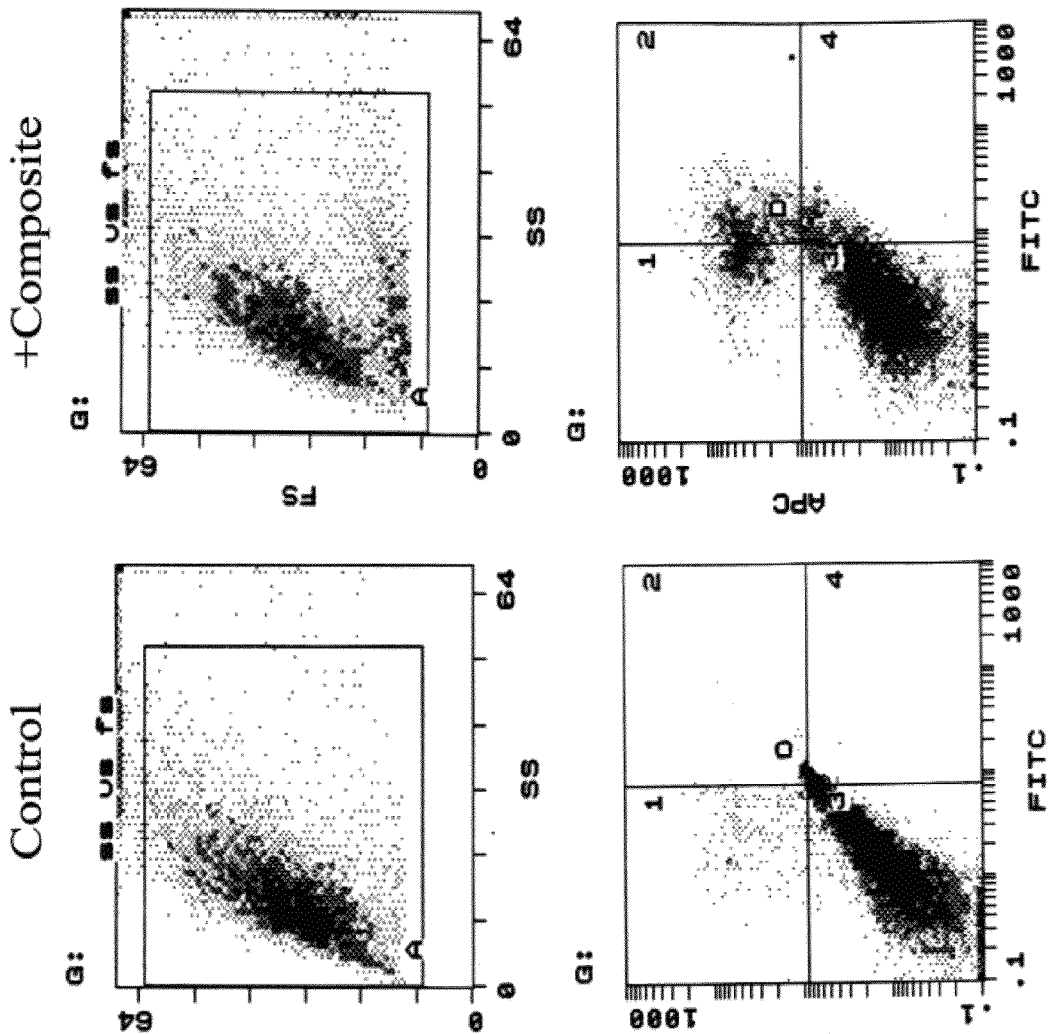

In another study, an in vitro method was used to test the effects of routinely used composite resins (Bisco Light-Core) on dental pulp stromal cells. In this study, pulp was again extracted and treated with trypsin/EDTA (0.25%) and collagenase (0.02%) to obtain a single cell suspension of the cells, washed and resuspended in DMEM containing β-glycerophosphate (10 mM) and ascorbic acid (50 µg/ml), and allowed to grow to confluency. Composite discs were placed on the dental pulp stromal cells for 7 days after which the cells were stained with FITC-Annexin V and PI and analyzed by flow cytometry. The top panel of FIG. 10 represents the FS (size) and SS (granularity). Note that cells which had undergone cell death demonstrate smaller size and high granularity, a hallmark of apoptosis. The lower panel of FIG. 10 represents staining with FITC-Annexin V and PI.

Figure 11:
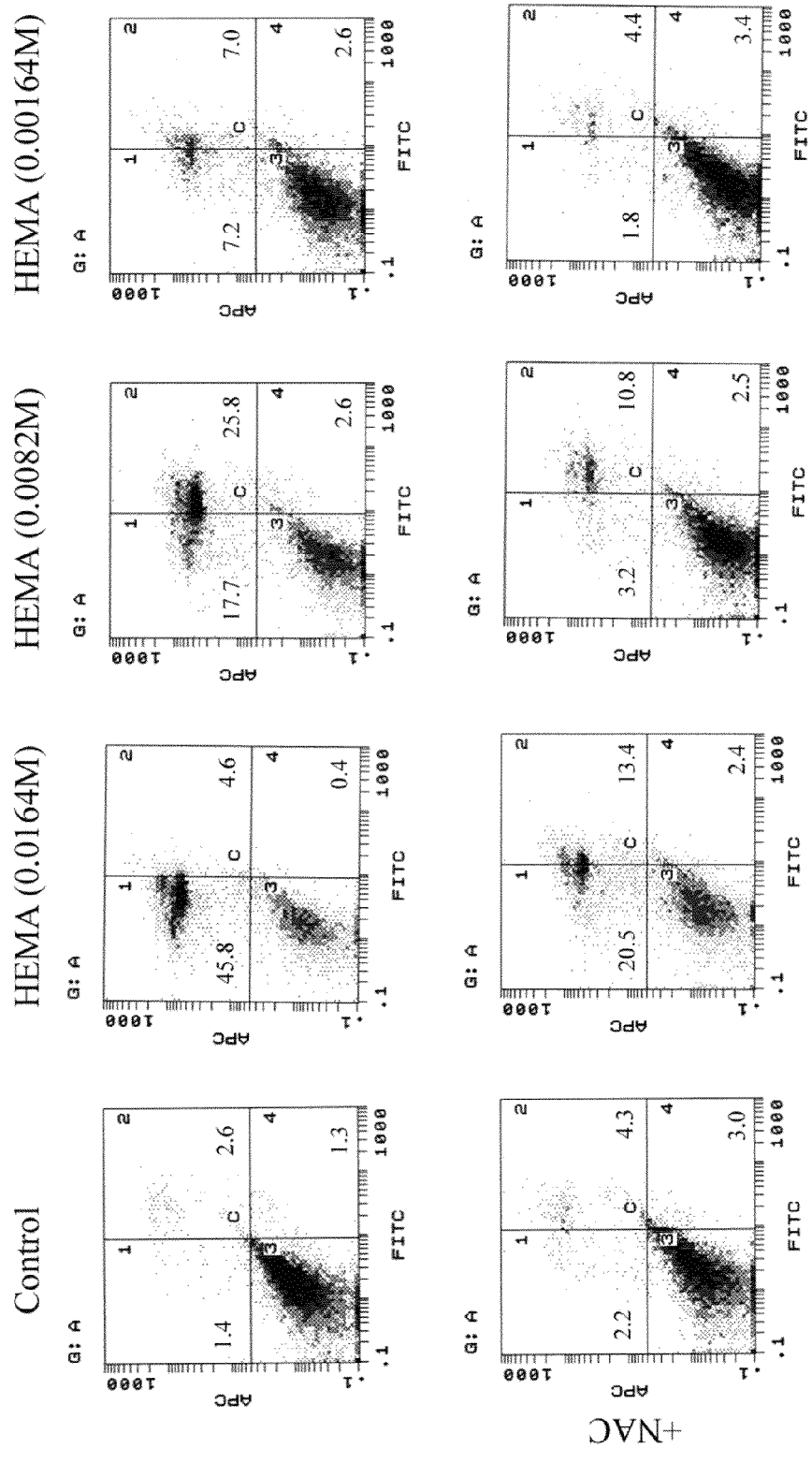

Next, in order to directly assess the effect of HEMA on human dental pulp stromal cells, human molars were cracked after therapeutic extraction. Pulp was then removed, minced and treated with trypsin/EDTA and collagenase to release the dental pulp stromal cells. Cells were then grown in media containing β-glycerophosphate and ascorbic acid until they reached confluency, after which the cells were detached and treated with HEMA (in the concentrations described above) and NAC (20 mM) for a period of 18 hours. Next the cells were analyzed for apoptosis using FTIC-Annexin V and PI. FIG. 11 shows that significant inhibition of HEMA-mediated cell death at all HEMA concentrations occurred in the presence of NAC in human dental pulp stromal cells.

Figure 12:
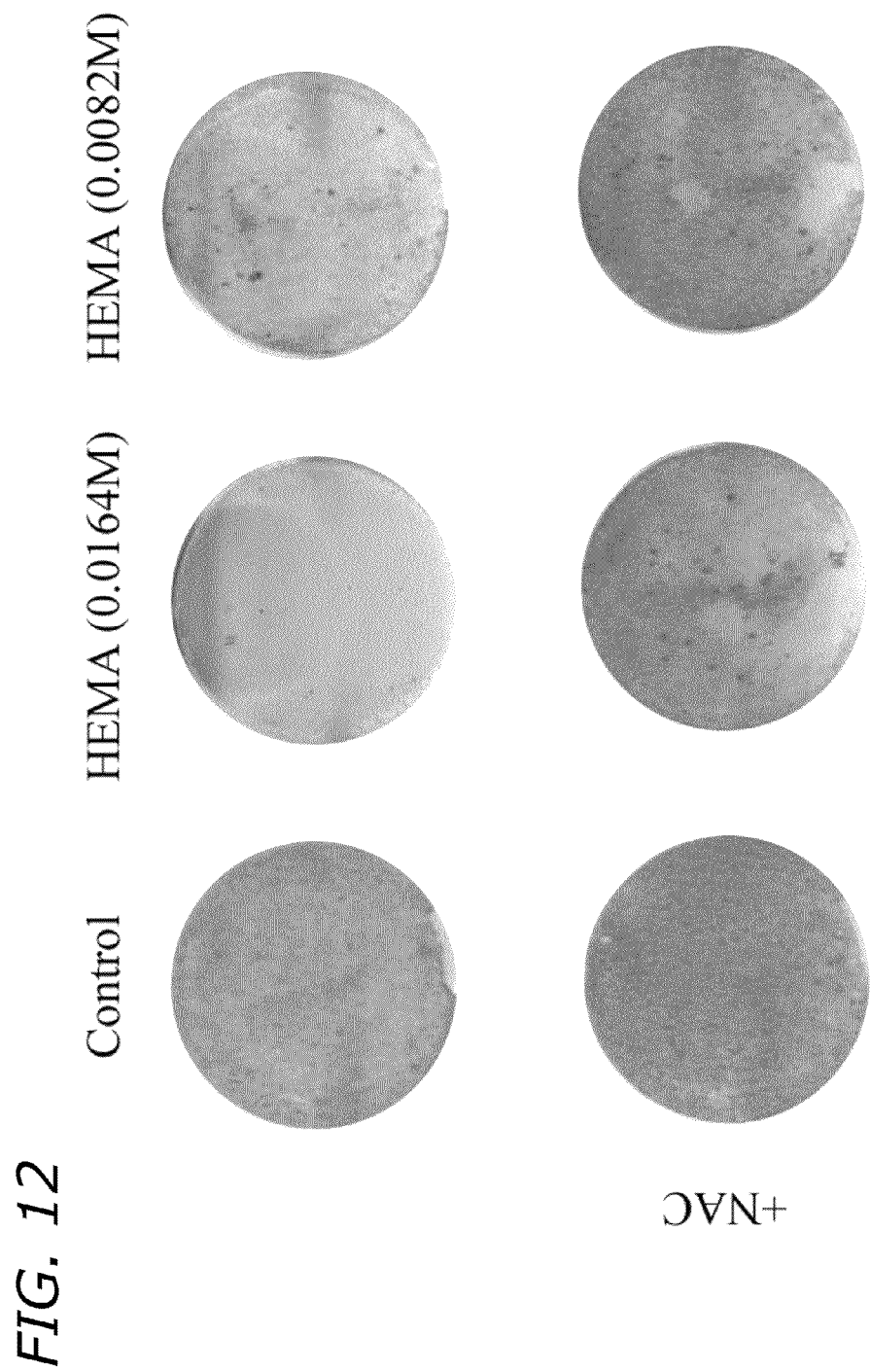

Following the experiment described above in human dental pulp stromal cells, treatments were carried out as described above with the levels of ALP staining representing maturation/differentiation of dental pulp stromal cells. This staining was performed after 7 days of incubation. As can be seen in FIG. 12, HEMA-mediated decrease in ALP was significantly prevented in the presence of NAC.

5. Odontoblasts

Figure 13:
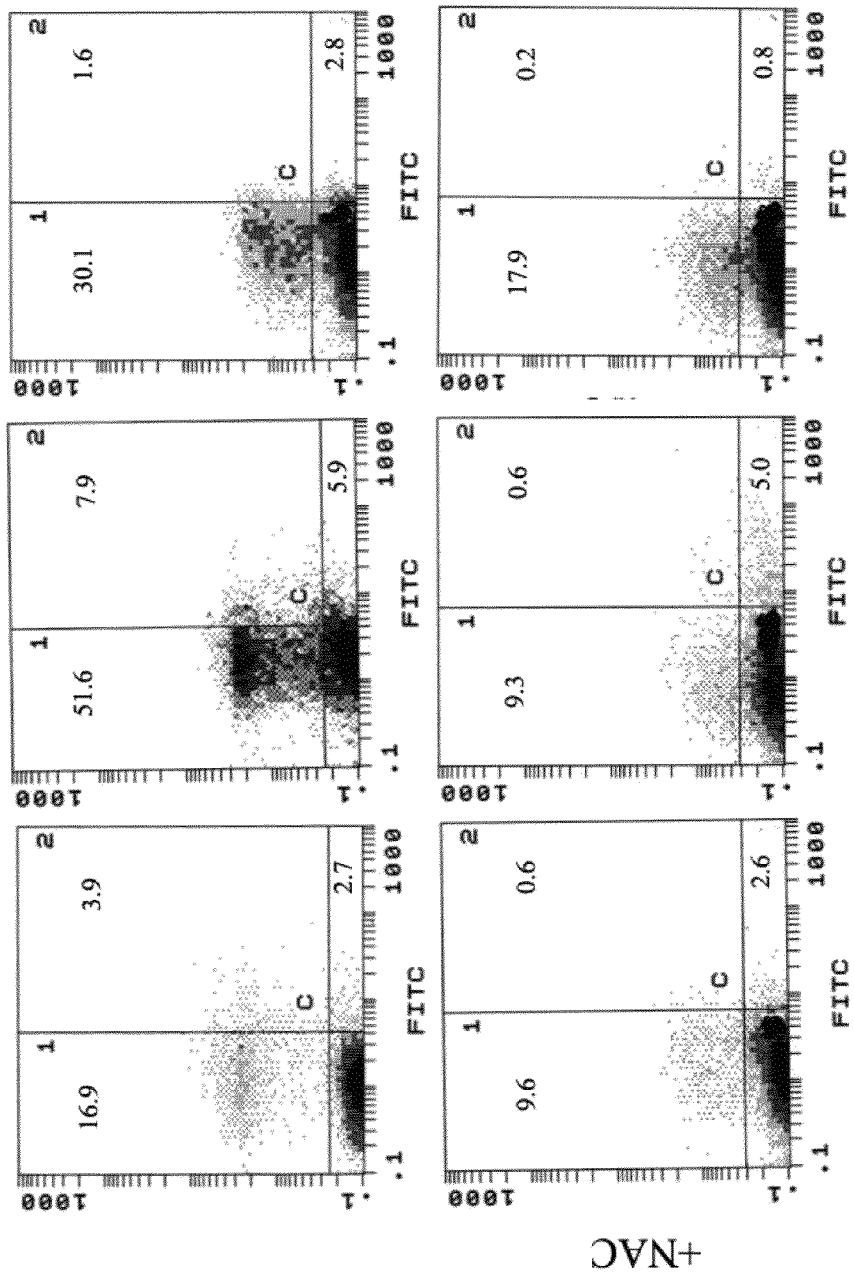
FIG. 13 shows inhibition of HEMA-mediated cell death by NAC in odontoblasts.

Following the above-described experiments, rat dental pulp stromal cells were differentiated into odontoblasts to evaluate the ability of NAC to inhibit HEMA-mediated cell death and cytotoxicity in this cell type. Differentiation was induced by the addition of about 10 mM of β-glycerophosphate and about 50 µg/ml of ascorbic acid. Following differentiation, odontoblasts were treated with 0.0164M-0.00164M of HEMA alone or HEMA and NAC (20 mM) simultaneously for about 12-14 hours. FIG. 13 shows that when odontoblasts are treated with NAC and HEMA, the percentage of viable cells increases (quadrant 3) when compared to HEMA alone-treated cells.

The preceding experiment demonstrated that NAC is an effective compound to inhibit HEMA-mediated cell death and cytotoxicity. Restoring the function of cells is also very important. Therefore, ALP staining was performed as a measure of odontoblast function. Specifically, rat odontoblasts were treated with 0.00328M HEMA for time periods of overnight, 7 days or 14 days. Following this incubation, cells were washed twice with PBS and incubated with 120 mM of Tris buffer (pH=8.4) containing 0.9 mM Napthol AS-M Phosphate and 1.8 mM Fast Red TR for 30 minutes at 37° C. Afterwards the cells were washed three times with PBS and then fixed with 1 ml cold ethanol (100%) for about 30 minutes. The stained cultures were digitized using a scanner.

Figure 14:
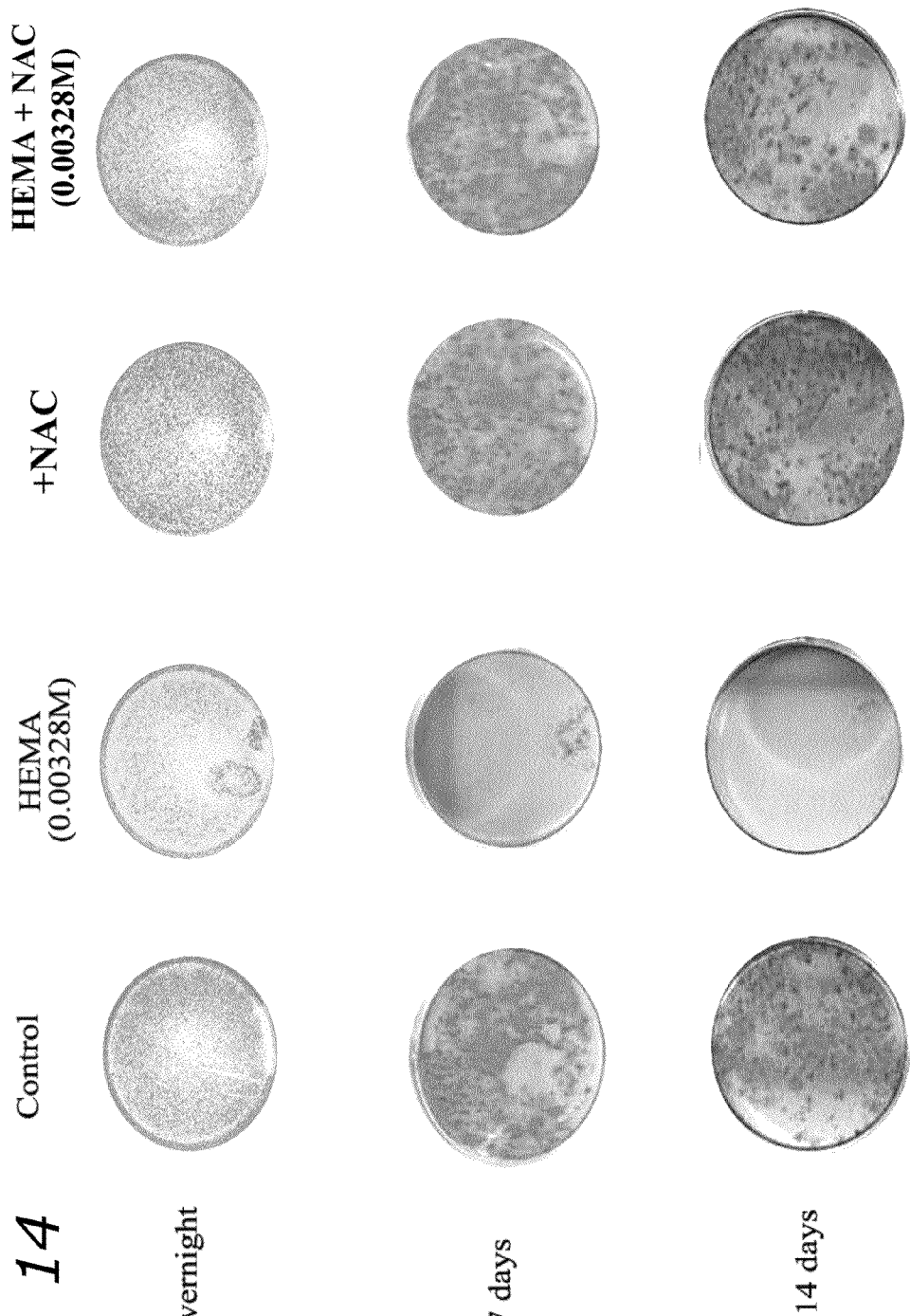
FIG. 14 shows that NAC can help preserve cell function in the presence of HEMA in odontoblasts.

As can be seen in FIG. 14, cells treated with NAC as well as NAC and HEMA were positive for ALP staining. Cells treated with HEMA alone showed significantly less staining, demonstrating that in addition to inhibiting HEMA-mediated apoptosis, NAC is also effective at preserving cell function.

6. Gingival Cells

The ability of NAC to inhibit HEMA-mediated cell death and cytotoxicity in rat gingival cells was also examined. The ability of NAC to inhibit HEMA-mediated cell death and cytotoxicity is important in gingival cells because this tissue is also likely to come into contact with resin-based restorative materials. Rat gingival cells were obtained from 8 week old male rats and cultured in DMEM supplemented with 10% FBS, 1% antibiotic-antimycotic, 1% sodium pyruvate and 1% non-essential amino acids. The rat gingival cells were treated with different concentrations of HEMA from 0.0164M-0.00164M HEMA and NAC (20 mM) simultaneously and incubated for about 12-14 hours. Cell survival was measured by PI/FITC-Annexin V staining as described previously.

Figure 15:
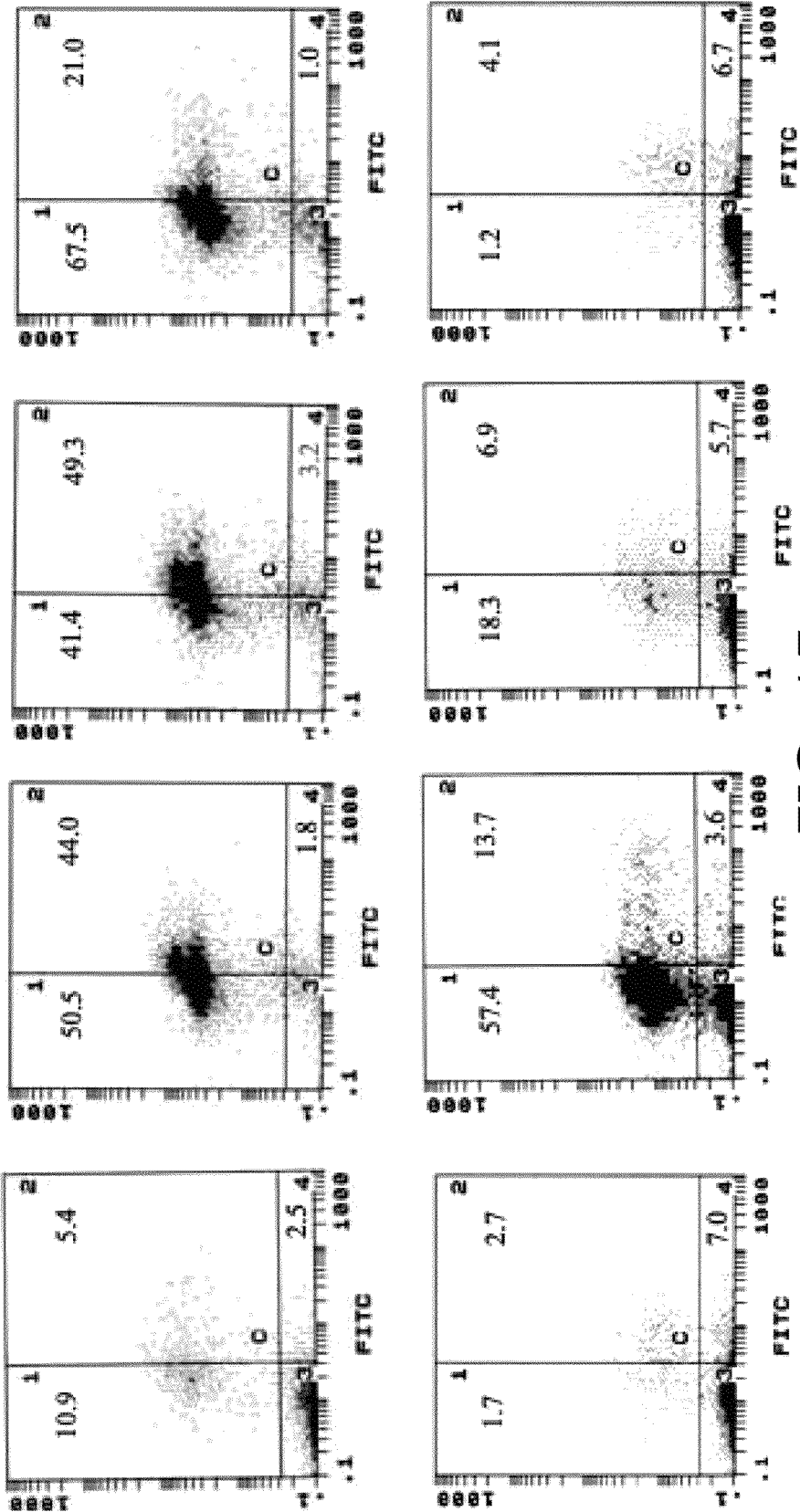
FIG. 15 shows inhibition of HEMA-mediated cell death by NAC in gingival cells.

As can be seen in FIG. 15, similar results were obtained in rat gingival cells as were obtained with rat odontoblasts. NAC led to a higher number of viable cells (quadrant 3) after HEMA exposure when compared to HEMA alone-treated cells.

Treatment with NAC inhibits HEMA-mediated cell death and cytotoxicity. Thus, its ability to protect the function of cells in the presence of HEMA was also evaluated further. HEMA treatment has a significant inhibitory effect on the secretion of VEGF in the presence of immune effector cells and HEp2 cells. As a result, the ability of NAC to block this decrease was evaluated, specifically whether the treatment of HEp2 cells with NAC would block the decrease in VEGF secretion during the interaction of immune effector cells with HEMA treated HEp2 cells.

HEp-2 cells obtained from ATCC were cultured in DMEM supplemented with 10% FBS, 1% sodium pyruvate, 1% non essential amino acids and 1% antibiotic-antimycotic solution. HEp-2 cells were treated either with different concentrations of HEMA (from 0.0164M-0.00082M) alone or with HEMA and NAC (20 mM) for about 18 hours. The cells were trypsinized and washed 4 times with 1×PBS before they were co-cultured with PBMCs obtained from a healthy individual. A 4:1 ratio of effector to target cells (PBMC:HEp2) were used in these cultures. PBMCs were treated with and without IL-2 before they were co-cultured with HEp-2 cells. The supernatants were then removed from the co-cultures after an overnight incubation and analyzed using the FAST QUANT multiplex cytokine array kit to determine the levels of secreted cytokines.

The results presented in Table 2 indicate that NAC inhibits HEMA-mediated decreases in VEGF production:

TABLE 2

| HEp2 | VEGF | | | | |
| --- | --- | --- | --- | --- | --- |
| | Patient | | Control | | |
| −/+HEMA (M), −/+NAC | PBMC −IL-2 | PBMC +IL-2 | PBMC −IL-2 | PBMC +IL-2 | No PBMC |
| — | 242 | 225 | 535 | 411 | — |
| −HEMA (−NAC) | 7649 | 7615 | 6274 | 8260 | 6772 |
| +0.0164M HEMA (−NAC) | 1161 | 379 | 582 | 323 | 294 |
| +0.00164M HEMA (−NAC) | 6550 | 7760 | 6640 | 6923 | 7139 |
| −HEMA (+NAC) | 5648 | 5805 | 5260 | 5376 | 4714 |
| +0.0164M HEMA (+NAC) | 3235 | 4208 | 2950 | 3630 | 2325 |
| +0.00164M HEMA (+NAC) | 4572 | 4383 | 4110 | 5092 | 2445 |

Differences can also be observed when IL-6 is measured in the co-cultures of NAC treated HEp2 cells and immune effector cells in healthy donor PBMCs (Table 3).

TABLE 3

| HEp2 −/+HEMA (M), −/+NAC | PBMC −IL-2 | IL-6 pg/ml | PBMC +IL-2 | IL-6 pg/ml |
| --- | --- | --- | --- | --- |
| — | − | 151 | + | 251.4 |
| −HEMA (−NAC) | − | 1062 | + | 1657 |
| +0.0164M HEMA (−NAC) | − | 191 | + | 262 |
| +0.0082M HEMA (−NAC) | − | 192 | + | 243 |
| +0.00164M HEMA (−NAC) | − | 208 | + | 264 |
| +0.00082M HEMA (−NAC) | − | 204 | + | 371 |
| −HEMA (+NAC) | − | 880 | + | 1835 |
| +0.0164M HEMA (+NAC) | − | 172 | + | 426 |
| +0.0082M HEMA (+NAC) | − | 285 | + | 555 |
| +0.00164M HEMA (+NAC) | − | 430 | + | 794 |
| +0.00082M HEMA (+NAC) | − | 746 | + | 1650 |

These results demonstrate a decrease inhibition of IL-6 secretion in untreated PBMCs co-cultured in the presence of HEMA treated HEp2 cells when compared to healthy controls. Thus, it seems at least in the case of IL-6, patient PBMCs are at functionally heightened levels. Indeed, in all of the experiments performed, patients' untreated PBMCs co-cultured in the presence of HEp2 cells (0.0164M HEMA) secreted IL-6 at the levels which were seen when healthy donor PBMCs were activated in the presence of IL-2. NAC also prevents HEMA-induced loss of proliferation in IL-2 treated PBMCs. Thus, NAC not only inhibits HEMA-mediated cell death and morphological changes but also helps to protect or restore the function of HEp2 cells in the presence of HEMA.

Figure 16:
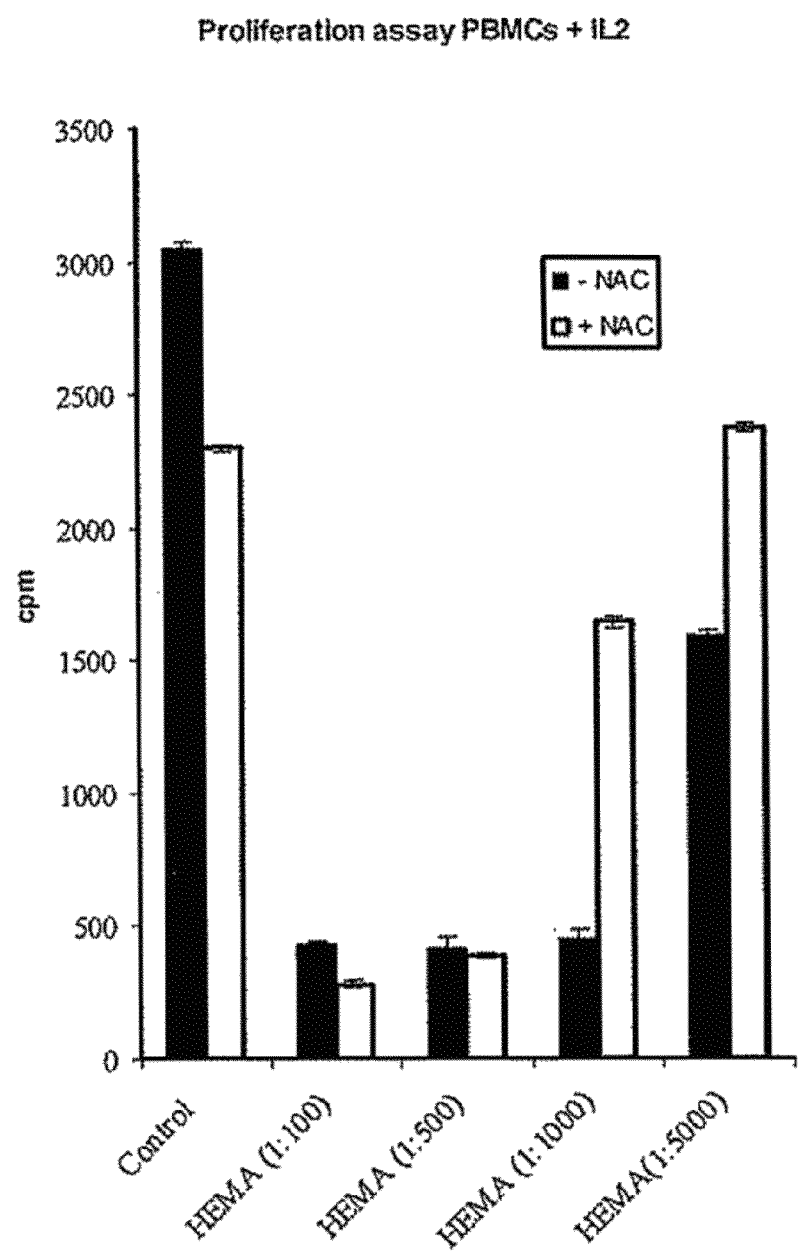
FIG. 16 shows that NAC prevents HEMA-induced loss of proliferation in IL-2 treated PMBCs.

Proliferation assays were also done with IL-2 treated PBMCs in the presence and absence of HEMA and NAC. Tritiated thymidine was added to the cells and after 24 hours of incubation assessed for proliferation. As can be seen in FIG. 16, NAC can prevent HEMA-induced loss of proliferation in IL-2 treated PBMCs.

Again, in order to examine the effect of HEMA on human dental pulp stromal cells, human molars were cracked after therapeutic extraction, and the pulp was removed and minced and treated with trypsin/EDTA and collagenase to release dental pulp stromal cells. The cells were then grown in media containing β-glycerophosphate and ascorbic acid until they reached confluency. Cells were next treated with HEMA and/or NAC as described in Table 4 with UCLA-2 cells (a primary oral tumor line) used as a control. Supernatants were measured for VEGF release. As can been seen in Table 4, VEGF levels decrease in the presence of HEMA and NAC helps to prevent this HEMA mediated decrease:

TABLE 4

| | Human dental pulp stromal cells (VEFG secretion (pg/ml) | UCLA-2 (VEFG secretion (pg/ml) |
| --- | --- | --- |
| Control | 2263.9 | 3195.7 |
| HEMA (0.0164M) | 113.4 | 180.2 |
| HEMA (0.0082M) | 125.1 | 319.6 |
| HEMA (0.00164M) | 163.7 | 3258.8 |
| NAC | 1804.1 | 2831.9 |
| NAC + HEMA (0.0164M) | 1060.4 | 2024.3 |
| NAC + HEMA (0.0082M) | 1719.0 | 3352.0 |
| NAC + HEMA (0.00164M) | 2490.6 | 1773.8 |

Figure 17A:
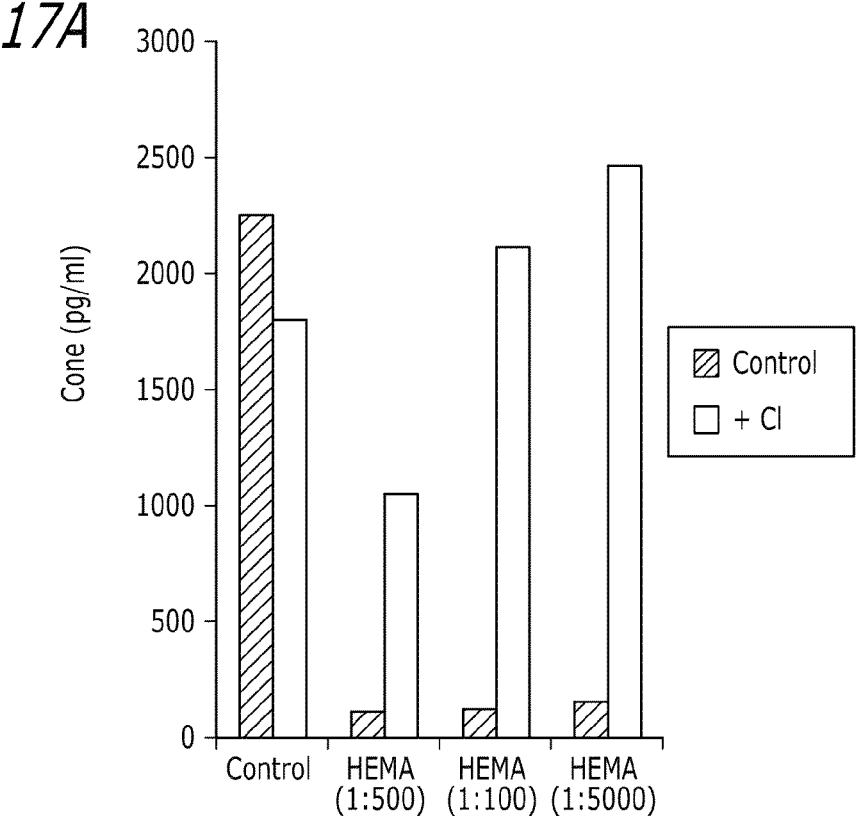
FIGS. 17A and 17B show the release of VEGF (FIG. 17A) and cell death (FIG. 17B) following HEMA and NAC exposure.
Figure 17B:
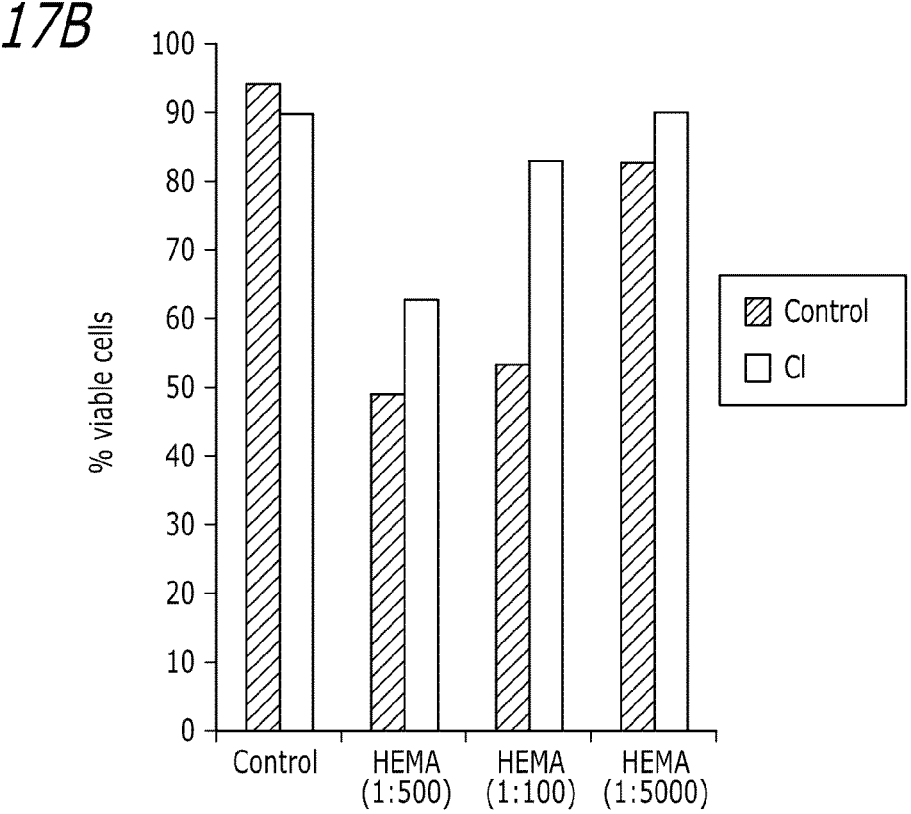

In order to further assess the effect of HEMA on human dental pulp stromal cells, human molars were treated as described above. After cells reached confluency, cells were detached and treated with HEMA and NAC (20 mM) for a period of 4 hours. After this treatment cells were washed and incubated overnight. After the overnight incubation, supernatants were assayed for VEGF secretion using an ELISA and cells were analyzed for apoptosis using FTIC-Annexin V and PI As can be seen in FIGS. 17A and 17B, HEMA has large effects on both VEGF secretion and cell death. These effects can also be strongly if not totally ameliorated by the presence of NAC.

B. Studies Evaluating the Mechanism of HEMA-Induced Cell Death and Cytotoxicity and NAC's Ability to Inhibit these Effects Most of the morphological changes induced by apoptosis are brought about by activated caspases. Induction of apoptosis is initiated by two distinct pathways known as the intrinsic pathway mediated by mitochondria and the extrinsic pathway mediated by death receptors. These two pathways are not mutually exclusive because at certain points in the process, the pathways can cross over and contribute to the speed and intensity of cell death. In addition to mitochondrial damage and receptor mediated cell death, alterations in $Ca^{2+}$ homeostasis, and accumulation of misfolded protein in the endoplasmic reticulum (ER) can cause cellular stress resulting in the initiation of apoptotic cell death. Therefore, the ER is known as another subcellular compartment in cells implicated in the execution of apoptosis signaling.

Stress-induced apoptosis occurs when cells are exposed to genotoxic and/or cytotoxic drugs, γ-radiation, free radicals, metabolic toxins, ER stressors and toxins which disrupt cytoskeletal structures and cause detachment of the cells from the extracellular matrix. These stressors activate the intrinsic apoptotic pathway due to the perturbation of the mitochondrial membrane integrity. Mitochondria sequester a variety of pro-apoptotic proteins and their release requires disruption of mitochondrial membrane potential. The pro-apoptotic effectors sequestered in mitochondria include cytochrome C, Smac/DIABLO, HtrA2/0mi, the flavoprotein AIF and the endonuclease G. Once released from the mitochondrial compartment, cytochrome C interacts with the adaptor protein APAF-1 and induces conformational changes that allow the binding of dATP/ATP, thus forming the heptamer complex known as apoptosome. This complex in turn recruits and activates caspase 9 which in turn activates downstream effector caspases 3-6 and 7.

Blockade of cell death by NAC may point to the significance of oxidative stress in HEMA-mediated cell death and cytotoxicity. The major role of $O_2$ in normal metabolism is oxidative phosphorylation, an event that takes place in the mitochondria and is responsible for ATP generation. In this process oxygen receives four electrons to form $H_2O$. However, a single electron addition to $O_2$ can result in the formation of superoxide anions $O^{2-}$ while the gain of 2nd or 3rd electrons can lead to the formation of hydrogen peroxide ($H_2O_2$) or hydroxyl radical ($OH^-$), respectively. These reactive oxygen species are formed at very low levels under normal physiological conditions; however under conditions of oxidative stress significant levels of these reactive oxygen species (ROS) are formed which in turn react with proteins, lipids, and DNA leading to cellular damage. To maintain cellular redox equilibrium, ROS and oxygen radicals are neutralized by a variety of anti-oxidants. Under conditions of abundant ROS production, such as may occur during HEMA exposure, the antioxidant defenses may be overwhelmed leading to oxidative stress. Under this condition, a depletion of reduced glutathione (GSH) in exchange for a rise in oxidized glutathione (GSSG) is observed. Thus, a significant drop in the intracellular GSH/GSSG ratio may be observed.

NAC acts directly as a reducing agent and indirectly by stimulating the synthesis of other anti-oxidant enzymes such as glutathiones. At the intracellular level, NAC is a precursor of GSH synthesis since it can easily penetrate the cells where it will be deacetylated to form L-cysteine thus supporting the biosynthesis of GSH. Other examples of anti-oxidants which may have a role in protection against HEMA-induced oxidative stress are superoxide dismutase (SOD), catalase, gluthathione peroxide, gluthathione reductase, metallothionein (MT), heme oxygenase-1 and urate.

1. Decrease in mitochondrial membrane potential ($\Delta\psi m$) and induction of caspase 3 activation were blocked in the presence of NAC.

Similar to RAW 264.7 and THP-1 macrophage cells, (FIGS. 1 and 2) Jurkat T cells undergo apoptotic cell death when treated with varying concentrations of HEMA, and this cell death is significantly blocked in the presence of NAC. This effect was shown in a study in which Jurkat cells were cultured in a 5% $CO_2$ atmosphere in RMPI 1640 containing 10% FCS, 1% penicillin-streptomycin, 1% sodium pyruvate and 1% non-essential amino acids. Jurkat cells were then cultured in twelve-well plates and were treated with 0.082M-0.0082M HEMA and/or NAC (20 mM) simultaneously.

We investigated the effects of HEMA on the mitochondrial membrane potential. The membrane potential was assessed by staining with DiOC6 which is a positively charged dye. At low concentrations, it accumulates in mitochondria due to their large negative membrane potential. However when the membrane potential is disrupted there is less binding of this dye.

Figure 18:
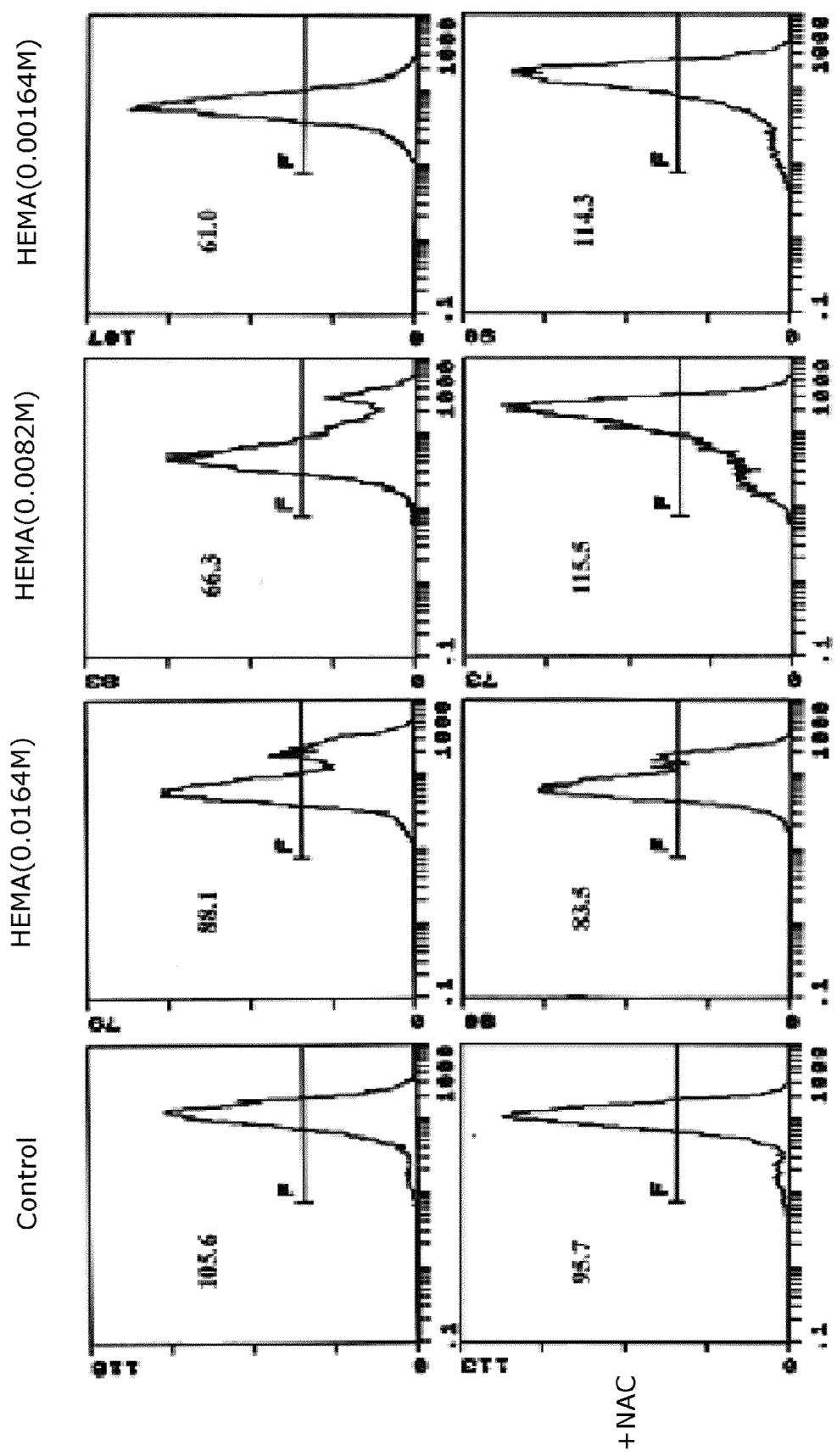
FIG. 18 shows that NAC restores mitochondrial membrane potential.
Figure 19A:
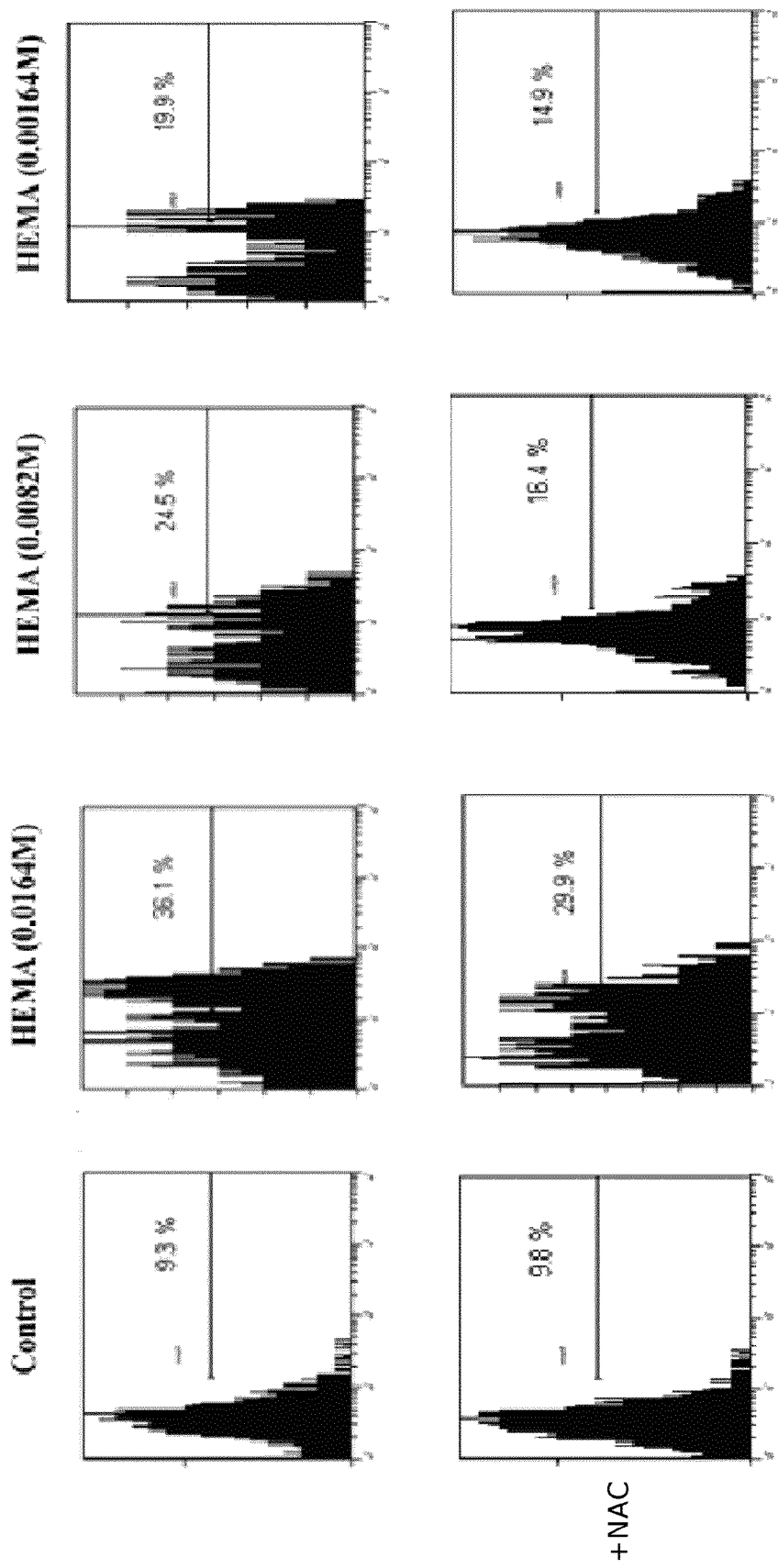
FIGS. 19A and 19B show that NAC decreases HEMA-induced caspase 3 induction (FIG. 19A) and prevents HEMA-induced cell death in Jurkat T cells (FIG. 19B)

Induction of cell death in Jurkat cells pararelled with a decrease in mitochondrial membrane potential ($\Delta\psi m$) (FIG. 18). The numbers in the figure demonstrate the relative intensities of the DiOC6 binding in each treated sample. There was also an increase in Caspase 3 induction in the cells treated with HEMA (FIG. 19A). NAC restored mitochondrial membrane potential and decreased the induction of caspase 3 expression induced by HEMA.

Figure 19B:
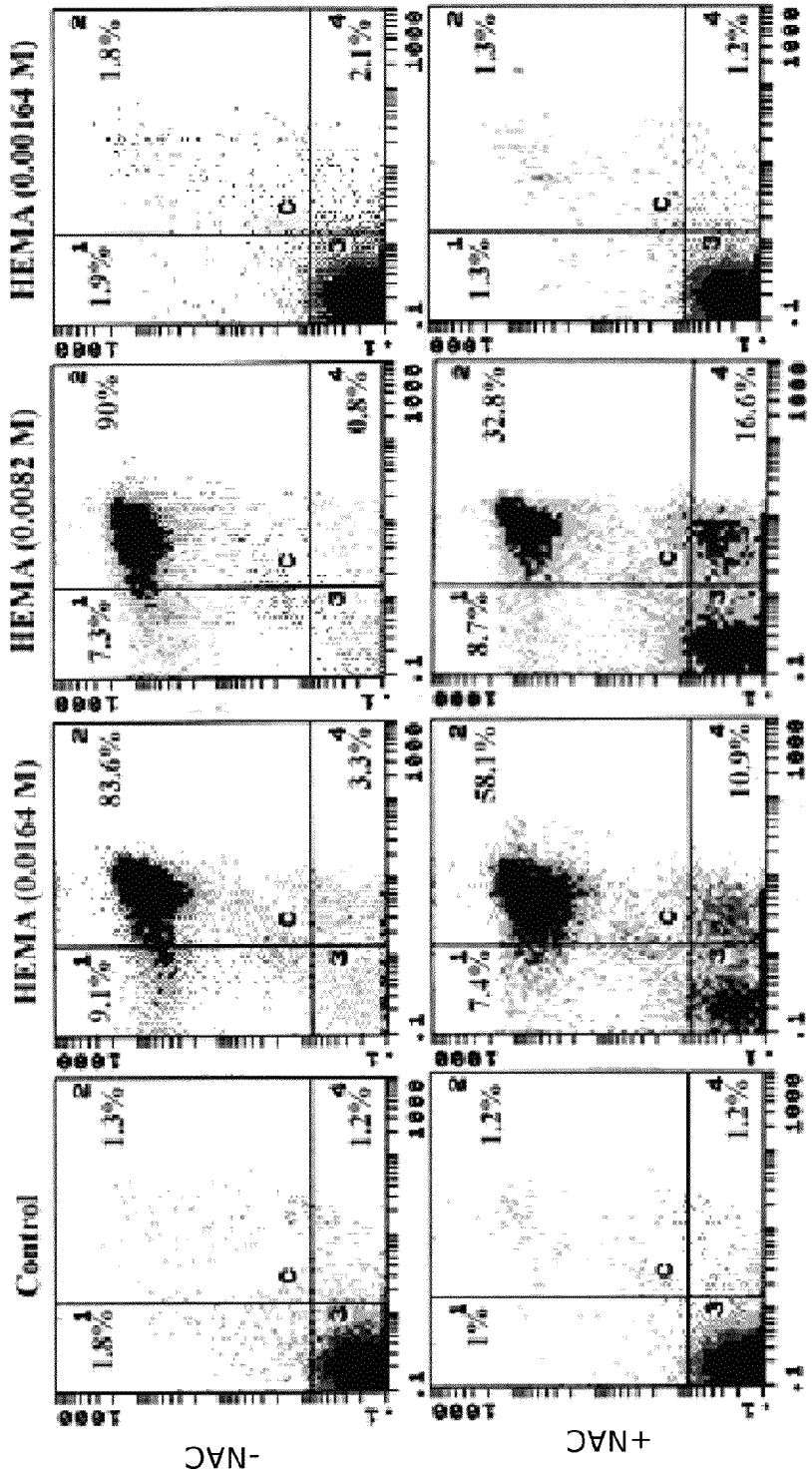

After an overnight incubation the levels of cell death in Jurkat T cells were determined using dual staining with PI/FITC-Annexin V as described previously (FIG. 19B). 10,000 events were analyzed for each sample. Similar results were obtained when apoptosis was assessed by PI staining of ethanol fixed Jurkat T cells.

Figure 20:
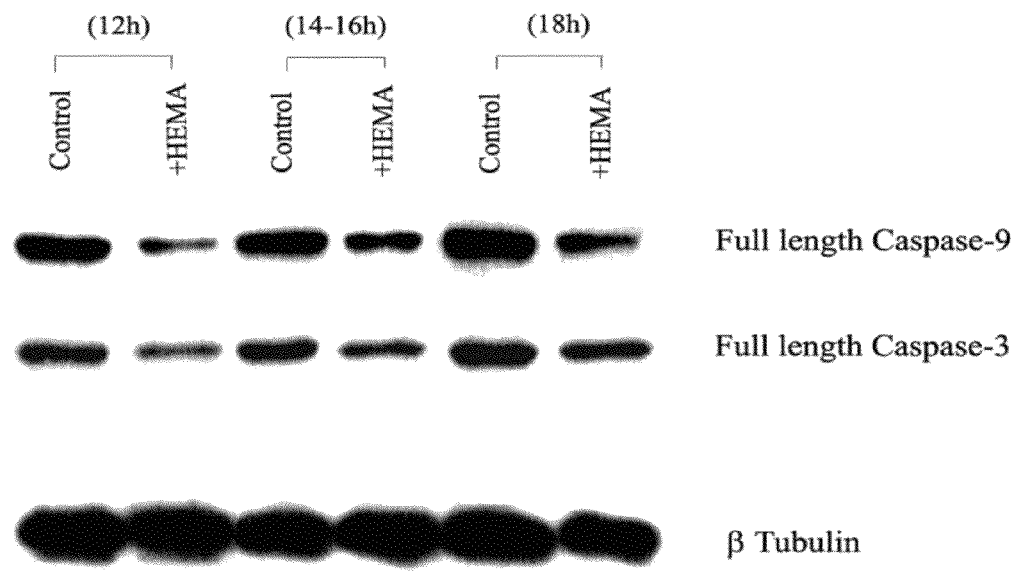
FIG. 20 shows that HEMA treatment decreases full length caspases 9 and 3 levels and that NAC inhibits HEMA-mediated decrease in caspases 9 and 3.

2. Decreased Levels of Full Length Caspase 9 and Caspase 3 in HEMA-Treated Keratinocytes A decrease in full length caspases 9 and 3 levels is a good indicator of increased apoptotic signaling during the intrinsic pathway of cell death. Therefore, HEp2 cells were treated with 0.0164M HEMA, and the levels of full length caspases 9 and 3 were determined. Specifically, HEp2 cells were treated with HEMA and incubated for about 18 hours. The cells were then lysed at 40° C. in RIPA buffer (50 mM Tris-HCl (pH 7.4), 1% Nonidet P-40, 0.25% sodium deoxycholate, 150 mM NaCl), and supplemented with one tablet of protease inhibitor cocktail, Complete Mini Roche (Indianapolis, Ind.). Protein concentrations were determined by a DC protein assay kit (Bio-Rad, Hercules, Calif.). An aliquot of total protein lysate was diluted in an equal volume of about 2% SDS sample buffer, about 6.2 mM Tris (pH about 6.8), about 2.3% SDS, about 5% mercaptoethanol, about 10% glycerol, and about 0.02% bromophenol blue and boiled for about 10 minutes. The cell lysates (40 μg) were then electrophoresed on 12% SDS-PAGE gels and were subjected to Western blot analysis. Levels of β-tubulin and actin were used to normalize the protein expression. Relative concentrations were assessed by densitometric analysis of digitized autographic images. The anti-actin and anti-β-tubulin monoclonal antibodies were purchased from Santa Cruz Biotechnology (Santa Cruz, Calif.) and from Calbiochem (San Francisco, Calif.) respectively. The polyclonal antibodies anti-caspase 3 and anti-caspase 9, were obtained from Cell Signaling (San Diego, Calif.). As shown in FIG. 20, HEMA treatment diminishes full length caspases 9 and 3 levels. These results indicate that both caspases 9 and 3 are important death effectors in HEMA-mediated apoptosis.

3. Decreased Processing and Cleavage of Caspase 3 in the Presence of NAC

Figure 21:
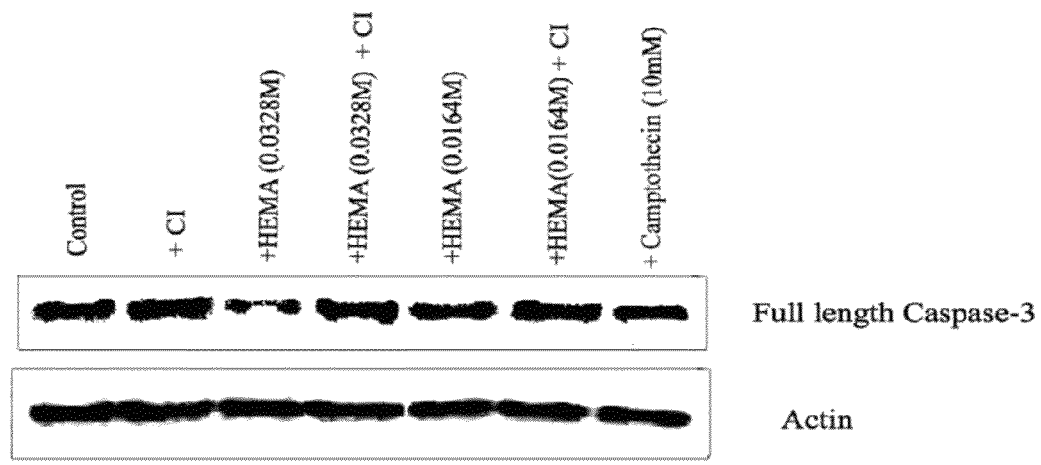
FIG. 21 shows that NAC inhibits HEMA-induced decreases in full length Caspase 3 in keratinocytes.

Treatment of keratinocytes in the presence of HEMA for about 8 hours results in a decrease in the levels of full length caspase 3. As shown in FIG. 21, this decrease is inhibited when keratinocytes are treated in the presence of NAC (20 mM). Further, addition of camptothecin, at a concentration which causes significant cell death in other tumor lines (10 mM), had a moderate effect in processing of caspase 3 in keratinocytes when compared to HEMA at the time period tested. At a shorter time period of treatment (about 8 hours) a higher concentration of HEMA was required to cause significant cleavage of caspase 3 in keratinocytes, whereas at about 12 to about 18 hours of treatment, a lower concentration of HEMA was capable of mediating a decrease in caspase 3 expression.

4. Roles of NFkB and GAPDH in HEMA-Mediated Cell Death

Nuclear factor kappa B (NFkB) is an important transcription factor that is necessary for cell survival. Cells treated with HEMA show a decrease in NFkβ levels when compared to untreated controls. Decreased levels of NFkB can activate an intrinsic pathway of cell death leading to apoptosis. Thus, a decrease in NFkB is one mechanism through which HEMA exposure may lead to cell death.

Cells exposed to HEMA also show a decrease in glyceraldehyde-3-phosphate dehydrogenase (GAPDH) levels when compared to untreated controls. GAPDH is a catalytic enzyme involved in glycolysis, a primary step in cellular metabolism. Thus, the decreased levels of GAPDH observed in HEMA exposed cells could cause damage to cells' mitochondria, in turn activating an intrinsic cell death pathway.

The following studies evaluate whether HEMA-mediated cell death may be caused at least in part by reductions in NFkB and/or GAPDH levels and whether NAC may prevent some of these changes.

a. NFKB Studies

Oral keratinocytes were treated with different concentrations of HEMA and/or tumor necrosis factor α (TNFα) as indicated in FIG. 22. After an overnight incubation, nuclear extracts of each sample were prepared, and equal amounts of protein were loaded in each lane. The levels of p65 subunit of NFkB in each lane was determined by the addition of monoclonal antibodies to the p65 subunit of NFkB. Actin was used as a loading control. Next, comparable treatments were carried out to determine whether the nuclear expression of NFkB is inhibited in dental pulp stromal cells after HEMA treatment.

As shown in FIGS. 22 and 23, HEMA is an important inhibitor of NFkB in oral keratinocytes and dental pulp stromal cells. Because NFkB induction is important for cell survival, HEMA's inhibitory effect on NFkB could be an important mechanism for the induction of death in oral keratinocytes and dental pulp stromal cells. To evaluate this possibility, the addition of HEMA to NFkB knock down cells results in significantly higher levels of cell death than in cells with intact levels of NFkB was examined.

One of the ways to check for the inhibition of NFkB in NFkB knock down cells is to measure the expression of ICAM-1 on the cell surface. This is because a decrease in NFkB results in a significant decrease in ICAM-1 expression. Thus, in the next described study, retrovirally-transduced human oral keratinocytes (HOK-16B) (containing a GFP marker) were left untreated or treated with interferon gamma (IFNγ) (200 μg/ml) overnight. The following day, levels of ICAM-1 expression were determined by staining with PE conjugated anti-ICAM-1 antibodies (Y axis).

Figure 24:
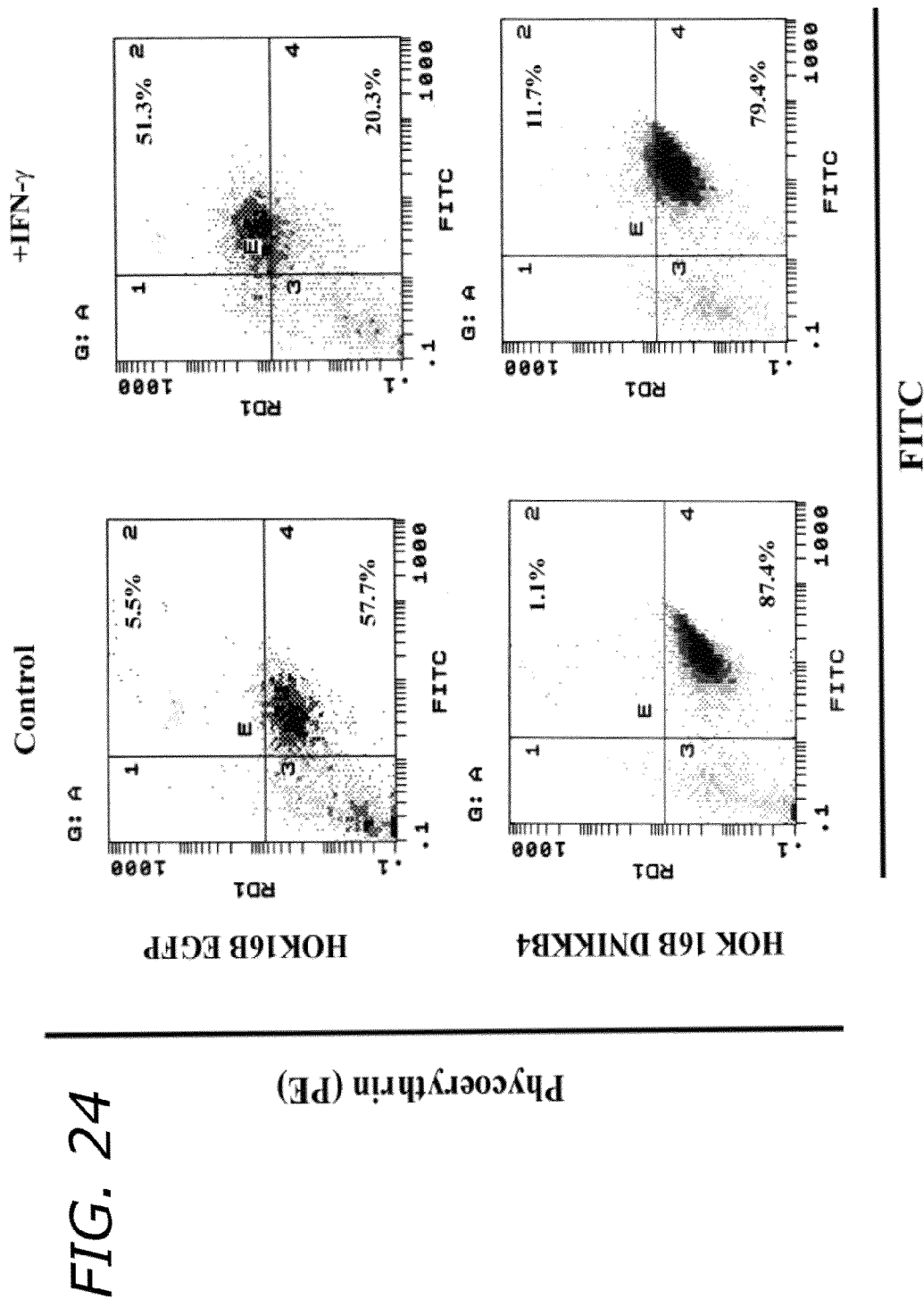
FIG. 24 shows a lack of induction of ICAM-1 expression in NFkβ knock down human oral keratinocytes (HOKs).

FIG. 24 shows the result of this study. The X axis shows GFP expression in control and DN-Ikkb-transduced HOKs. The Y axis represents staining with the antibody to ICAM-1. Numbers in each quadrant are the percentages of cells positive in that quadrant. Thus, FIG. 24 shows a decreased expression of ICAM-1 in NFkB knock down HOKs 11.7% vs. EGFP transduced 51.3%. Therefore, this study likely indicates the successful blocking of NFkB in oral keratinocytes because the increase in ICAM-1 expression by IFNγ was significantly blocked when NFkB was blocked in oral keratincytes. Thus, FIG. 24 shows a lack of induction of ICAM-1 expression in NFkB HOK-16B.

Figure 25:
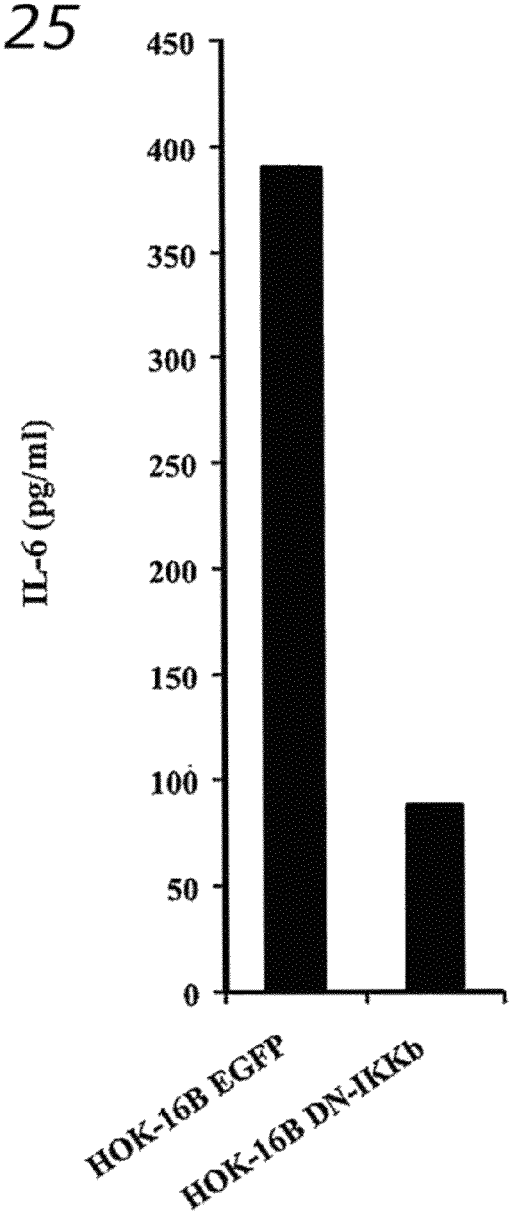
FIG. 25 shows a decreased induction of IL-6 release in NFkβ knock down HOKs.

Next, retrovirally-transduced HOKs were incubated overnight and supernatants were removed and assayed by ELISA for IL-6. As shown in FIG. 25, there was a decreased induction of IL-6 release in NFkB knock down HOKs. Indeed, inhibition of NFkB decreased IL-6 secretion by untreated HOKs significantly. Thus it appears that a constitutive increase in IL-6 secretion by HOKs could be dependent on the function of NFkB.

Figure 26:
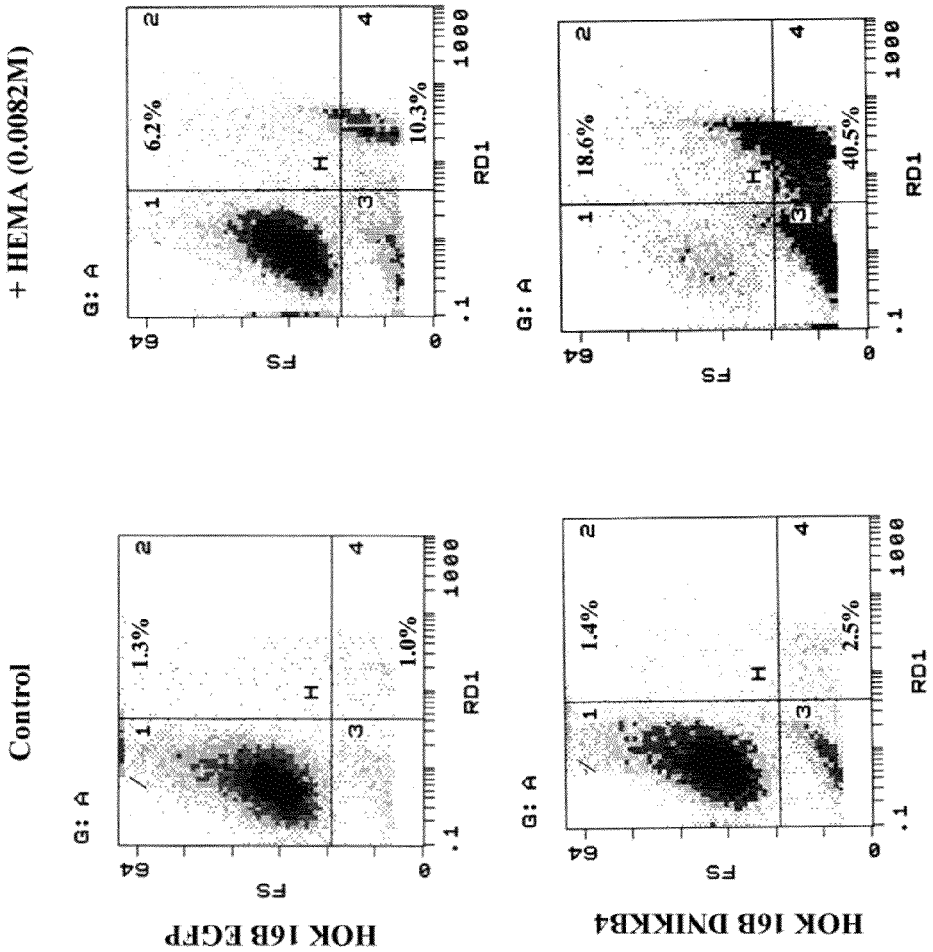

Next, retrovirally-transduced oral keratinocytes were left untreated or treated with HEMA. After an overnight incubation the levels of cell death were determined using FS (Y axis) and PI (X axis). Numbers in each quadrant represent the percentages of cells in that quadrant. FIG. 26 shows a decreased FS and increased PI staining induced by HEMA in NFkB knock down oral keratinocytes. Thus HEMA induces significant cell death in NFkB knock down oral keratinocytes and it is likely that the status of nuclear NFkB is important for the death inducing function of HEMA.

Similar treatments were next performed as described above except that the morphological assessment of oral keratinocytes before and after HEMA treatment was examined. As shown in FIG. 27, cells were dead when NFkB knock down HOKs were exposed to HEMA as compared to cells with intact NFkB function. Also note that NFkB knock down HOKs in the absence of HEMA did not show significant death. This suggests that HEMA-mediated inhibition of NFkB may not be the sole factor responsible for the induction of cell death.

The effects of HEMA and/or NAC on TNFα and IFNγ release from peripheral blood mononuclear cells were also examined. EGFP- and DN-Ikkb transfected HOKs were treated with HEMA (0.082M) and/or NAC (20 mM) or LPS (10 ng/ml) for 1 hour after which the cells were washed and co-cultured with peripheral blood mononuclear cells at a peripheral blood mononuclear cell to HOK ratio of 10:1. After an overnight incubation the supernatants were removed and the release of TNFα or IFNγ was determined using an ELISA.

Figure 28:
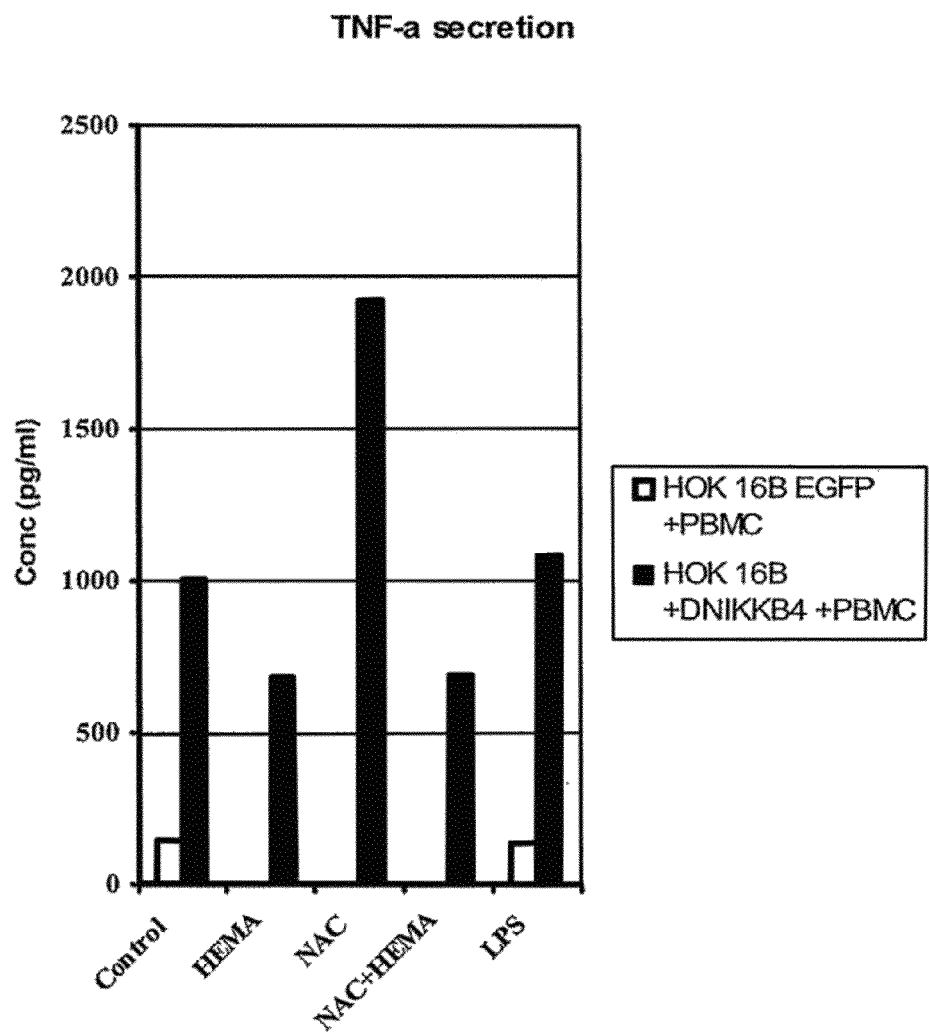
FIG. 28 shows that blocking NFkβ in human oral keratinocytes increases TNFα secretion from peripheral blood mononuclear cells.
Figure 29:
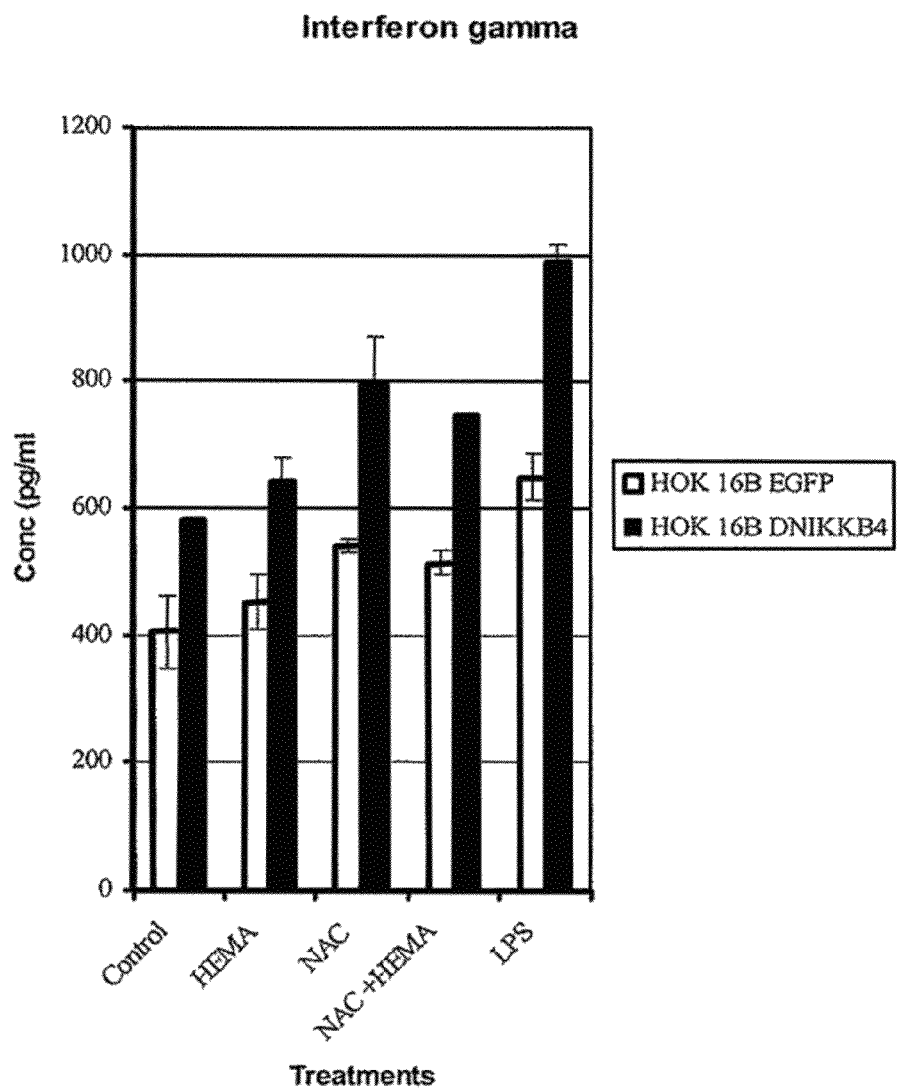
FIG. 29 shows that blocking NFkβ in human oral keratinocytes increases IFNγ secretion from peripheral blood mononuclear cells.

As shown in FIGS. 28 and 29, blocking NFkB in human oral keratinocytes increases both TNFα and IFNγ secretion from PBMCs. Because HEMA blocks NFkB, and blocking NFkB increases immune activation this could be a mechanism for the increased hypersensitivity observed in patients with dental resin allergies. It also indicates that the death inducing effect of dental resins can be exacerbated by recruiting immune inflammatory cells to the site and increased function of immune cells resulting in further damage of the affected tissue (i.e. dental pulp or skin exposure).

b. GAPDH Studies

Figure 30:
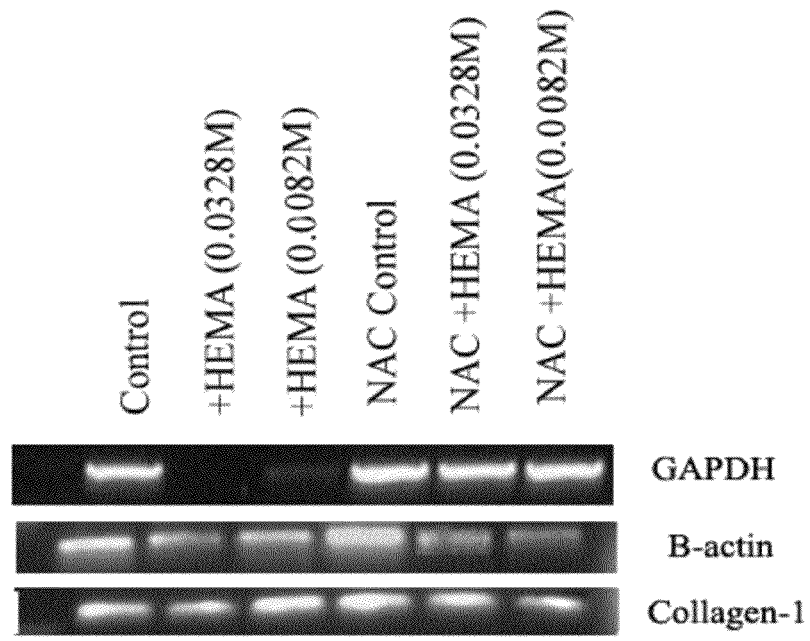
FIGS. 30 and 31 show that NAC blocks HEMA-mediated inhibition of GAPDH mRNA in dental pulp stromal cells (FIG. 30) and HEMA-mediated inhibition of GAPDH protein expression in dental pulp stromal cells (FIG. 31).

The role of GAPDH in HEMA-mediated cytotoxicity was also evaluated. Dental pulp stromal cells were treated with different concentrations of HEMA (concentrations indicated in FIG. 30) and NAC (20 mM) for 4 hours, after which RNAs from each sample were extracted and RT-PCR was performed using specific primer sets for GAPDH, β-actin and collagen-1. As seen in FIG. 30, significant inhibition of GAPDH mRNA was seen in dental pulp stromal cells after treatment with HEMA. NAC prevented this inhibition. In comparison no significant decrease in β-actin and collagen-1 under the same experimental conditions could be seen. Thus, NAC can block HEMA mediated inhibition of GAPDH mRNA in dental pulp stromal cells.

Figure 31:
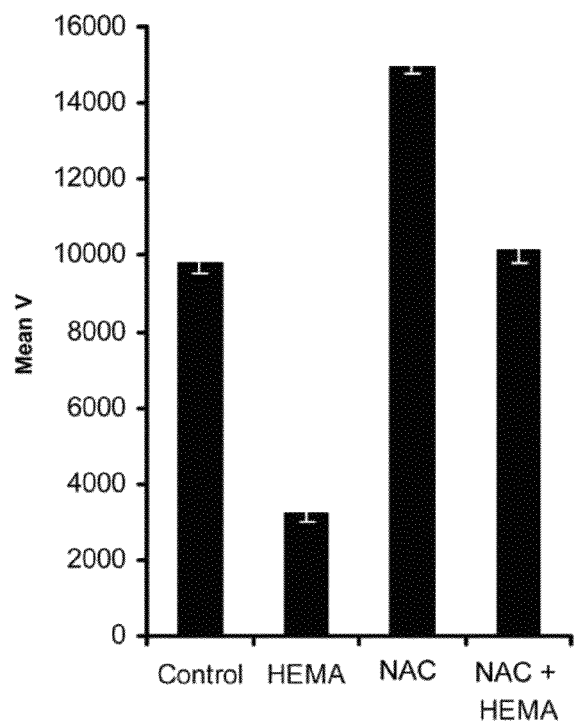

Dental pulp stromal cells were also treated with HEMA (0.082M) and NAC (20 mM). After 4 hours of incubation the protein levels of GAPDH were determined using a KDalert GAPDH assay kit (Ambion). This assay is a fluorescent based assay which measures the conversion of NAD+ to NADH catalyzed by GAPDH. As shown in FIG. 31, HEMA induced a significant decrease in GAPDH protein expression in dental pulp stromal cells with the addition of NAC preventing the decrease in GAPDH protein expression.

Figure 32A:
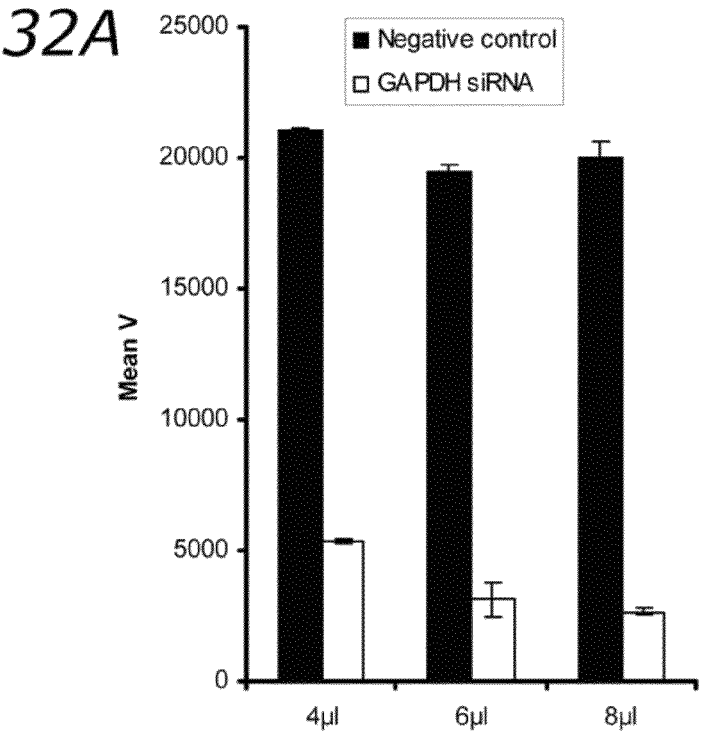
FIGS. 32A (HOK) and 32B (dental pulp stromal cells) show successful blockage of GAPDH by GAPDH specific siRNA.
Figure 32B:
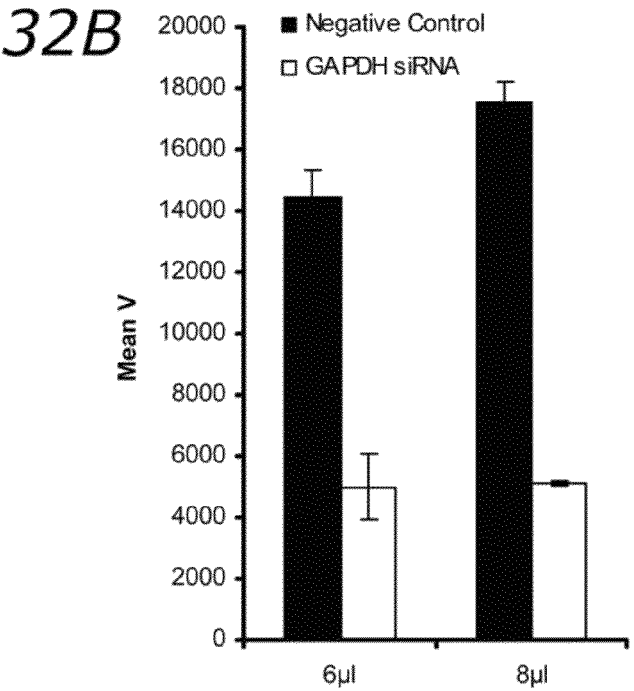

In order to examine whether the sole inhibition of GAPDH is sufficient for the induction of cell death, GAPDH was blocked with specific siRNA in HOK-16B (FIG. 32A) and dental pulp stromal cells (FIG. 32B). $1 \times 10^5$ HOK-16B and dental pulp stromal cells ($\beta$-glycerophosphate+ascorbic acid) were transfected with different concentrations of control siRNA (non specific) and GAPDH siRNA (4 µl=20 nM to 8 µl=40 nM) using lipofectamin 2000. After 2 days of incubation cells were trypsinized, washed and lyzed in lysis buffer provided in the kit. Levels of cell death after 2 days of incubation were then evaluated. GAPDH protein levels were determined using the KDalert GAPDH assay kit. As seen in FIGS. 32A and 32B, significant decreases in GAPDH protein were obtained and no significant induction of cell death could be seen after inhibition of GAPDH in HOK-16B or dental pulp stromal cells (data not shown). Therefore, sole inhibition of GAPDH alone or NFkB alone may not be sufficient to induce cell death and it is possible that blocking both GAPDH and NFkB by HEMA is important for the synergistic induction of cell death.

5. Comparison of NAC to Antioxidants

Figure 33:
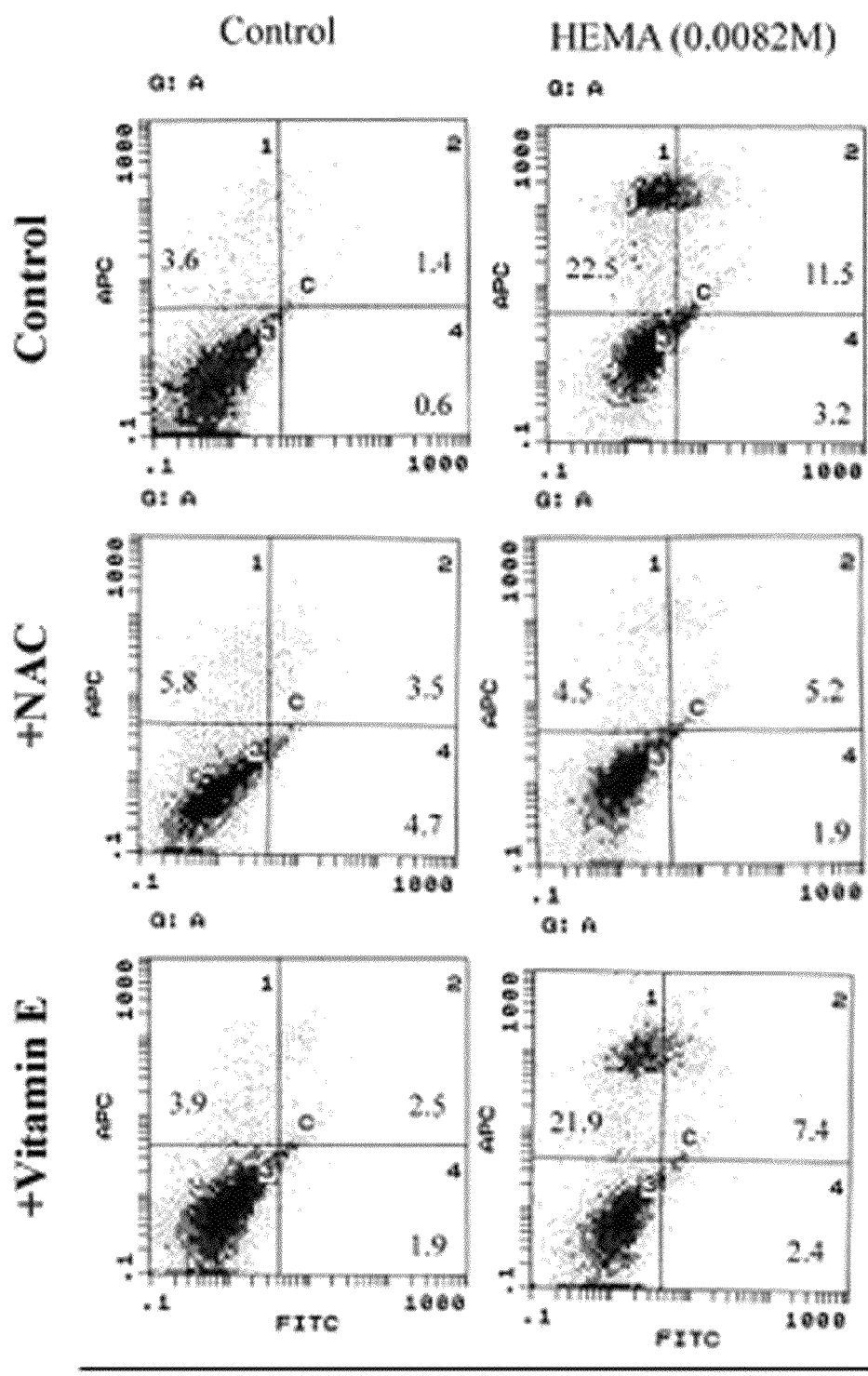
FIG. 33 shows that Vitamin E fails to inhibit HEMA-mediated cell death in human dental pulp stromal cells.
Figure 35:
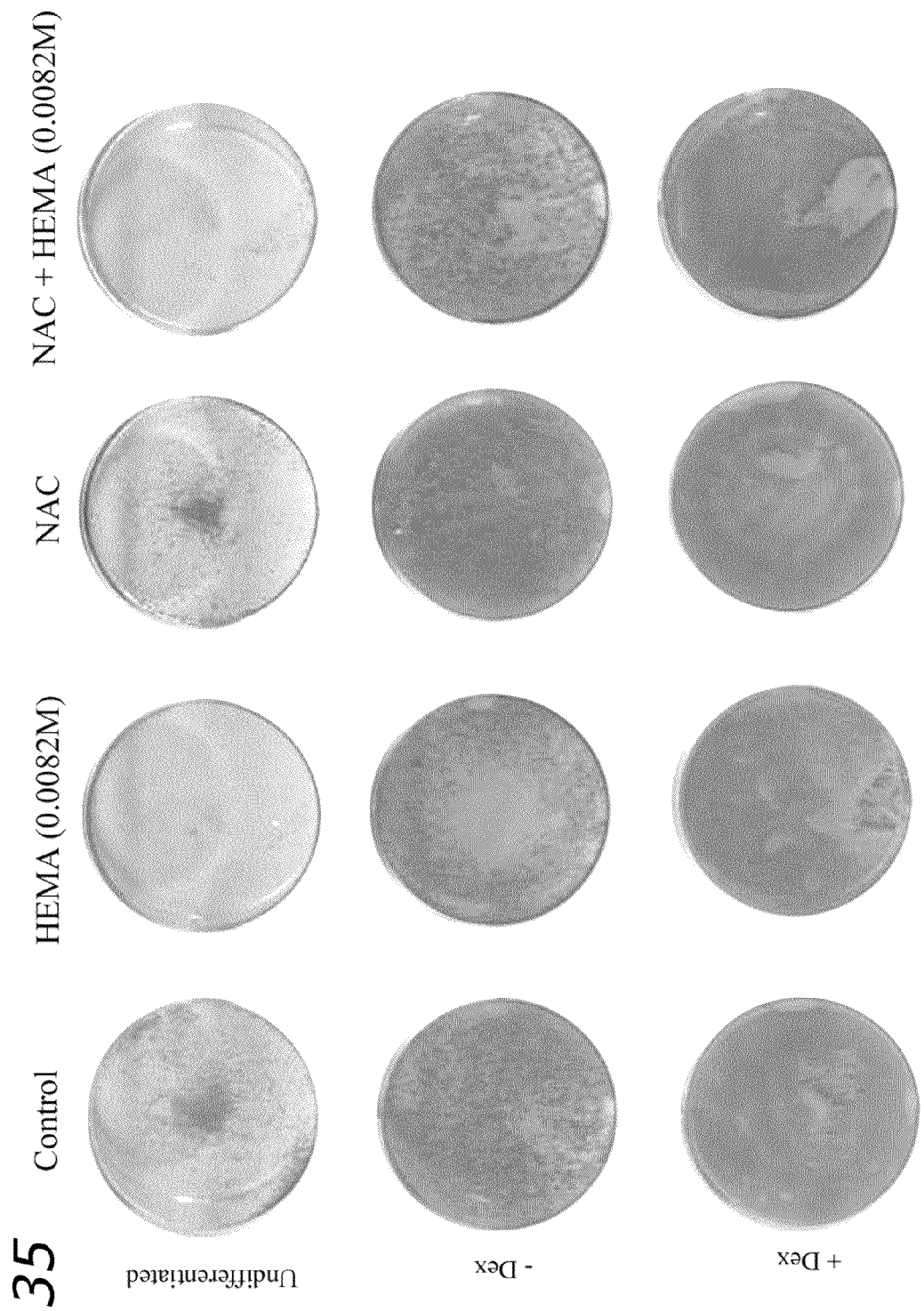
FIG. 35 shows that differentiated cells can be resistant to HEMA-mediated cell death.

Dental pulp stromal cells were grown in media containing $\beta$-glycerophosphate and ascorbic acid until they reached confluency, after which the cells were detached and treated with HEMA (0.0082M) and/or NAC (20 mM) and/or vitamin E (5 mM) for a period of 4 hours. Following the 4 hour incubation, cells were analyzed for apoptosis using FTIC-Annexin V and PI. As shown in FIG. 33, unlike NAC, Vitamin E failed to inhibit HEMA mediated cell death of human dental pulp stromal cells. This result indicates that the effect of the antioxidant Vitamin E on HEMA mediated cell death is distinct from that mediated by NAC.

Dental pulp stromal cells were then treated as described in the preceding paragraph with supernatants removed and assayed for VEGF levels by ELISA following the 4 hour incubation. Unlike NAC, Vitamin E failed to prevent the HEMA mediated decrease in VEGF secretion from human dental pulp stromal cells (Table 5)

TABLE 5

| Group | Human dental pulp stromal cells |
| --- | --- |
| Control | 2263.9 |
| HEMA (0.0164M) | 73.79 |
| HEMA (0.0082M) | 72.6 |
| HEMA (0.00164M) | 57.26 |
| NAC | 1532.4 |
| NAC + HEMA (0.0164M) | 1648.1 |
| NAC + HEMA (0.0082M) | 1477.5 |
| NAC + HEMA (0.00164M) | 2123.9 |
| Vit E | 1966.2 |
| Vit E + HEMA (0.0164M) | 63.16 |
| Vit E + HEMA (0.0082M) | 83.18 |
| Vit E + HEMA (0.00164M) | 80.28 |
| NAC + Vit E | 1472.6 |
| NAC + Vit E + HEMA (0.0164M) | 964.2 |
| NAC + Vit E + HEMA (0.0082M) | 1081.4 |
| NAC + Vit E + HEMA (0.00164M) | 871.5 |

Rat dental pulp stromal cells were next treated with HEMA in the presence and absence of another antioxidant, ascorbic acid. After an overnight incubation following procedures similar to those described above, levels of cell death were determined using FITC Annexin V and PI. As shown in FIG. 34, unlike NAC, ascorbic acid did not reverse apoptosis induced by HEMA (left lower panel ascorbic acid alone treatment, right lower panel, is ascorbic acid+HEMA). These studies suggest that it is likely that the mechanism of NAC function is quite distinct from that exerted by antioxidants 6. Role of Cell Differentiation Studies These next described experiments were performed to evaluate the resistance of differentiated cells to HEMA-mediated cell death. Rat dental pulp stromal cells were cultured under 3 different conditions: (1) DMEM alone (undifferentiated); (2) DMEM+$\beta$-glycerophosphate+ascorbic acid (differentiated–Dex); and (3) DMEM+$\beta$-glycerophosphate+ascorbic acid+dexamethasone (differentiated+Dex). Cells were plated and treated with HEMA (0.0082M) and NAC (20 mM) and were then analyzed for ALP staining after 18 hours.

Figure 36:
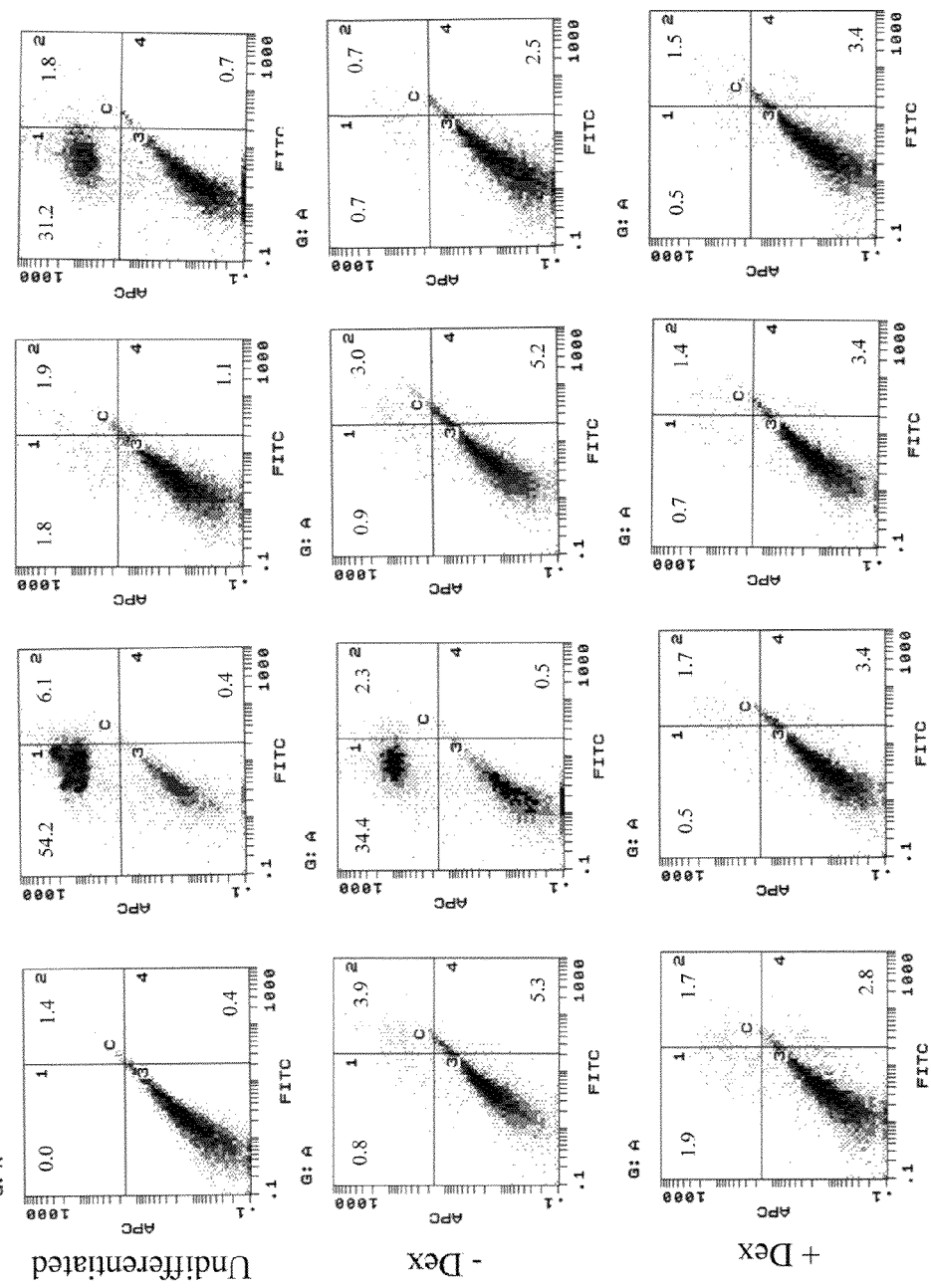
FIGS. 36 and 37 shows that the protective effect of NAC against HEMA-mediated cell death is similar to agents that induce cell differentiation.

Next, rat dental pulp stromal cells were cultured under the same 3 different conditions: (1) DMEM alone (undifferentiated); (2) DMEM+$\beta$-glycerophosphate+ascorbic acid (differentiated–Dex); and (3) DMEM+$\beta$-glycerophosphate+ascorbic acid+dexamethasone (differentiated+Dex). Cells were plated and treated with HEMA (0.0082M) and NAC (20 mM) for 18 hours and then stained with FITC-Annexin V and analyzed by flow cytometry for apoptosis. As shown in FIG. 36, cells cultured in media with dexamethasone were more resistant to HEMA mediated cell death. These studies suggest that the effect of NAC is similar to other agents that induce differentiation in cells.

Figure 37:
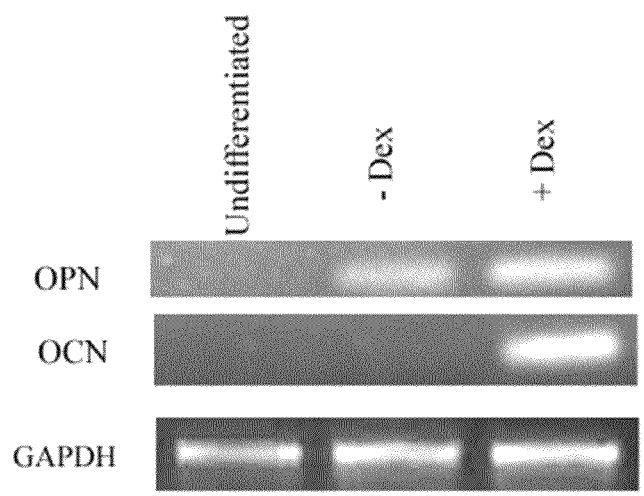

Rat dental pulp stromal cells were again cultured under 3 different conditions: (1) DMEM alone (undifferentiated); (2) DMEM+$\beta$-glycerophosphate+ascorbic acid (differentiated–Dex); and (3) DMEM+$\beta$-glycerophosphate+ascorbic acid+dexamethasone (differentiated+Dex). The differentiation of the cells under these different culture conditions was then confirmed by an RT-PCR to assay for genes which are induced during differentiation (osteopontin and osteocalcin). Osteopontin (OPN), is an early osteoblastic marker and osteocalcin (OCN) a late stage marker. As can be seen in FIG. 37, dexamethasone (Dex) differentiated the dental pulp stromal cells towards osteoblasts whereas cells in differentiated media without Dex showed only early osteoblastic/odontoblastic markers.

Figure 38:
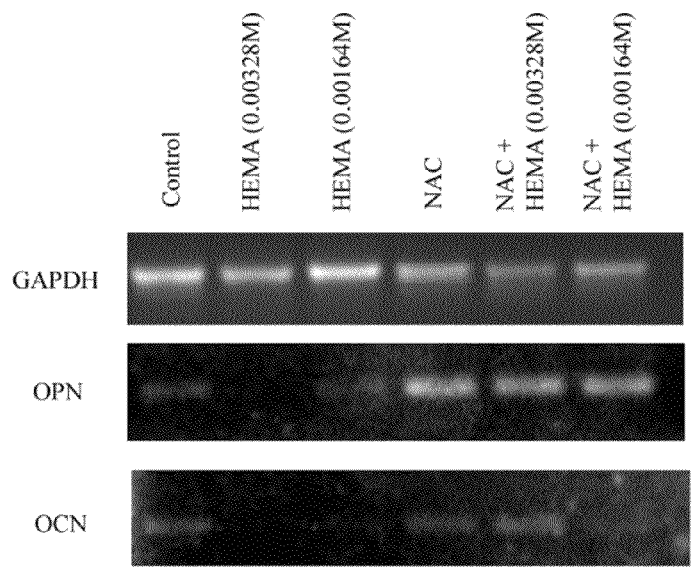
FIG. 38 shows that NAC may produce its protective effect against HEMA-mediated cell death by promoting cell differentiation.

Rat dental pulp stromal cells were also treated as shown in FIG. 38, cultured in media containing ascorbic acid and $\beta$-glycerophosphate. RNA was extracted from the cells and PCR was again performed for OPN and OCN. As can be seen in FIG. 38, in the presence of NAC, dental pulp stromal cells express higher levels of OPN and OCN when compared to controls. These studies suggest that it may be likely that NAC exerts its effect by differentiating pulpal cells. The levels of GAPDH remained high in all treated samples.

7. Comparison between Cytotoxicity Induced by HEMA and that of Cisplatin

After the initial observations that HEMA in varying concentrations is toxic to a variety of cells, the relative toxicity of HEMA as compared to that mediated by cisplatin was examined. Cis-diaminedichloroplatinum (II) (CDDP, cisplatin) is a widely used anticancer drug for the treatment of, without limitation, head & neck, testicular, ovarian, bladder, and small cell lung carcinoma. The anticancer activity of CDDP is attributed to its ability to form DNA-platinum adducts, which leads to the disruption of DNA synthesis. Generation of reactive oxygen species (ROS) by CDDP is also involved in its cytotoxic actions. Cisplatin-DNA adducts can inhibit fundamental cellular processes, including replication, transcription, translation and DNA repair.

CDDP concentrations of 1-15 mg/ml were used routinely used to induce significant cell death in different cell lines including those of A2780, AD10, and C30 cell lines. PBMCs isolated from a healthy control were treated with different concentrations of HEMA (0.0164M-0.00164M) as well as CDDP (5, 10, 20 mg/ml) for about 18 hours. The cells were then stained with FITC-Annexin V and PI according to the manufacturer's protocol. Flow cytometric analyses indicated that at the highest concentration of CDDP 80% of the cells remained both PI and Annexin V negative whereas less than 50% of the cells treated with HEMA were unstained in the presence of PI and Annexin V (FIG. 39A). A dose dependent decrease in the levels of Annexin V and PI staining could be observed when lower concentrations of HEMA were added to the cells.

In order to assess the levels of active caspase 3 induction, PBMCs were treated with HEMA and CDDP (concentrations were similar to those stated previously). The samples were then stained with FITC conjugated with monoclonal antibodies recognizing active caspase 3.

Figure 39B:
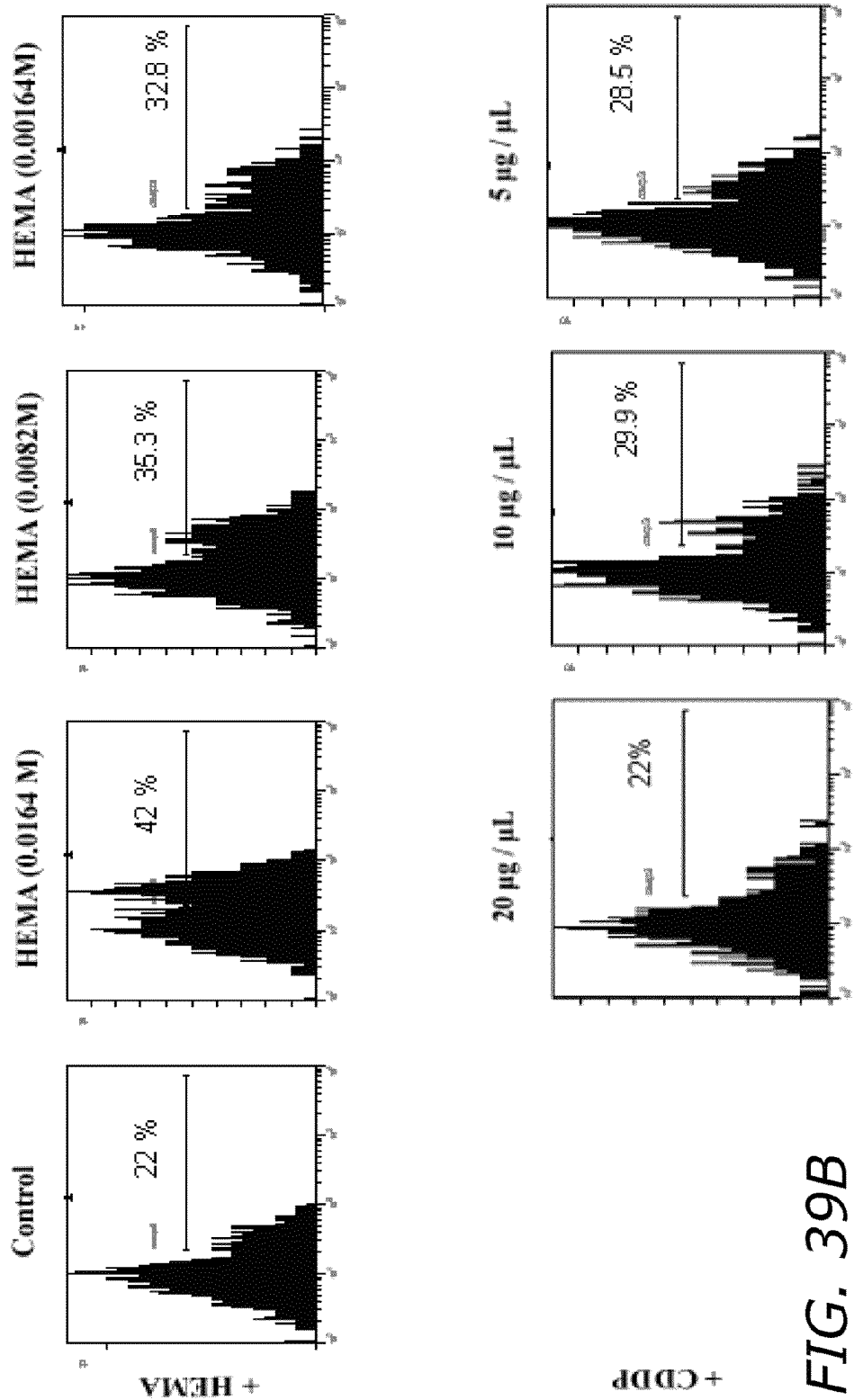

The results clearly correlated with those obtained by Annexin V/PI staining. Increased levels of active caspase-3 staining were observed in HEMA treated cells (0.0164M) as compared to CDDP treated cells. HEMA treated cells demonstrated an about 2-fold increase (42%) in active caspase 3 staining when compared to the CDDP treated cells (22%). (FIG. 39B)

Collectively, these results indicated that the cell death-inducing effect of HEMA is not limited to certain cells and that HEMA-mediated cell death could be through the intrinsic pathway of cell death.

In vivo studies were performed after tooth restorations to assess the protective effect of NAC on both the viability and function of rat pulp tissue. Eight week old male rats were used for restorations of the incisors. In this study the number of functional cells in cells extracted from the lining of the rat teeth where (A) no restorative materials were administered; (B) restorative materials only were applied; and (C) restorative material in conjunction with NAC were compared. Specifically, nine rats were used and were divided into 3 groups (A, B or C) of 3 rats each. Preparations were made in both maxillary and mandibular anterior incisors (2 maxillary, 2 mandibular).

In group A, no preparations were made, and the pulp was extracted after 5 hours for evaluation. In Group B, the incisors were prepared with class V preparations. Near the level of the gingival, both the maxillary and mandibular teeth were utilized. The teeth were prepared with a #1 round bur which measures 1 mm in diameter in a high speed dental handpiece. The preparation was about ½ mm deep (half the depth of the bur) not violating the pulp space. The cavity for Group B was then restored in the following manner: (1) the cavity preparation was etched with 37% phosphoric acid for about 10 seconds; (2) irrigated with tap water for 5 seconds; (3) excess fluids removed with air syringe; (4) dental bonding agent applied per manufacturer's directions. Specifically, ProBOND was used. The directions were to: (i) apply primer, scrubbing for 30 seconds; (ii) gently dry with mild air flow; (iii) apply Bond; (iv) gently dry with mild air flow; (v) light-cure for 10 seconds with LED curing unit, Flash lite 1001. Following these steps, composite restoration (Herculite XR) was applied to the normal contour of the dentition; and the composite restoration was cured with LED light curing unit for about 40 seconds. Upon completion, the restoration was left as is for about 5 hours and thereafter the pulp was extracted for evaluation.

In Group C, the incisors were prepared with class V preparations near the level of the gingiva, and both the maxillary and mandibular teeth were utilized. The teeth were prepared with a #1 round bur which measures 1 mm in diameter in a high speed dental handpiece. The preparation was about ½ mm deep (half the depth of the bur) not violating the pulp space. The cavity was then restored in the following manner: (1) the cavity preparation etched with 37% phosphoric acid for about 10 seconds; (2) irrigated with tap water for about 5 seconds; (3) pulp NAC solution applied; (4) excess fluids removed with air syringe; (5) dental bonding agent applied per manufacturer's directions. Specifically, ProBOND was used. The directions were to: (i) apply primer, scrubbing for 30 seconds; (ii) gently dry with mild air flow; (iii) apply Bond; (iv) gently dry with mild air flow; (v) light-cure for 10 seconds with LED curing unit, Flash lite 1001. Following these steps, composite restoration (Herculite XR) was applied to the normal contour of the dentition; and the composite restoration was cured with LED light curing unit for about 40 seconds. Upon completion, the restoration was left as is for about 5 hours and thereafter the pulp was extracted for evaluation.

The cells were treated as described in section A-2 relating to peripheral blood mononuclear cells and plated in 6 well plates in media containing 50 µg of ascorbic acid and about 10 mM of β-glycerophosphate to differentiate them into odontoblasts (as previously described). The media was changed every 3 days and 2 weeks later, ALP staining was performed as previously described.

FIG. 9 demonstrates an ALP staining showing NAC's ability to preserve cell function in the presence of HEMA. FIG. 7 shows photographs that were taken with an inverted microscope (20× magnification) to show the differences in cell proliferation between the 3 groups of the in vivo study.

Figure 40:
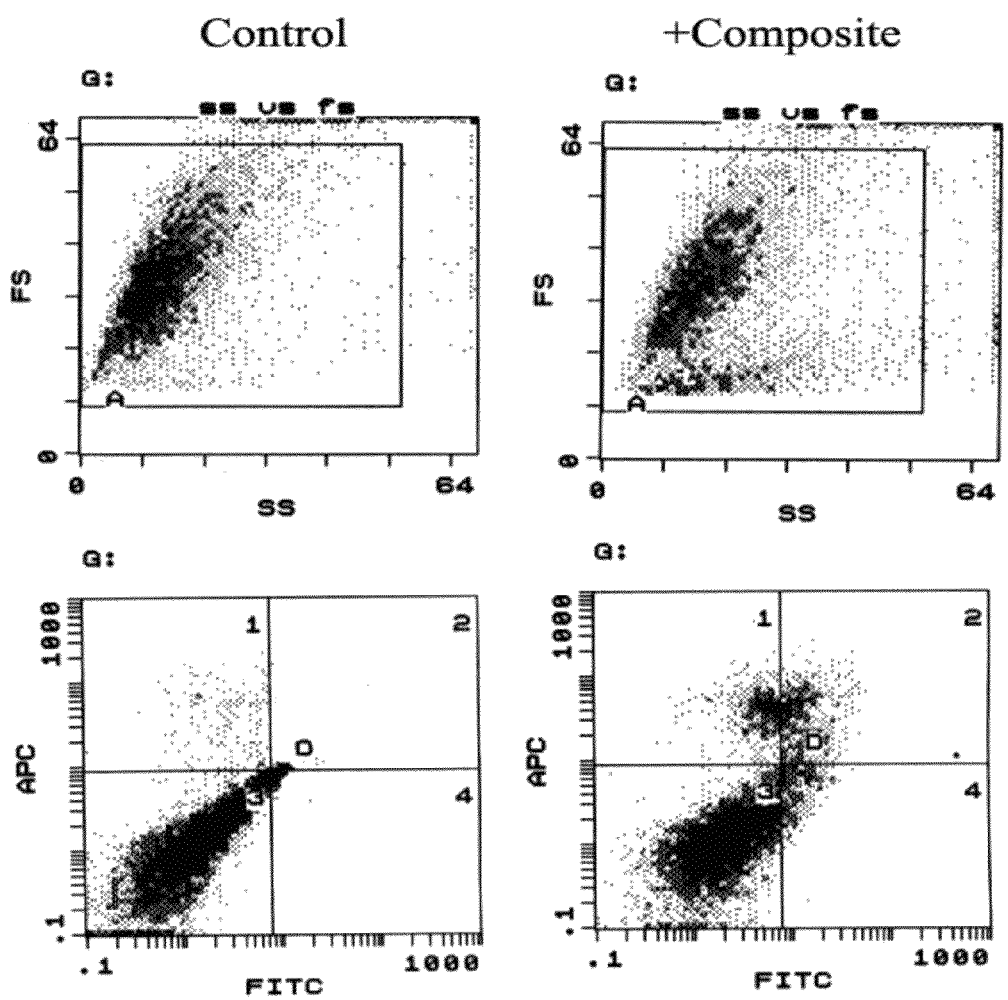
FIG. 40 shows that NAC inhibits cell death induced by light cured composite disks.

Next, the effects of routinely used composites on the odontoblasts were tested. The composite discs were made according to ADA specifications. These discs were completely cured for a total time of about 90 seconds. The discs were then placed into culture dish inserts (Millipore, Calif.). The inserts had a pore size of 0.4 µm which is about the diameter of the dentinal tubules. The insert along with the composite disc were placed into the well containing the differentiated pulp cells. After one week of incubation at about 37° C. the cells were removed and the numbers of apoptotic cells were analyzed using FITC-Annexin V/PI as described previously. As is seen in FIG. 40 the number of apoptotic cells were higher in wells containing the composite discs.

Figure 41:
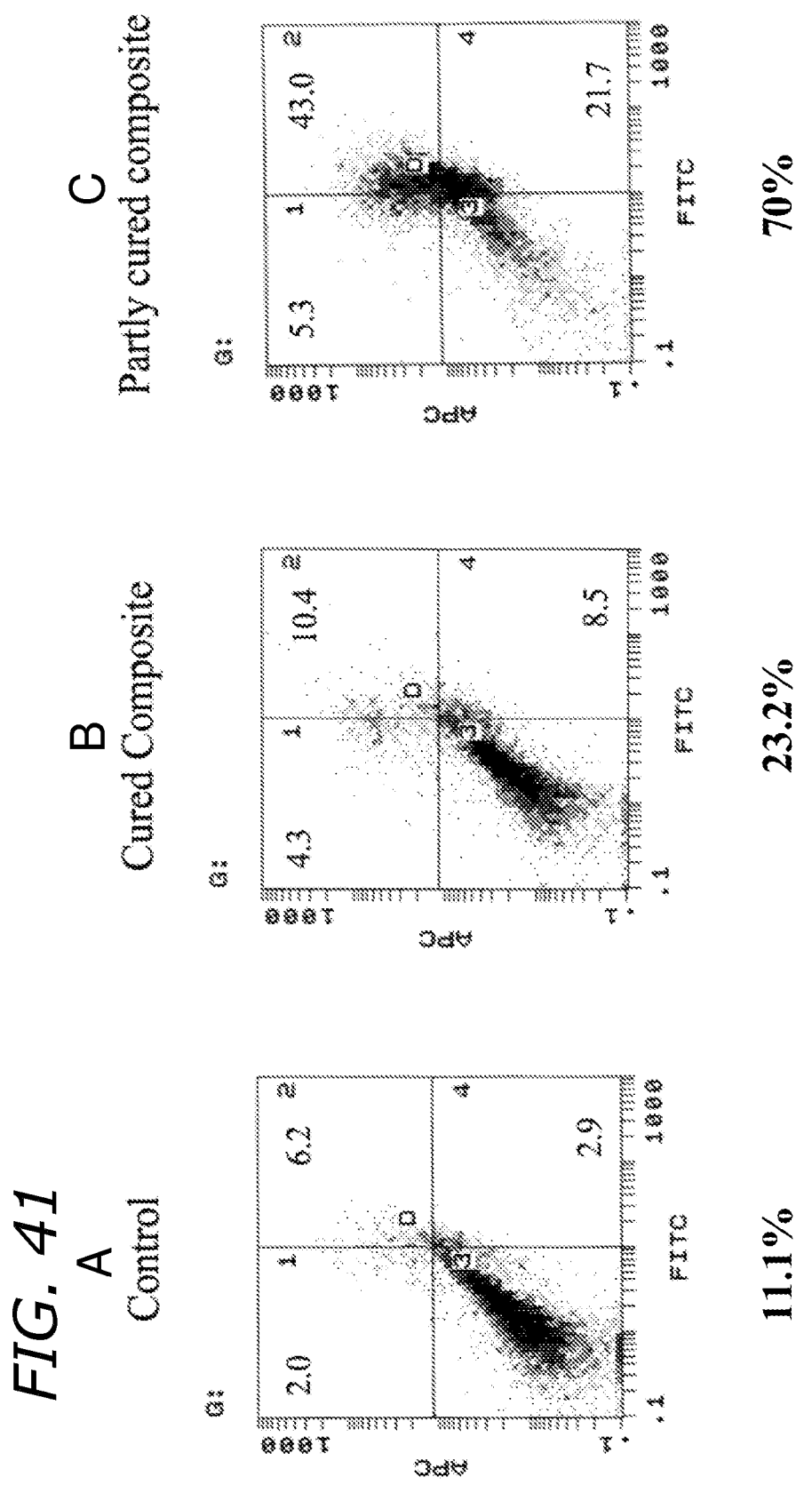
FIGS. 41A-C show the effect of NAC in cured (FIG. 41B) and partially cured (FIG. 41C) composite disks.

The effect of completely cured versus partially cured composite resins was also examined. Completely and partially cured composite discs were left in media for 3 days after which they were trypsinized and analyzed with FITC-Annexin V and PI. FIG. 41A-C shows these results.

C. Additional NAC Applications
1. Bleaching Agents

Rats were divided into the following groups: A: control, unbleached; B: bleached with no NAC; and C: Bleached with NAC. The bleaching agent used in the following studies was Oral B Rembrandt whitening system (containing 33% hydrogen peroxide and carbamide) often used in dental offices (chair side). NAC was initially painted on teeth at a 20 mM concentration for 5 minutes. Next a bleaching agent was applied for 5 hours, after which the teeth were extracted, and pulp was obtained from each group and treated with trypsin/EDTA (0.25%) and collagenase (0.02%). This resulted in a single cell suspension which was washed and resuspended in DMEM containing β-glycerophosphate (10 mM) and ascorbic acid (50 µg/ml), and allowed to grow to confluency. FIG.

Figure 42:
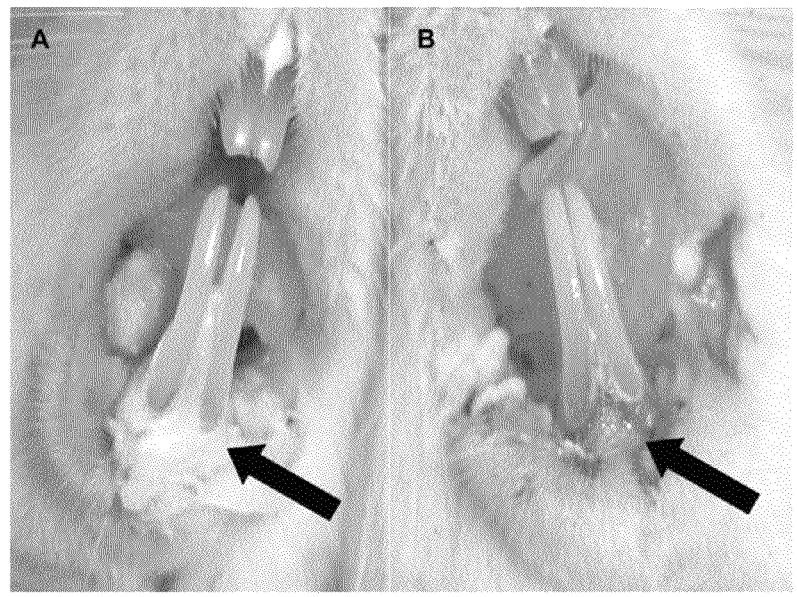
FIGS. 42A and 42B show that NAC can reduce the occurrence of tissue death following tooth bleaching.
Figure 43:
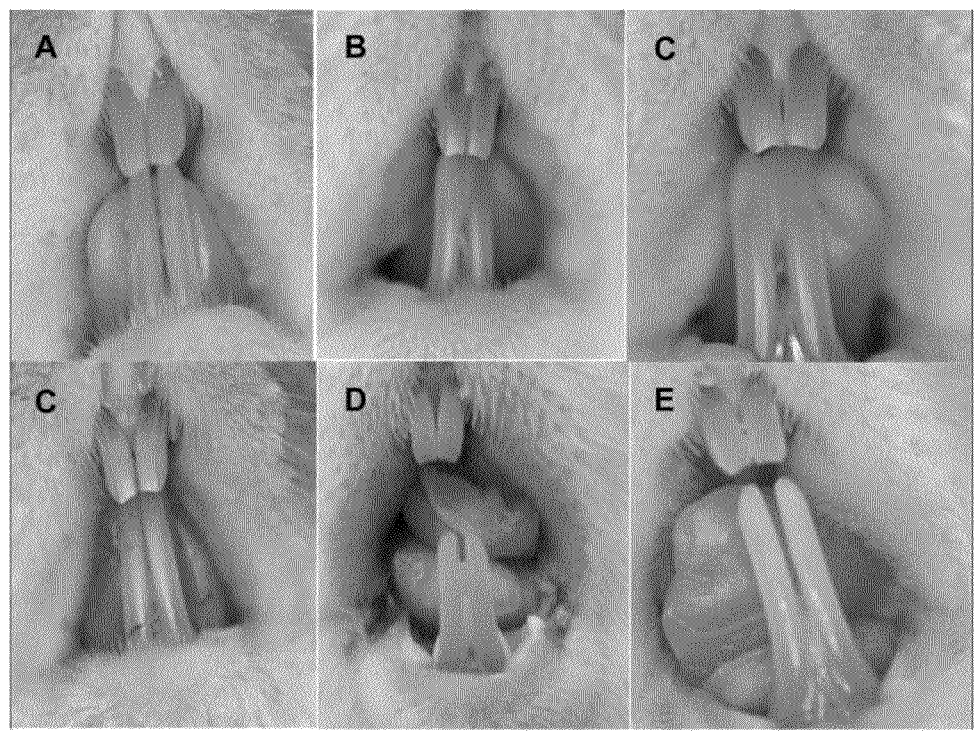
FIGS. 43A-43F show the effects of NAC on the efficacy or potency of tooth bleaching systems.

43 shows photographs of the teeth taken before bleaching (A,B,C) and after bleaching (D,E,F). Note the white patches on E representing dead tissues. Also note that bleaching in the presence of NAC (F) was as effective as bleaching without the NAC (E). Therefore, NAC does not decrease the efficacy or potency of the bleaching system. FIG. 42 also shows photographs taken after the bleaching (without NAC, left panel FIG. 42A) and (with NAC, FIG. 42B). Note the white tissue in the absence of NAC which represents dead and dying tissue. In the presence of NAC the amount of white tissue is minimal.

Figure 44:
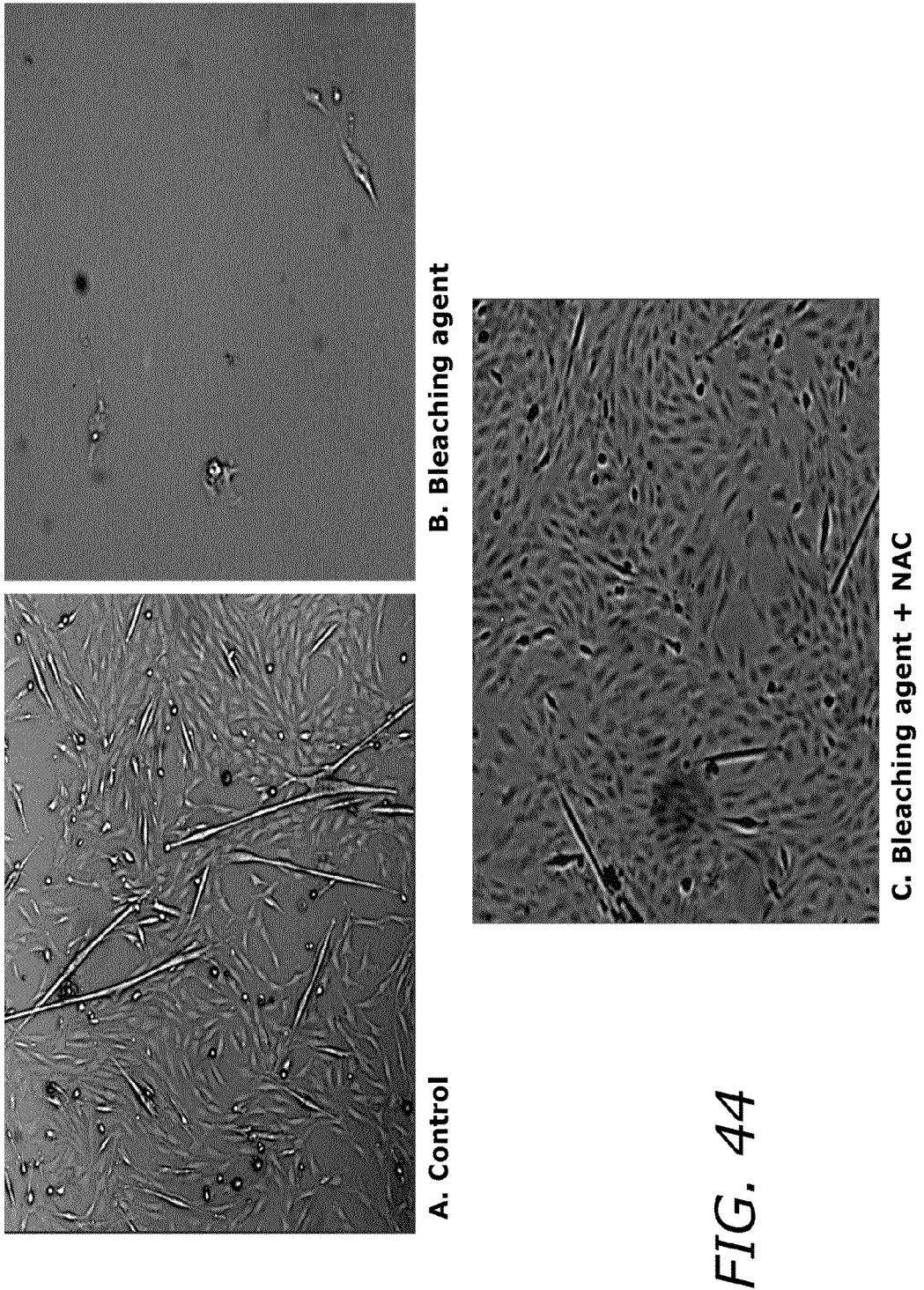
FIGS. 44A-C show the protective effect of NAC (FIG. 44C) in the presence of bleaching agents (FIG. 44B) in gingival cells as compared to control cells (FIG. 44A).
Figure 46:
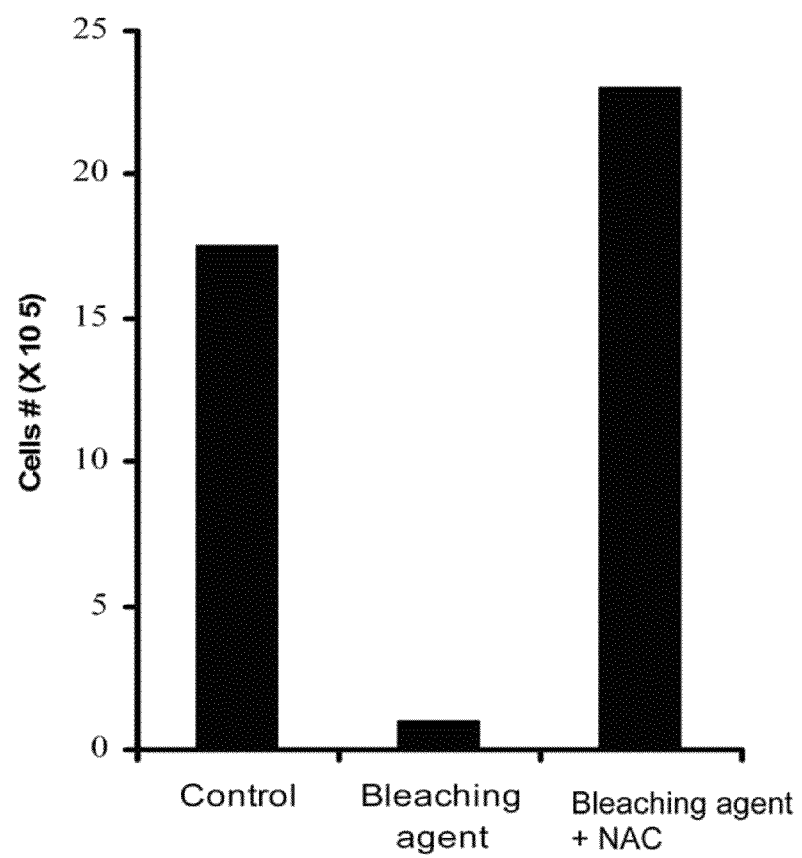
FIG. 46 shows the protective effect of NAC in the presence of bleaching agents in gingival fibroblasts.

For gingival cells, the bleaching agent was applied in the same order of experimental groups to the palatal gingiva for 5 hours, washed and excised and minced and treated with collagenase (0.01%) for 48 hours before the single cell suspensions were prepared by washing and resuspending in DMEM. The cells were allowed to grow to confluency for 21 days before photographs were taken. FIG. 44 shows the results relating to gingival cells. Again, the bleaching agent resulted in a significant amount of cell death (FIG. 44B) which was ameliorated by the presence of NAC (FIG. 44C). FIG. 46 provides a graphical representation of cell survival.

Figure 45:
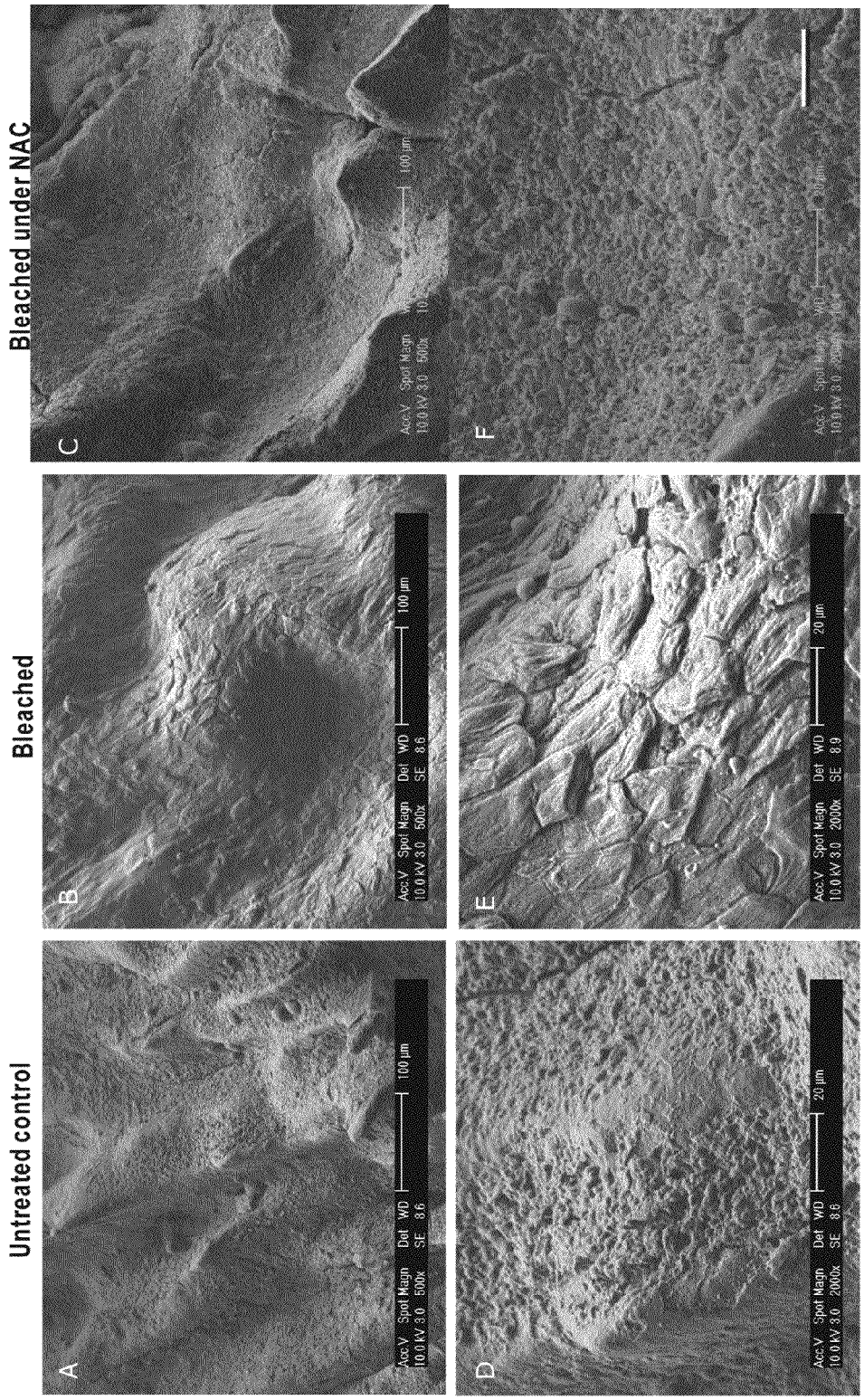
FIGS. 45A-F show the smooth texture of bleached tissue as compared to untreated controls at 500× (A-C) and 2000× magnifications (D-F) and that NAC treated (C and F) and bleached tissue (B and E) demonstrates a similar pattern of tissue as untreated control tissue (A and D) in gingival fibroblasts.

For palatal tissue, the same groups and methods were used as described above except that the palatal tissue was washed, excised and left in PBS until analyzed by scanning electron microscope (FIG. 45). Note the smooth texture of bleached tissue (B and E) as compared to untreated control (A and D). NAC-treated (C and F) and bleached tissue demonstrated a similar pattern of tissue to untreated control tissue.

Figure 47A:
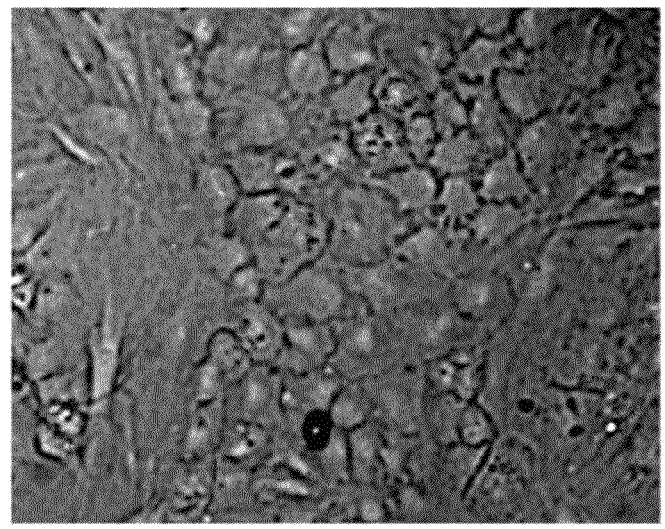
FIG. 47A depicts control cells.
Figure 47B:
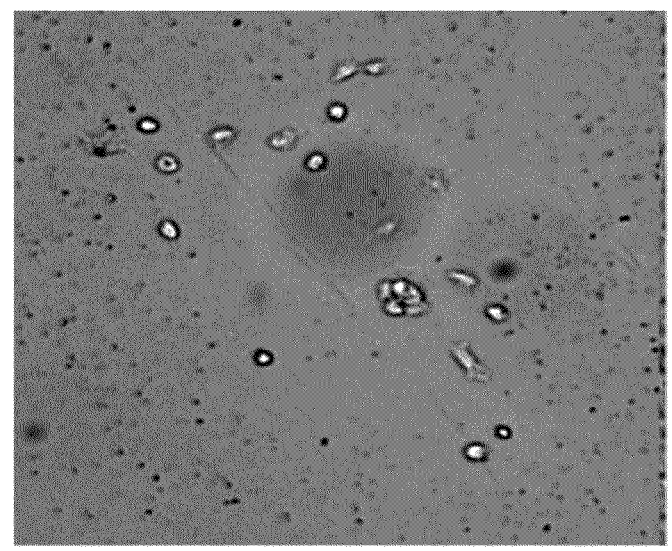
FIG. 47B depicts cells in the presence of bleaching agent and FIG. 47C depicts cells in the presence of bleaching agent and NAC.
Figure 47C:
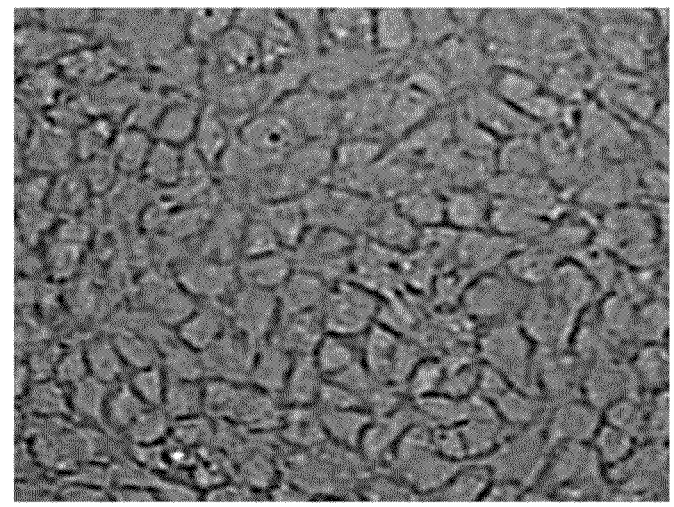
Figure 48:
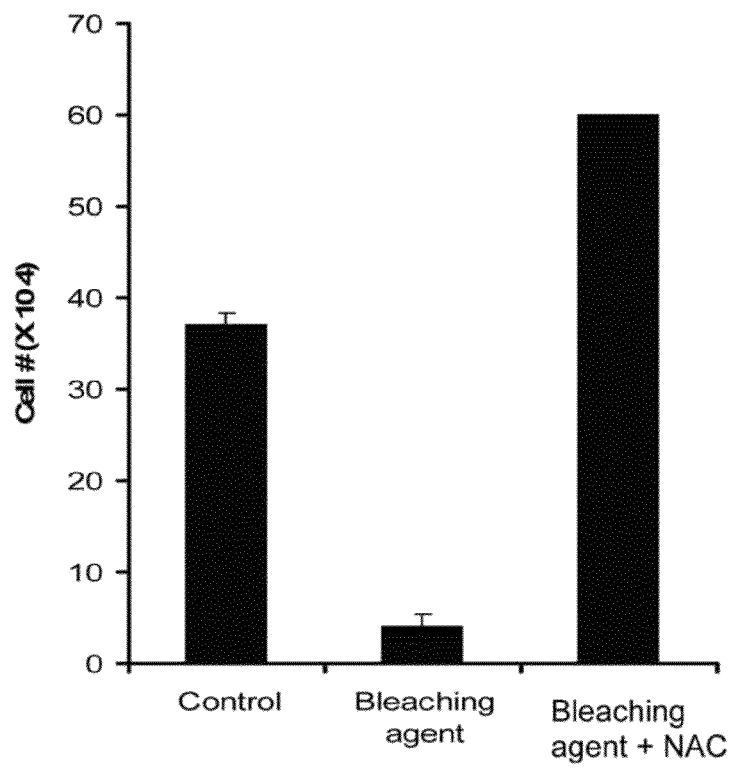
Figure 49:
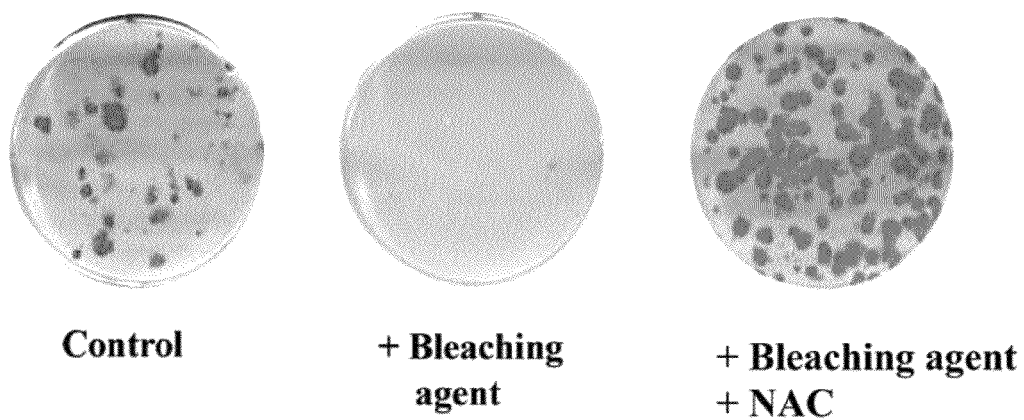

Similar studies were also carried out using dental pulp stromal cells. Rats were divided into three groups: (1) Control (no bleach); (2) Bleach; and (3) Bleach and NAC. In these studies, NAC was initially painted on to the teeth (20 mM concentration) for 5 minutes and then bleaching agent applied for 5 hours, after which the teeth were extracted, and pulp was obtained from each group. Pulp was treated with trypsin/EDTA (0.25%) and collagenase (0.02%) to obtain single cell suspension of the cells, washed and resuspended in DMEM containing β-glycerophosphate (10 mM) and ascorbic acid (50 µg/ml), and allowed to grow to confluency, before either photographs were taken (12-21 days; FIG. 47); cells were counted (21 days; FIG. 48); or ALP staining was performed (21 days; FIG. 49). As can be seen in these FIGS. 47-49, the bleaching treatment caused a significant amount of cytotoxicity and cell death that could be reversed by treatment with NAC.

2. Whitening Strips

Figure 50:
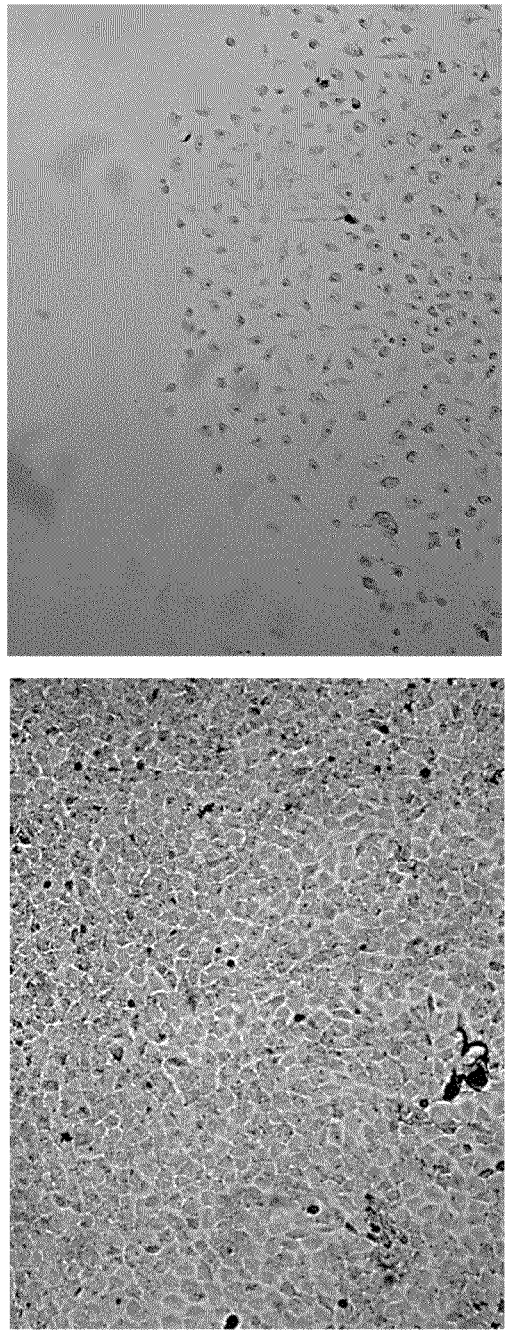
FIGS. 50-52 show the effect of whitening strips on rat dental pulp stromal cells.
Figure 51:
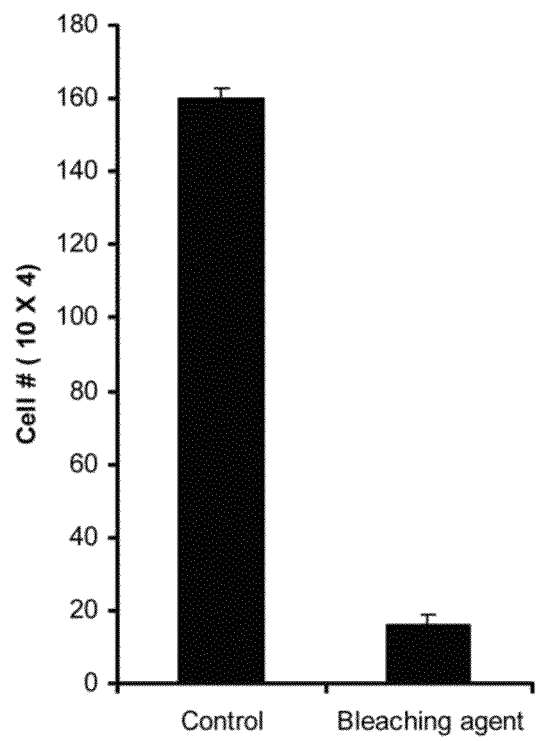
Figure 52:
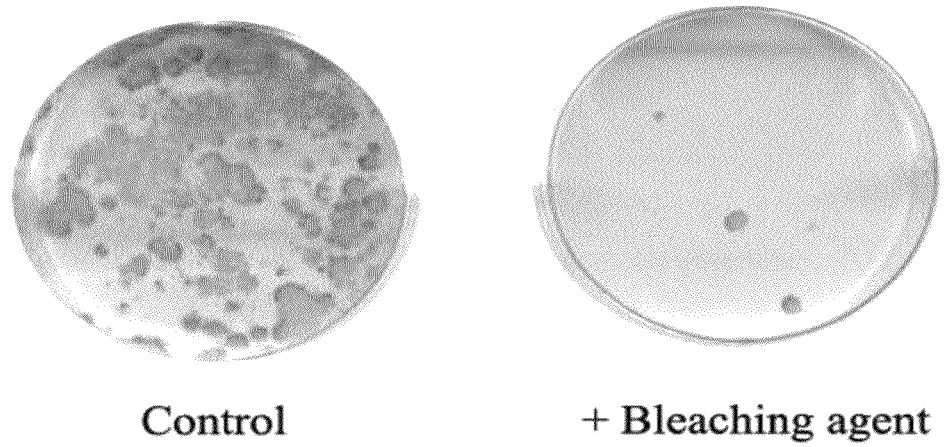

The effect of whitening strips on cytotoxicity was also investigated. Rats were divided into two groups: (1) Control; and (2) Bleached. The bleaching agent used in these studies was Tres White an over the counter tooth whitening product. In the described studies, bleaching strips were left on the teeth for 9 hours as is directed to be done in home use. Following this bleaching treatment, the teeth were extracted, and pulp was obtained from each group and treated with trypsin/EDTA (0.25%) and collagenase (0.02%) to obtain single cell suspensions of the cells. Cells were then washed and resuspended in DMEM containing β-glycerophosphate (10 mM) and ascorbic acid (50 µg/ml), and allowed to grow to confluency (21 days). Following this treatment, pictures were taken (FIG. 50); cells were counted (FIG. 51); and ALP staining was performed (FIG. 52). As can be seen in these FIGS. 50-52, the bleaching treatment caused a significant amount of cytotoxicity and cell death. It is likely that this cytotoxicity and cell death can be reversed by treatment with NAC.

3. Stem Cells

Figure 53:
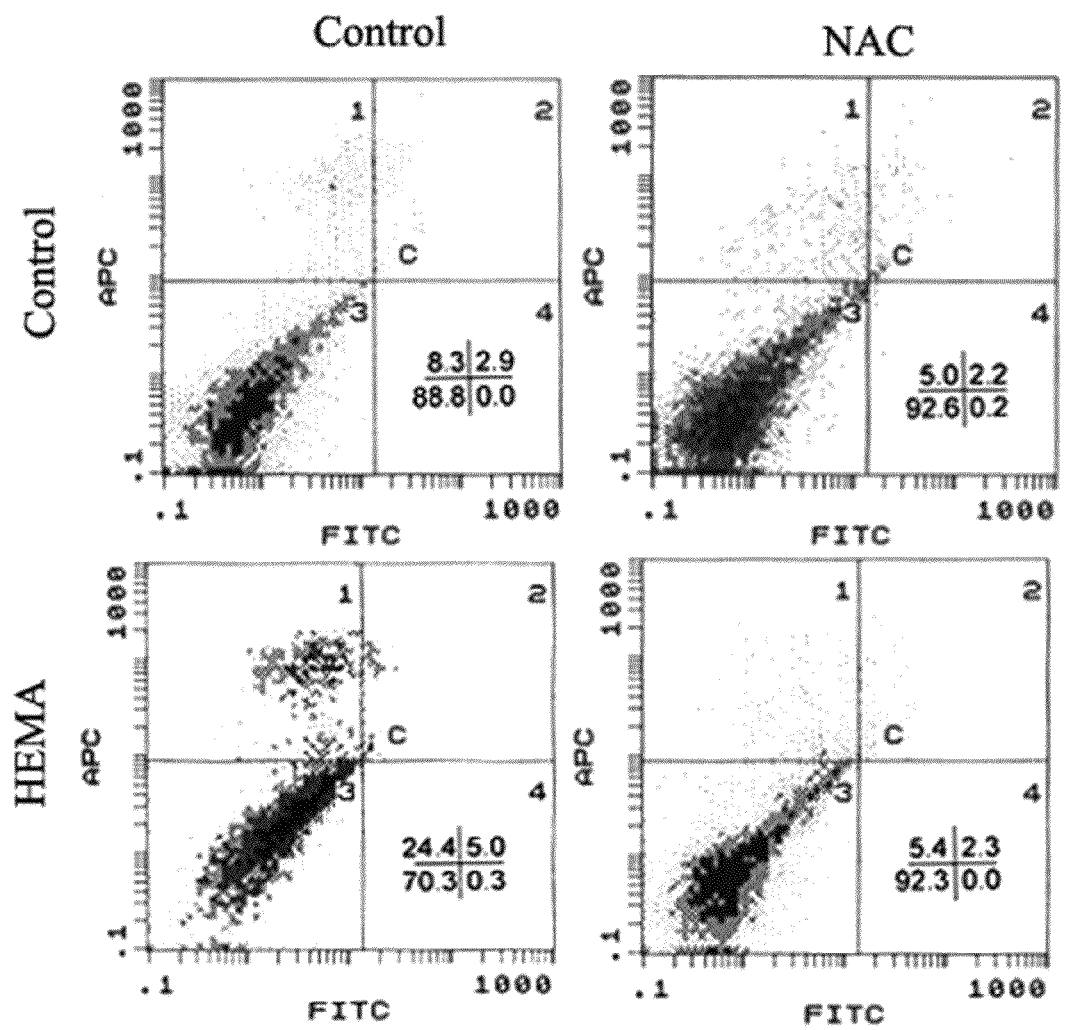
FIG. 53 shows the effect of NAC on HEMA-mediated cell death in human perivascular stem cells.

Human perivascular stem cells were treated with HEMA (0.082M) in the absence and presence of NAC (20 mM) for 4 hours, after which the cells were washed and cultured in an overnight assay before a cell death assay was performed. FITC-Annexin V (X axis) and PI (Y axis) was used to determine the levels of cell death. FIG. 53 shows the effect of NAC on the inhibition of HEMA mediated cell death in human perivascular stem cells (the numbers provided in FIG. 53 represent the percentages of cells in each quadrant).

Figure 54:
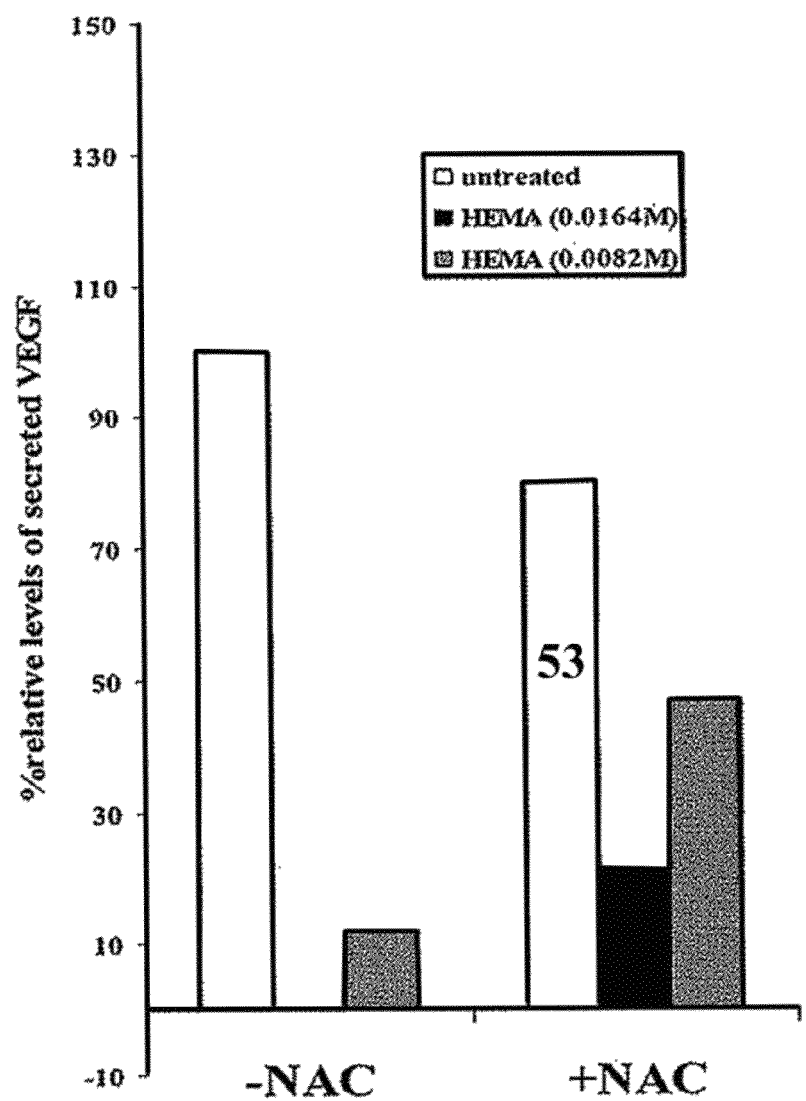
FIG. 54 shows a relative decrease in VEGF secretion in the presence of HEMA and its prevention by NAC in human mesenchymal stem cells.

Next, human mesenchymal stem cells were treated with HEMA as indicated in FIG. 54 in the absence and presence of NAC (20 mM) for 4 hours, after which the cells were washed and cultured in an overnight assay before supernatants were removed and VEGF secretion was determined by ELISA. Relative decrease in VEGF secretion in the presence of HEMA and its prevention by NAC was determined compared to the levels obtained by the control untreated mesenchymal stem cells. FIG. 54 shows a relative decrease in VEGF secretion in the presence of HEMA and its prevention by NAC in human mesenchymal stem cells. Thus, HEMA treatment significantly decreased secretion of VEGF from mesenchymal stem cells in a dose dependent manner and treatment with NAC prevented the HEMA-mediated decrease.

Figure 55:
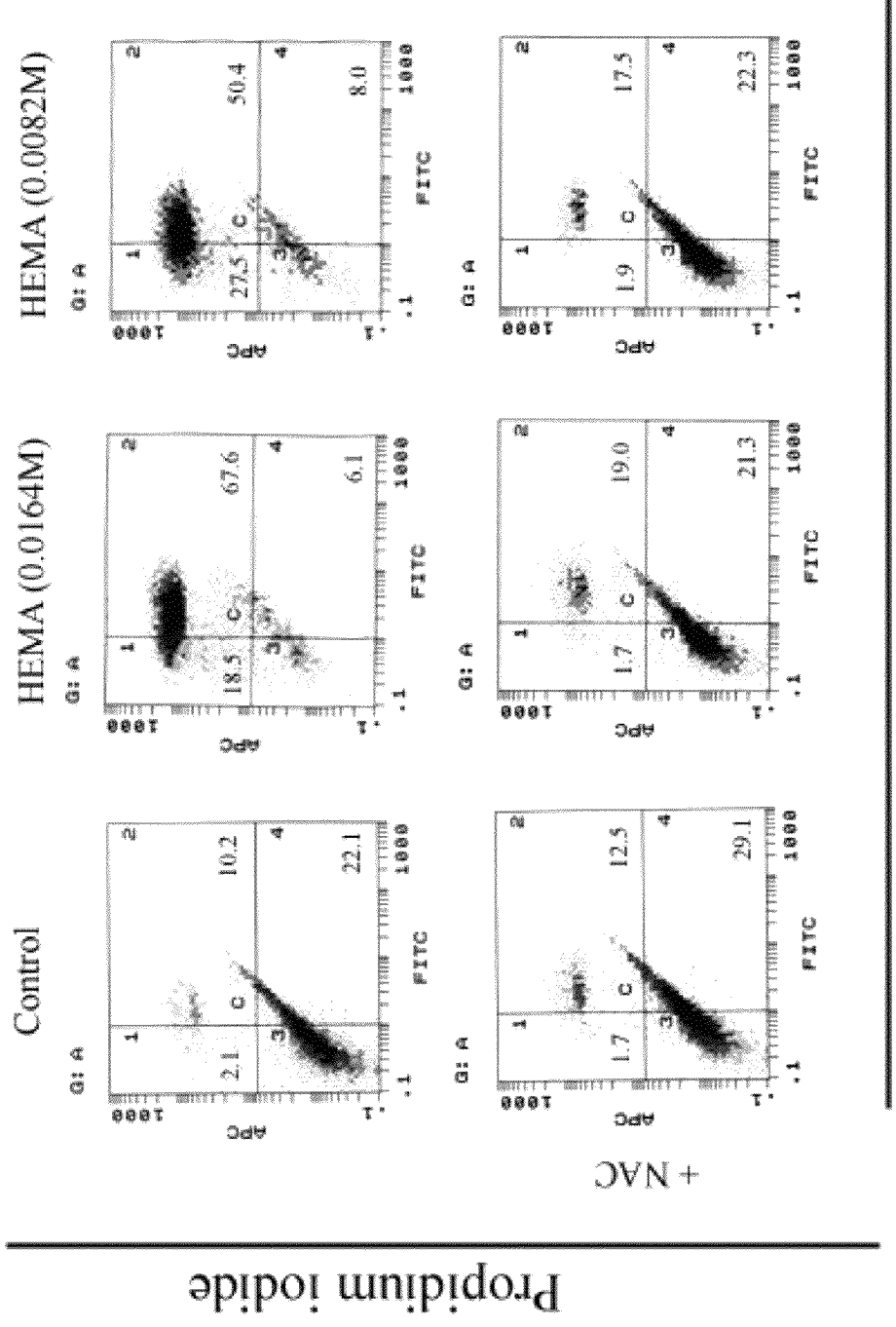
FIG. 55 shows that NAC can prevent HEMA-mediated cell death in mesenchymal stem cells.

Mesenchymal stem cells were also cultured with HEMA in the presence and absence of NAC (20 mM) for 18 hours (FIG. 55). Treated mesenchymal stem cells were then removed and cell death determined using FITC-Annexin V and PI staining. As can be seen in FIG. 55, NAC can prevent HEMA-mediated cell death in mesenchymal stem cells.

Figure 56:
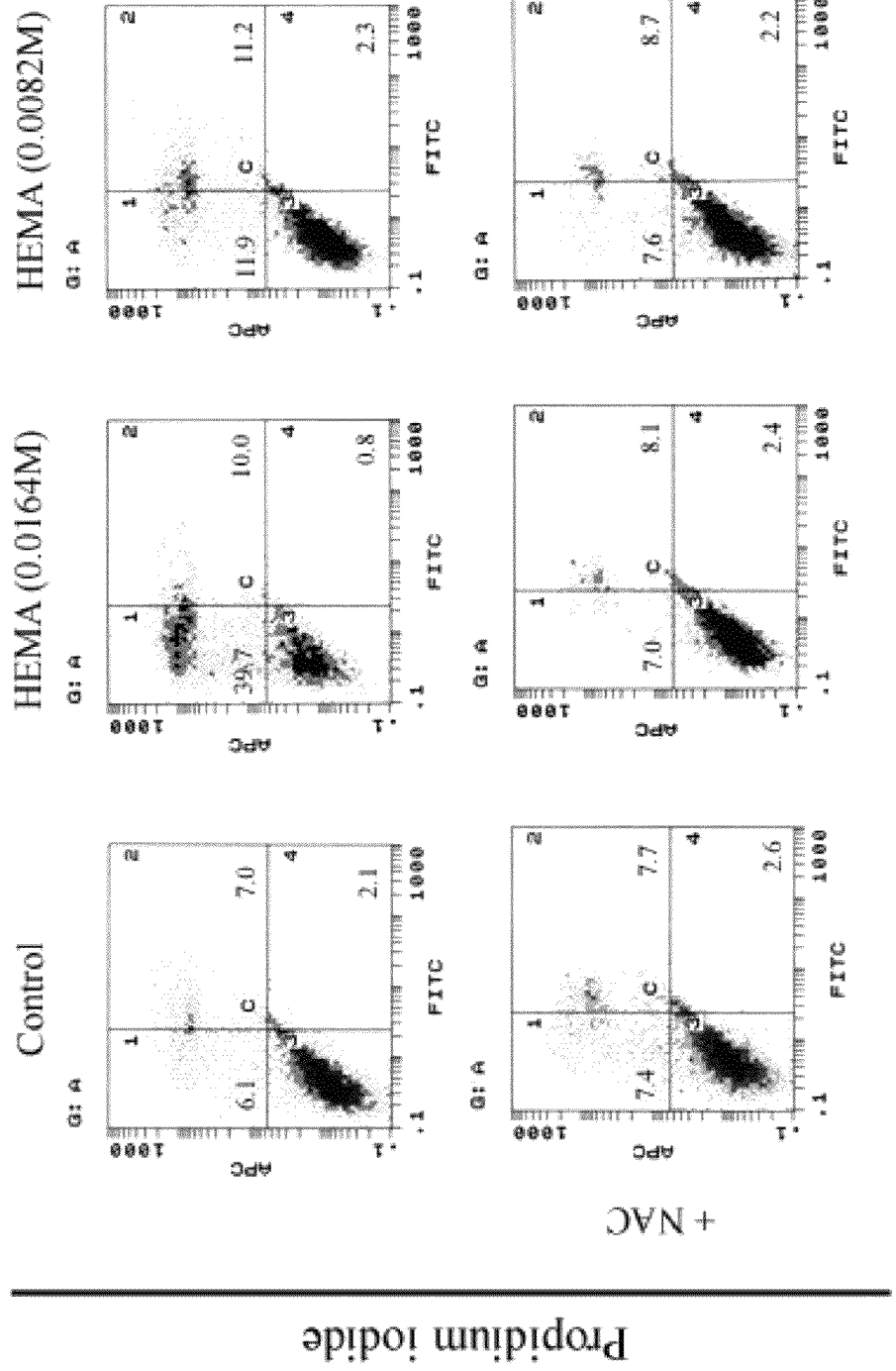
FIG. 56 shows that NAC can prevent HEMA-mediated cell death in osteoblasts.

In a subsequent study, mesenchymal stem cells were differentiated to osteoblasts in differentiation media. Osteoblasts were then plated and HEMA was added in the presence and absence of NAC (20 mM) for 18 hours (FIG. 56). Treated osteoblasts were then removed and cell death was determined using FITC-Annexin V and PI staining. As can be seen in FIG. 56, NAC can prevent HEMA-mediated cell death in osteoblasts.

Further, when compared to mesenchymal stem cells (FIG. 55), lower numbers of osteoblasts underwent cell death (86.1% vs. 49.7%) at 0.0164M concentrations of HEMA. Therefore, differentiation of stem cells to osteoblasts protected the cells from undergoing cell death. In addition NAC was able to prevent cell death mediated by HEMA in osteoblasts. Therefore, the effect of NAC resembles that of signals given during differentiation of the cells with well-established differentiation factors.

4. Muscle Cells

Figure 57:
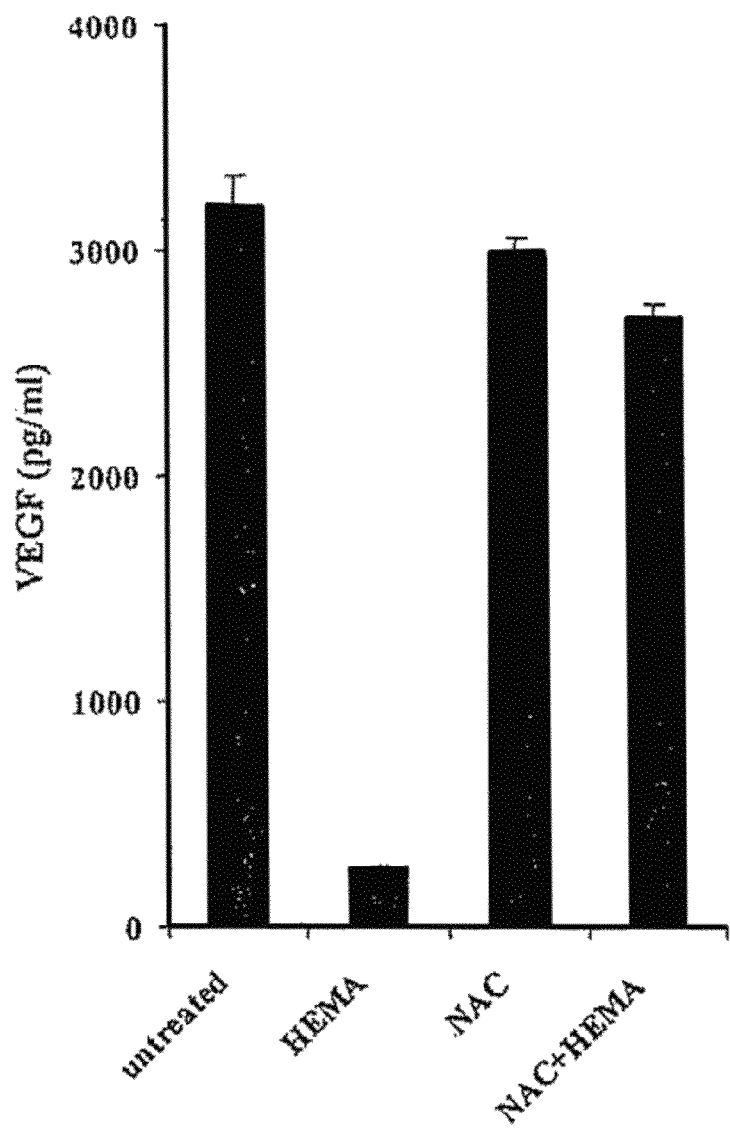
FIG. 57 shows that HEMA treatment significantly reduced VEGF secretion in human smooth muscle cells, an effect that could be reversed by treatment with NAC.

Human smooth muscle cells extracted from the heart were treated with HEMA (0.082M) in the absence and presence of NAC (20 mM) for 4 hours, after which the cells were washed and cultured in an overnight assay before supernatants were removed to measure secreted VEGF by ELISA. As can be seen in FIG. 57, HEMA treatment significantly reduced VEGF secretion, an effect that could be reversed by treatment with NAC.

Figure 58:
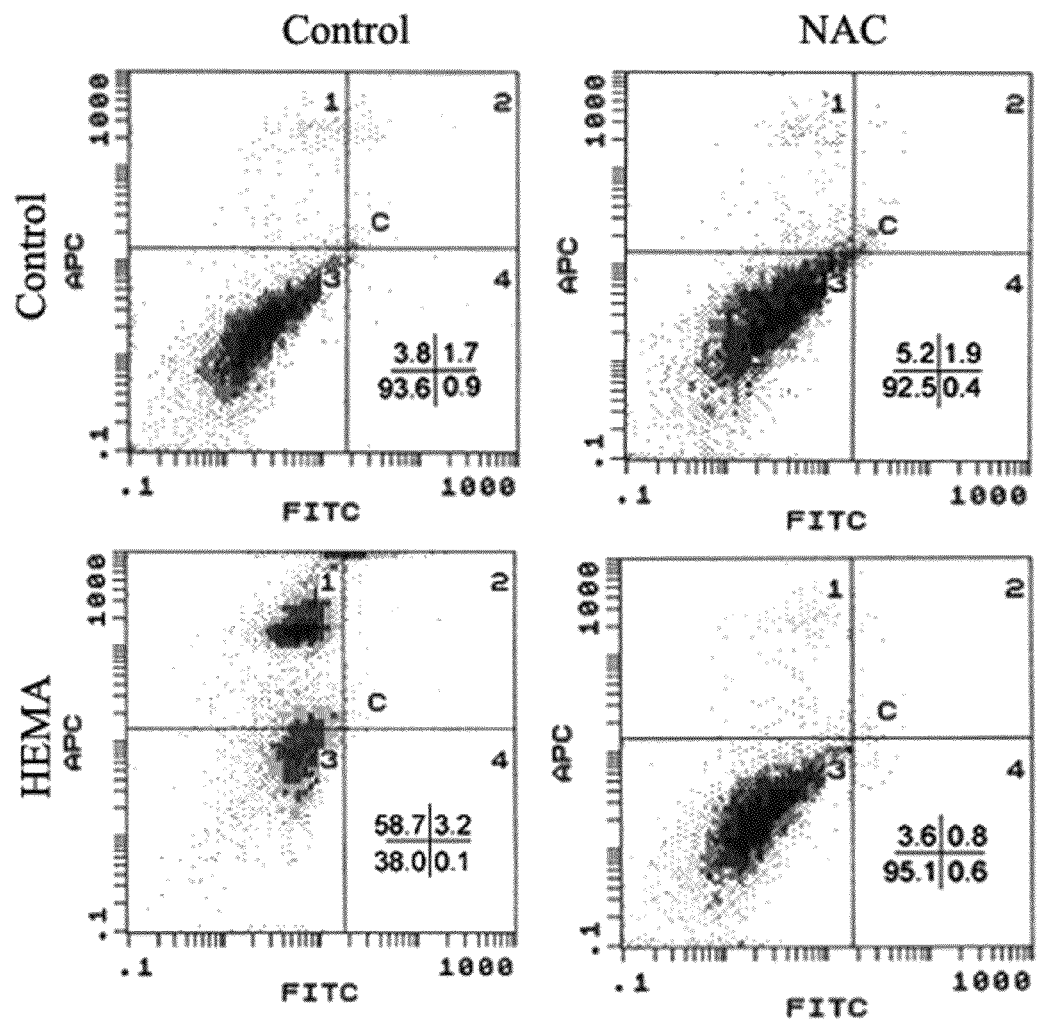
FIG. 58 shows the effect of NAC on the inhibition of HEMA-mediated cell death in smooth muscle cells.

Next, human smooth muscle cells were treated with HEMA (0.082M) in the absence and presence of NAC (20 mM) for 4 hours, after which the cells were washed and cultured in an overnight assay before a cell death assay was performed. FITC-Annexin V (X axis) and PI (Y axis) was used to determine the levels of cell death. Thus, FIG. 58 shows the effect of NAC on the inhibition of HEMA mediated cell death in smooth muscle cells (numbers provided in FIG. 58 represent the percentage of cells in each quadrant).

5. Treatment of Human Teeth

Three freshly extracted human teeth were obtained. Cavity preparations were performed on 2 freshly extracted third molars before restoration. One molar was left untouched and used as control. Specifically, tooth #1 was left untreated; tooth #2 was restored with composite resin alone; and tooth #3 was restored with composite resin after application of NAC. Restorations were left for 5 hours after which the teeth were cracked and the pulps removed and subjected to Trypsin/EDTA (0.25%) and collagenase (0.02%) treatment. Single cell suspensions of control and each restored tooth were then cultured in the presence of β-glycerophosphate (10 mM) and ascorbic acid (50 μg/ml) and microscopic pictures taken after 14 days of incubation for growth.

Figure 59:
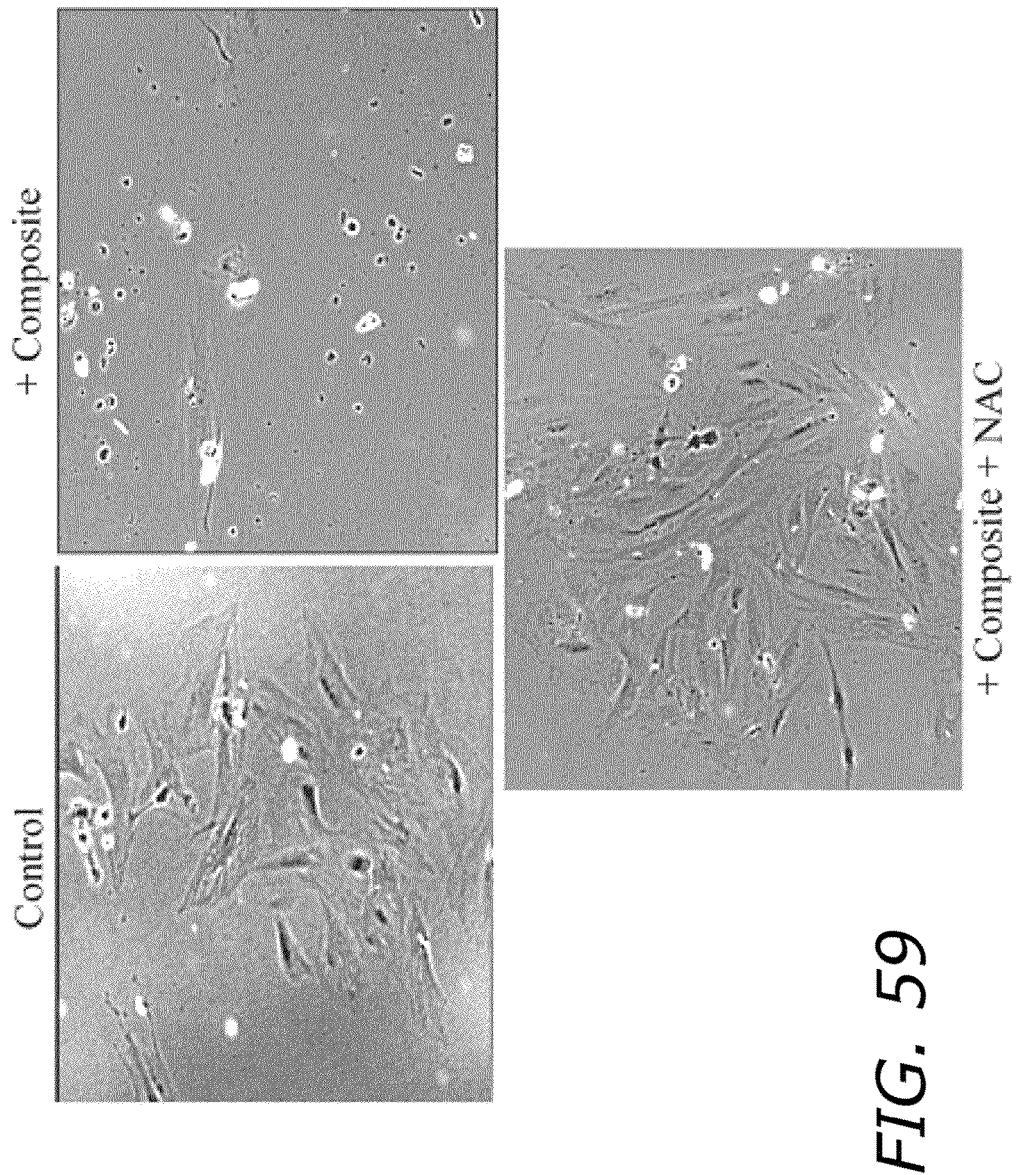
FIG. 59 shows that restoration with composites inhibited growth of cells whereas when NAC was applied before restoration growth and expansion of the cells resulted in human teeth.

As can be seen in FIG. 59, restoration with composites resulted in no growth of pulp cells whereas when NAC was applied before restoration growth and expansion of the cells resulted. Further, the growth of cells in the NAC-treated tooth before restoration were equal or better than that obtained from the untreated tooth. Thus, FIG. 59 demonstrates that NAC prevented loss of human dental pulp stromal cells after ex in vivo composite restoration.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention can be combined with any one or more other features of any other embodiment of the invention, without departing from the scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are individually incorporated by reference herein in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A dental bleaching combination comprising:
    an effective amount of a dental bleaching agent comprising hydrogen peroxide; and
    an amount of N-acetyl cysteine (NAC) effective to reduce cytotoxicity observed with the bleaching agent, wherein the effective amount of NAC is from about 10 mM to about 30 mM.

2. The combination of claim 1, wherein the effective amount of NAC is about 20 mM.

3. The combination of claim 1, wherein the NAC is provided separately from the bleaching agent to permit application of the NAC prior to application of the bleaching agent.

4. The combination of claim 1, wherein the effective amount of dental bleaching agent comprises 33% hydrogen peroxide.

5. The combination of claim 4, wherein the effective amount of NAC is about 20 mM.

6. The combination of claim 5, wherein the NAC is provided separately from the bleaching agent to permit application of the NAC prior to application of the bleaching agent.

* * * * *